US009102680B2

(12) United States Patent
Smolenskaya et al.

(10) Patent No.: US 9,102,680 B2
(45) Date of Patent: Aug. 11, 2015

(54) CRYSTAL FORMS OF (R)-N-METHYLNALTREXONE BROMIDE AND USES THEREOF

(71) Applicants: Progenics Pharmaceuticals., Inc., Tarrytown, NY (US); Wyeth, LLC, Madison, NJ (US)

(72) Inventors: Valeriya N. Smolenskaya, West Lafayette, IN (US); Kadum A. Al Shareffi, North Potomac, MD (US); Julio Perez, Tarrytown, NY (US); Syed M. Shah, Delray Beach, FL (US); Thomas A. Boyd, Grandview, NY (US)

(73) Assignees: Wyeth LLC, Madison, NJ (US); Progenics Pharmamceuticals, Inc., Tarrytown, NY (US)

( * ) Notice: Subject to any disclaimer, the term of this patent is extended or adjusted under 35 U.S.C. 154(b) by 0 days.

(21) Appl. No.: 13/682,878

(22) Filed: Nov. 21, 2012

(65) Prior Publication Data

US 2014/0004188 A1      Jan. 2, 2014

Related U.S. Application Data

(63) Continuation of application No. 12/593,615, filed as application No. PCT/US2008/004116 on Mar. 28, 2008, now abandoned.

(60) Provisional application No. 60/921,111, filed on Mar. 29, 2007.

(51) Int. Cl.
| | |
|---|---|
| *C07D 471/00* | (2006.01) |
| *C07D 491/00* | (2006.01) |
| *C07D 498/00* | (2006.01) |
| *C07D 513/00* | (2006.01) |
| *C07D 515/00* | (2006.01) |
| *C07D 489/00* | (2006.01) |
| *A61K 31/44* | (2006.01) |
| *C07D 489/08* | (2006.01) |
| *C07D 489/04* | (2006.01) |
| *A61K 31/485* | (2006.01) |

(52) U.S. Cl.
CPC ............ *C07D 489/08* (2013.01); *A61K 31/485* (2013.01); *C07D 489/04* (2013.01)

(58) Field of Classification Search
None
See application file for complete search history.

(56) References Cited

U.S. PATENT DOCUMENTS

| | | |
|---|---|---|
| 3,714,159 A | 1/1973 | Janssen et al. |
| 3,723,440 A | 3/1973 | Freter et al. |
| 3,854,480 A | 12/1974 | Zaffaroni |
| 3,884,916 A | 5/1975 | Janssen et al. |
| 3,937,801 A | 2/1976 | Lippmann |
| 3,996,214 A | 12/1976 | Dajani et al. |
| 4,012,393 A | 3/1977 | Markos et al. |
| 4,013,668 A | 3/1977 | Adelstein et al. |
| 4,025,652 A | 5/1977 | Diamond et al. |
| 4,060,635 A | 11/1977 | Diamond et al. |
| 4,066,654 A | 1/1978 | Adelstein et al. |
| 4,069,223 A | 1/1978 | Adelstein |
| 4,072,686 A | 2/1978 | Adelstein et al. |
| 4,115,400 A | 9/1978 | Zimmerman |
| 4,115,564 A | 9/1978 | Diamond et al. |
| 4,116,963 A | 9/1978 | Adelstein |
| 4,125,531 A | 11/1978 | Yen |
| 4,176,186 A | 11/1979 | Goldberg et al. |
| 4,194,045 A | 3/1980 | Adelstein |
| 4,203,920 A | 5/1980 | Diamond et al. |
| 4,241,066 A | 12/1980 | Kobylecki et al. |
| 4,277,605 A | 7/1981 | Buyniski et al. |
| 4,311,833 A | 1/1982 | Namikoshi et al. |
| 4,322,426 A | 3/1982 | Hermann et al. |
| 4,326,074 A | 4/1982 | Diamond et al. |
| 4,326,075 A | 4/1982 | Diamond et al. |
| 4,377,568 A | 3/1983 | Chopra et al. |
| 4,385,078 A | 5/1983 | Onda et al. |
| 4,427,676 A | 1/1984 | White et al. |
| 4,430,327 A | 2/1984 | Frederickson et al. |
| 4,452,775 A | 6/1984 | Kent |
| 4,457,907 A | 7/1984 | Porter et al. |
| 4,462,839 A | 7/1984 | McGinley et al. |
| 4,466,968 A | 8/1984 | Bernstein |
| 4,518,433 A | 5/1985 | McGinley et al. |
| 4,533,739 A | 8/1985 | Pitzele et al. |
| 4,556,552 A | 12/1985 | Porter et al. |
| 4,606,909 A | 8/1986 | Bechgaard et al. |
| 4,615,885 A | 10/1986 | Nakagame et al. |

(Continued)

FOREIGN PATENT DOCUMENTS

| | | |
|---|---|---|
| AU | 610 561 | 8/1988 |
| AU | 758 416 B2 | 7/1999 |

(Continued)

OTHER PUBLICATIONS

Goldberg, LI. et al. Variations in demethylation of N-methylnaltrexone in mice, rats, dogs, and humans. Xenobiotica. 1989, vol. 19, p. 1248.*

(Continued)

*Primary Examiner* — Rita Desai
*Assistant Examiner* — Ben S Michelson
(74) *Attorney, Agent, or Firm* — McCarter & English, LLP; Jonathan M. Sparks; Maneesh Gulati, Esq.

(57) ABSTRACT

The present invention provides a new forms of (R)—N-methylnaltrexone, and compositions thereof, useful as a peripheral mu opioid receptor antagonist.

14 Claims, 10 Drawing Sheets

(56) References Cited

U.S. PATENT DOCUMENTS

| | | |
|---|---|---|
| 4,670,287 A | 6/1987 | Tsuji et al. |
| 4,675,189 A | 6/1987 | Kent et al. |
| 4,689,332 A | 8/1987 | McLaughlin et al. |
| 4,719,215 A | 1/1988 | Goldberg |
| 4,730,048 A | 3/1988 | Portoghese |
| 4,765,978 A | 8/1988 | Abidi et al. |
| 4,806,556 A | 2/1989 | Portoghese |
| 4,824,853 A | 4/1989 | Wals et al. |
| 4,836,212 A | 6/1989 | Schmitt et al. |
| 4,837,214 A | 6/1989 | Tanaka et al. |
| 4,857,533 A | 8/1989 | Sherman et al. |
| 4,861,781 A | 8/1989 | Goldberg |
| 4,863,928 A | 9/1989 | Atkinson et al. |
| 4,867,979 A | 9/1989 | Sheth et al. |
| 4,870,084 A | 9/1989 | Eggler et al. |
| 4,888,346 A | 12/1989 | Bihari et al. |
| 4,891,379 A | 1/1990 | Zimmerman et al. |
| 4,912,114 A | 3/1990 | Revesz |
| 4,965,269 A | 10/1990 | Brändström et al. |
| 4,987,136 A | 1/1991 | Kreek et al. |
| 4,990,521 A | 2/1991 | Van Daele et al. |
| 4,999,342 A | 3/1991 | Ahmad et al. |
| 5,102,887 A | 4/1992 | Goldberg |
| 5,116,868 A | 5/1992 | Chen et al. |
| 5,133,974 A | 7/1992 | Paradissis et al. |
| 5,159,081 A | 10/1992 | Cantrell et al. |
| 5,202,159 A | 4/1993 | Chen et al. |
| 5,220,017 A | 6/1993 | Bock et al. |
| 5,236,947 A | 8/1993 | Calvet et al. |
| 5,250,542 A | 10/1993 | Cantrell et al. |
| 5,256,154 A | 10/1993 | Liebert et al. |
| 5,270,328 A | 12/1993 | Cantrell et al. |
| 5,312,899 A | 5/1994 | Schiller |
| 5,391,372 A | 2/1995 | Campbell |
| 5,407,686 A | 4/1995 | Patel et al. |
| 5,426,112 A | 6/1995 | Zagon et al. |
| 5,434,171 A | 7/1995 | Frank et al. |
| 5,472,943 A | 12/1995 | Crain et al. |
| 5,512,578 A | 4/1996 | Crain et al. |
| 5,536,507 A | 7/1996 | Abramowitz et al. |
| 5,567,423 A | 10/1996 | Ying et al. |
| 5,585,348 A | 12/1996 | Crain et al. |
| 5,591,433 A | 1/1997 | Michael et al. |
| 5,597,564 A | 1/1997 | Ying et al. |
| 5,609,871 A | 3/1997 | Michael et al. |
| 5,614,219 A | 3/1997 | Wunderlich et al. |
| 5,614,222 A | 3/1997 | Kaplan et al. |
| 5,626,875 A | 5/1997 | Ballester Rodes et al. |
| 5,629,001 A | 5/1997 | Michael et al. |
| 5,656,290 A | 8/1997 | Kelm et al. |
| 5,686,072 A | 11/1997 | Uhr et al. |
| 5,714,586 A | 2/1998 | Kunstmann et al. |
| 5,739,152 A | 4/1998 | Andersson et al. |
| 5,767,125 A | 6/1998 | Crain et al. |
| 5,804,595 A | 9/1998 | Portoghese et al. |
| 5,811,451 A | 9/1998 | Minoia et al. |
| 5,821,219 A | 10/1998 | Grandy et al. |
| 5,866,154 A | 2/1999 | Bahal et al. |
| 5,866,164 A | 2/1999 | Kuczynski et al. |
| 5,958,452 A | 9/1999 | Oshlack et al. |
| 5,972,954 A | 10/1999 | Foss et al. |
| 5,981,185 A | 11/1999 | Matson et al. |
| RE36,547 E | 2/2000 | Crain et al. |
| 6,025,154 A | 2/2000 | Li et al. |
| 6,096,756 A | 8/2000 | Crain et al. |
| 6,096,763 A | 8/2000 | Hoffman et al. |
| 6,096,764 A | 8/2000 | Bryant et al. |
| 6,099,853 A | 8/2000 | Hertelendy et al. |
| 6,136,780 A | 10/2000 | Zagon et al. |
| 6,153,620 A | 11/2000 | Kornetsky |
| 6,190,691 B1 | 2/2001 | Mak |
| 6,194,382 B1 | 2/2001 | Crain et al. |
| 6,261,599 B1 | 7/2001 | Oshlack et al. |
| 6,274,591 B1 | 8/2001 | Foss et al. |
| 6,277,384 B1 | 8/2001 | Kaiko et al. |
| 6,353,004 B1 | 3/2002 | Farrar et al. |
| 6,359,111 B1 | 3/2002 | Meyer et al. |
| 6,362,194 B1 | 3/2002 | Crain et al. |
| 6,384,044 B1 | 5/2002 | Bihari |
| 6,395,705 B2 | 5/2002 | Crain et al. |
| 6,419,959 B1 | 7/2002 | Walter et al. |
| 6,426,094 B1 | 7/2002 | Piver et al. |
| 6,451,806 B2 | 9/2002 | Farrar |
| 6,455,537 B1 | 9/2002 | Cooper |
| 6,469,030 B2 | 10/2002 | Farrar et al. |
| 6,479,500 B1 | 11/2002 | Fukushima et al. |
| 6,559,158 B1 | 5/2003 | Foss et al. |
| 6,608,075 B2 | 8/2003 | Foss et al. |
| 6,693,125 B2 | 2/2004 | Borisy et al. |
| 6,696,066 B2 | 2/2004 | Kaiko et al. |
| 6,720,336 B2 | 4/2004 | Liras |
| 6,723,712 B2 | 4/2004 | Bourhis et al. |
| 6,734,188 B1 | 5/2004 | Rhodes et al. |
| 6,756,364 B2 | 6/2004 | Barbier et al. |
| 6,777,534 B1 | 8/2004 | Klagsbrun et al. |
| 6,794,370 B2 | 9/2004 | Achterrath |
| 6,800,639 B2 | 10/2004 | Giles et al. |
| 6,833,349 B2 | 12/2004 | Xia et al. |
| 6,838,469 B2 | 1/2005 | Sumegi |
| 6,884,879 B1 | 4/2005 | Baca et al. |
| 6,900,234 B1 | 5/2005 | Fossa |
| 6,946,556 B1 | 9/2005 | Likhotvorik et al. |
| 6,960,596 B2 | 11/2005 | Bissery |
| 6,967,016 B2 | 11/2005 | van Gemen et al. |
| 6,984,403 B2 | 1/2006 | Hagen et al. |
| 6,986,901 B2 | 1/2006 | Meisel et al. |
| 6,989,383 B1 | 1/2006 | Rosen et al. |
| 6,992,106 B2 | 1/2006 | Morinaga et al. |
| 7,012,100 B1 | 3/2006 | Edwards et al. |
| 7,074,825 B2 | 7/2006 | Mo et al. |
| 7,094,775 B2 | 8/2006 | Strugnell et al. |
| 7,129,265 B2 | 10/2006 | Mason |
| 7,132,554 B2 | 11/2006 | Rose |
| 7,141,554 B2 | 11/2006 | Rochat et al. |
| 7,160,913 B2 | 1/2007 | Schneider |
| 7,183,269 B2 | 2/2007 | Kreutz |
| 7,196,115 B2 | 3/2007 | Khanuja et al. |
| 7,259,233 B2 | 8/2007 | Dodd et al. |
| 7,501,434 B2 | 3/2009 | Shah et al. |
| 7,563,899 B2 | 7/2009 | Boyd et al. |
| 7,674,904 B2 | 3/2010 | Doshan et al. |
| 8,343,992 B2 | 1/2013 | Doshan et al. |
| 8,471,022 B2 | 6/2013 | Avey et al. |
| 8,546,418 B2 | 10/2013 | Avey et al. |
| 2001/0010919 A1 | 8/2001 | Grandy et al. |
| 2001/0018413 A1 | 8/2001 | Crain et al. |
| 2001/0033865 A1 | 10/2001 | Oshlack et al. |
| 2001/0036469 A1 | 11/2001 | Gooberman |
| 2001/0036476 A1 | 11/2001 | Oshlack et al. |
| 2001/0036951 A1 | 11/2001 | Farrar et al. |
| 2001/0046968 A1 | 11/2001 | Zagon et al. |
| 2001/0047005 A1 | 11/2001 | Farrar et al. |
| 2002/0028825 A1 | 3/2002 | Foss et al. |
| 2002/0064771 A1 | 5/2002 | Zhong et al. |
| 2002/0068712 A1 | 6/2002 | Stevens |
| 2002/0173466 A1 | 11/2002 | Crain et al. |
| 2002/0176888 A1 | 11/2002 | Bartholomaeus et al. |
| 2002/0188005 A1 | 12/2002 | Farrar et al. |
| 2003/0022909 A1 | 1/2003 | Moss et al. |
| 2003/0026801 A1 | 2/2003 | Weiner et al. |
| 2003/0039689 A1 | 2/2003 | Chen et al. |
| 2003/0065003 A1 | 4/2003 | Foss et al. |
| 2003/0105121 A1 | 6/2003 | Bihari |
| 2003/0124086 A1 | 7/2003 | Bentley et al. |
| 2003/0144312 A1 | 7/2003 | Schoenhard |
| 2003/0158220 A1 | 8/2003 | Foss et al. |
| 2003/0187010 A1 | 10/2003 | Foss et al. |
| 2003/0191147 A1 | 10/2003 | Sherman et al. |
| 2003/0219406 A1 | 11/2003 | Schroit et al. |
| 2004/0010996 A1 | 1/2004 | Karlstrom et al. |
| 2004/0010997 A1 | 1/2004 | Close |
| 2004/0010998 A1 | 1/2004 | Turco |
| 2004/0024006 A1 | 2/2004 | Simon |
| 2004/0136908 A1 | 7/2004 | Olson et al. |

(56) References Cited

U.S. PATENT DOCUMENTS

| | | |
|---|---|---|
| 2004/0162306 A1 | 8/2004 | Foss et al. |
| 2004/0162307 A1 | 8/2004 | Foss et al. |
| 2004/0162308 A1 | 8/2004 | Foss et al. |
| 2004/0167147 A1 | 8/2004 | Foss et al. |
| 2004/0167148 A1 | 8/2004 | Foss et al. |
| 2004/0180916 A1 | 9/2004 | Levine |
| 2004/0242523 A1 | 12/2004 | Weichselbaum et al. |
| 2004/0254156 A1 | 12/2004 | Le Bourdonnec et al. |
| 2004/0254208 A1 | 12/2004 | Weber et al. |
| 2004/0259898 A1 | 12/2004 | Moss et al. |
| 2004/0259899 A1 | 12/2004 | Sanghvi et al. |
| 2004/0266806 A1 | 12/2004 | Sanghvi et al. |
| 2005/0004029 A1 | 1/2005 | Garcia |
| 2005/0004155 A1 | 1/2005 | Boyd et al. |
| 2005/0011468 A1 | 1/2005 | Moss et al. |
| 2005/0048117 A1 | 3/2005 | Foss et al. |
| 2005/0085514 A1 | 4/2005 | Cosford et al. |
| 2005/0124657 A1 | 6/2005 | Christ et al. |
| 2005/0124885 A1 | 6/2005 | Abend et al. |
| 2005/0187255 A1 | 8/2005 | Lee et al. |
| 2006/0025592 A1 | 2/2006 | Stranix et al. |
| 2006/0063792 A1 | 3/2006 | Dolle et al. |
| 2006/0094658 A1 | 5/2006 | Currie et al. |
| 2006/0115424 A1 | 6/2006 | Gray et al. |
| 2006/0128742 A1 | 6/2006 | Edwards et al. |
| 2006/0204512 A1 | 9/2006 | Krasnoperov et al. |
| 2006/0205753 A1 | 9/2006 | Israel |
| 2006/0258696 A1 | 11/2006 | Moss et al. |
| 2007/0010450 A1 | 1/2007 | Currie et al. |
| 2007/0020261 A1 | 1/2007 | Sliwkowski et al. |
| 2007/0060501 A1 | 3/2007 | Jhamandas et al. |
| 2007/0071761 A1 | 3/2007 | Seon |
| 2007/0082044 A1 | 4/2007 | Yeum |
| 2007/0099946 A1 | 5/2007 | Doshan et al. |
| 2007/0265293 A1 | 11/2007 | Boyd et al. |
| 2008/0064743 A1 | 3/2008 | Shah et al. |
| 2008/0064744 A1 | 3/2008 | Shah et al. |
| 2008/0070975 A1 | 3/2008 | Shah et al. |
| 2008/0075771 A1 | 3/2008 | Vaughn et al. |
| 2008/0103438 A1 | 5/2008 | Prais et al. |
| 2008/0194611 A1 | 8/2008 | Alverdy et al. |
| 2008/0274119 A1 | 11/2008 | Moss et al. |
| 2009/0312359 A1 | 12/2009 | Foss et al. |
| 2010/0087472 A1 | 4/2010 | Foss et al. |
| 2010/0099699 A1 | 4/2010 | Melucci et al. |
| 2010/0105911 A1 | 4/2010 | Wagoner et al. |
| 2010/0120813 A1 | 5/2010 | Bazhina et al. |
| 2010/0249169 A1 | 9/2010 | Shah et al. |
| 2010/0261744 A1 | 10/2010 | Sanghvi et al. |
| 2010/0261745 A1 | 10/2010 | Sanghvi et al. |
| 2010/0261746 A1 | 10/2010 | Sanghvi et al. |
| 2010/0267758 A1 | 10/2010 | Sanghvi et al. |
| 2010/0305323 A1 | 12/2010 | Smolenskaya et al. |
| 2010/0311781 A1 | 12/2010 | Doshan et al. |
| 2013/0296570 A1 | 11/2013 | Avey et al. |
| 2013/0323286 A1 | 12/2013 | Doshan et al. |
| 2014/0142132 A1 | 5/2014 | Avey et al. |

FOREIGN PATENT DOCUMENTS

| | | |
|---|---|---|
| AU | 2003204844 B2 | 9/2007 |
| BE | 876 968 A1 | 10/1979 |
| CA | 2 064 373 A1 | 9/1992 |
| CA | 1 315 689 | 4/1993 |
| CA | 2 312 234 | 5/1999 |
| DE | 3 780 819 T2 | 1/1993 |
| DE | 4 303 214 A1 | 8/1994 |
| DE | 196 51 551 A1 | 6/1998 |
| EP | 0 278 821 A1 | 8/1988 |
| EP | 0 289 070 A1 | 11/1988 |
| EP | 0 306 575 B1 | 3/1989 |
| EP | 0 352 361 A1 | 1/1990 |
| EP | 0 506 468 A1 | 9/1992 |
| EP | 0 643 967 A2 | 3/1995 |
| EP | 0 663 401 A1 | 7/1995 |
| EP | 0 760 661 B1 | 12/1998 |
| EP | 0 984 004 A2 | 3/2000 |
| EP | 1 047 726 B1 | 8/2002 |
| ES | 2226933 T3 | 4/2005 |
| GB | 1 202 148 | 8/1970 |
| JP | 1 068 376 A | 3/1989 |
| JP | 2-25427 | 1/1990 |
| JP | 4-183371 | 6/1992 |
| JP | 4-225922 A | 8/1992 |
| JP | 5-213763 A | 8/1993 |
| JP | 2 625 457 B2 | 7/1997 |
| JP | 4-217924 B2 | 2/2009 |
| NZ | 222911 | 12/1987 |
| SG | 116167 | 1/2008 |
| WO | WO 83/03197 A1 | 9/1983 |
| WO | WO 88/05297 A1 | 7/1988 |
| WO | WO 93/20826 A1 | 10/1993 |
| WO | WO 94/10202 A1 | 5/1994 |
| WO | WO 95/31985 A2 | 11/1995 |
| WO | WO 96/14058 A1 | 5/1996 |
| WO | WO 96/23793 A1 | 8/1996 |
| WO | WO 97/07118 A1 | 2/1997 |
| WO | WO 97/29739 A2 | 8/1997 |
| WO | WO 97/33566 A2 | 9/1997 |
| WO | WO 98/25613 A2 | 6/1998 |
| WO | WO 98/49185 A1 | 11/1998 |
| WO | WO 99/22737 A1 | 5/1999 |
| WO | WO 99/36470 A1 | 7/1999 |
| WO | WO 99/37681 A2 | 7/1999 |
| WO | WO 99/40089 A1 | 8/1999 |
| WO | WO 00/40968 A1 | 7/2000 |
| WO | WO 00/43507 A1 | 7/2000 |
| WO | WO 00/46383 A2 | 8/2000 |
| WO | WO 00/65057 A1 | 11/2000 |
| WO | WO 01/09300 A2 | 2/2001 |
| WO | WO 01/13909 A2 | 3/2001 |
| WO | WO 01/32180 A2 | 5/2001 |
| WO | WO 01/37785 A2 | 5/2001 |
| WO | WO 01/41705 A2 | 6/2001 |
| WO | WO 01/42207 A2 | 6/2001 |
| WO | WO 01/70031 A1 | 9/2001 |
| WO | WO 01/85257 A2 | 11/2001 |
| WO | WO 02/060870 A2 | 8/2002 |
| WO | WO 02/098422 A1 | 12/2002 |
| WO | WO 03/020296 A1 | 3/2003 |
| WO | WO 03/032990 A2 | 4/2003 |
| WO | WO 03/037340 A1 | 5/2003 |
| WO | WO 03/077867 A2 | 9/2003 |
| WO | WO 2004/014291 A2 | 2/2004 |
| WO | WO 2004/043964 A2 | 5/2004 |
| WO | WO 2004/080996 A1 | 9/2004 |
| WO | WO 2004/091623 A1 | 10/2004 |
| WO | WO 2006/096626 A2 | 9/2006 |
| WO | WO 2006/127898 A2 | 11/2006 |
| WO | WO 2006/127899 A2 * | 11/2006 |
| WO | WO 2006/132963 A2 | 12/2006 |
| WO | WO 2006/135650 A1 | 12/2006 |
| WO | WO 2007/053194 A2 | 5/2007 |
| WO | WO 2007/053698 A2 | 5/2007 |
| WO | WO 2007/131154 A2 | 11/2007 |
| WO | WO 2008/016704 A1 | 2/2008 |
| WO | WO 2008/019115 A2 | 2/2008 |
| WO | WO 2008/064150 A1 | 5/2008 |
| WO | WO 2008/064351 A2 | 5/2008 |
| WO | WO 2008/064353 A2 | 5/2008 |
| WO | WO 2008/070462 A2 | 6/2008 |
| WO | WO 2008/121348 A2 | 10/2008 |
| WO | WO 2008/121352 A2 | 10/2008 |
| WO | WO 2008/121860 A1 | 10/2008 |

OTHER PUBLICATIONS

International Search Report and Written Opinion for PCT/US2008/004116 mailed Nov. 24, 2008.

International Preliminary Report on Patentability for PCT/US2008/004116 mailed Oct. 8, 2009.

[No Author Listed] Endogenous opioids. http://opioids.com/opiates.html. 3 pages, Nov. 2007.

(56) References Cited

OTHER PUBLICATIONS

[No Author Listed] Extracolonic Motility Abnormalities. Persistence of Abdominal Symptoms after Successful Surgery from Southern Medical Journal. 2002;95(9);1042-1046. http://www.medscape.com/viewarticle/442893_4. 2 pages.

[No Author Listed] Pathophysiology. Medscape General Medicine. 2005;7(3):17 http://www.medscape.com/viewarticle/506798_5. 3 pages.

[No Author Listed] Methylnaltrexone: MNTX. Drugs R D. 2006;7(6):374-8.

[No Author Listed] Oncology. 1996;10(12):1880.

[No Author Listed] Pain management; cancer-pain remedy wins orphan drug status. Cancer Biotechnology Weekly. Aug. 12, 1996. 2 pages.

[No Author Listed] Progenics achieves enrollment target in pivotal phase 3 clinical trial of methylnaltrexone for opioid-induced constipation. Press Release. Progenics Pharmaceuticals, Inc. Dec. 3, 2004.

[No Author Listes] Progenics announces positive top-line results from pivotal phase 3 clinical trial of MNTX in opioid-induced constipation. Press Release. Progenics Pharmaceuticals, Inc. Mar. 10, 2005.

[No Author Listed] Progenics initiates second phase 3 clinical trial of methylnaltrexone in opioid-induced constipation. Press Release. Progenics Pharmaceuticals, Inc. Jan. 13, 2004.

[No Author Listed] Remington's Pharmaceutical Sciences. 15$^{th}$ Edition. 1995: 201-02, 273-74, 278-79, 283-84, 1466, 1614-5.

[No Author Listed] The Merck Manual. 17$^{th}$ edition. 1999:312-315.

Akinbami et al., Effect of a peripheral and a central acting opioid antagonist on the testicular response to stress in rats. Neuroendocrinolohy. Apr. 1994;59(4):343-8.

Altier et al., Opioid receptors in the ventral tegmental area contribute to stress-induced analgesia in the formalin test for tonic pain. Brain Res. Apr. 29, 1996;718(1-2):203-6.

Amin et al., Efficacy of methylaltrexone versus naloxone for reversal of morphine-induces depression of hypoxic ventilatory response. Anesth Analg. Apr. 1994;78(4):701-5.

Amir et al., Endorphins in endotoxin-induced hyperglycemia in mice. Arch Toxicol Suppl. 1983;6:261-5.

Amir, Naloxone improves, and morphin exacerbates, experimental shock induced by release of endogenous histamine by compound 48/80. Brain Res. Apr. 9, 1984;297(1):187-90.

Arendt et al., Bidirectional effects of endogenous opioid peptides on endothelin release rates in porcine aortic endothelial cell culture: mediation by delta opioid receptor and opioid receptor antagonist-insensitive mechanisms. J Pharmacol Exp Ther. Jan. 1995;272(1):1-7.

Arerangaiah et al., Opioids induce renal abnormalities in tumor-bearing mice. Nephron Exp Nephrol. 2007;105(3):e80-9. Epub Jan. 12, 2007.

Argnentieri et al., Interaction of the opiate antagonist, naltrexone methyl bromide, with the acetylcholine receptor system of the motor end-plate. Brain Res. Oct. 31, 1983;277(2):377-9.

Armstead, Relationship among NO, the KATP channel, and opioids in hypoxic pial artery dilation. Am J Physiol. Sep. 1998;275(3 Pt 2):H988-94.

Armstrong et al., The gastrointestinal activity and peripheral selectivity of alvimopan, ADL08-0011, and naloxone in mice. May 21, 2006 DDW Presentation in Los Angeles. Clincal Phar Therap. 2005;77:74. Abstract #221957.

Attali et al., Kappa opiate agonists inhibit Ca2+ influx in rat spinal cord-dorsal root ganglion cocultures. Involvement of a GTP-binding protein. J Biol Chem. Jan. 5, 1989;264(1):347-53.

Aung et al., Methylnaltrexone prevents morphine-induced kaolin intake in the rat. Life Sci. Apr. 16, 2004;74(22):2685-91.

Aung et al., Scutellaria baicalensis decreases ritonavir-induced nausea. AIDS Res Ther. Dec. 20, 2005;2:12.

Bagnol et al., Changes in enkephalin immunoreactivity of sympathetic ganglia and digestive tract of the cat after splanchnic nerve ligation. Regul Pept. Sep. 22, 1993;47(3):259-73. Abstract Only.

Baker et al., Functional effects of systemically administered agonists and antagonists of mu, delta, and kappa opioid receptor subtypes on body temperature in mice. J Pharmacol Exp Ther. Sep. 2002;302(3):1253-64.

Balasubramanian et al., Morphine sulfate inhibits hypoxia-induced vascular endothelial growth factor expression in endothelial cells and cardiac myocytes. J Mol Cell Cardiol. Dec. 2001;33(12):2179-87.

Baratti et al., Brain opioid peptides may participate in the reversal of pentylenetetrazol-induced amnesia. Methods Find Exp Clin Pharmacol. Sep. 1990;12(7):451-6.

Basilisco et al., Oral naloxone antagonizes loperamide-induced delay of orocecal transit. Dig Dis Sci. Aug. 1987;32(8):829-32.

Basilisco et al., Effect of loperamide and naloxone on mouth-to-caecum transit time evaluated by latulose hydrogen breath test. Gut. Jul. 1985;26(7):700-3.

Bedingfield et al., Methylnatrexone attenuates taste aversion conditioned by low-dose ethanol. Alcohol. Jan. 1998;15(1):51-4.

Belcheva et al., μ-Opioid receptor-mediated ERK activation involves calmodulin-dependent epidermal growth factor receptor transactivation. J Biol Chem. Sep. 7, 2001;276(36):33847-53. Epub Jul. 16, 2001.

Belcheva et al., μ opioid transactivation and down-regulation of the epidermal growth factor receptor in astrocytes: imploications for mitogen-activated protein kinase signaling. Mol Pharmacol. Dec. 2003;64(6):1391-401.

Bianchetti et al., Quaternary derivatives of narcotic antagonists: stereochemical requirements at the chiral nitrogen for in vitro and in vivo activity. Life Sci. 1983;33 Suppl 1:415-8.

Bianchi et al., Quaternary narcotic antagonists' relative ability to prevent antinociception and gastrointestinal transit inhibition in morphine-treated rats as an index of peripheral selectivity, Life Sci. May 31, 1982;30(22):1875-83.

Bickel, Stimulation of colonic motility in dogs and rats by an enkephalin analogue pentapeptide. Life Sci. 1983;33 Suppl 1:469-72.

Bigliardi et al., Different expression of mu-opiate receptor in chronic and acute wounds and the effect of beta-endorphin on transforming growth factor beta type II receptor and cytokeratin 16 expression. J Invest Dermatol. Jan. 2003;120(1):145-52.

Bigliardi-Qi et al., Changes of epidermal mu-opiate receptor expression and nerve endings in chronic atopic dermatitis. Dermatology. 2005;210(2):91-9.

Binder et al., Effect of the peripherally selective kappa-opioid agonist, asimadoline, on adjuvant arthritis. Br J Pahrmacol. Jun. 1998;124(4):647-54.

Blank et al., Central, stereoselective receptors mediate the acute effects of opiate antagonists on luteinizing hormone secretion. Life Sci. Oct. 27, 1986;39(17):1493-99.

Blebea et al., Differential effects of vascular growth factors on arterial and venous angiogenesis. J Vasc Surg. Mar. 2002;35(3):532-8.

Blebea et al., Opioid growth factor modulates angiogenesis. J Vasc Surg. Aug. 2000;32(2):364-73.

Bond et al., Investigation of small bowel transit time in man utilizing pulmonary hydrogen (H2) measurements. J Lab Clin Med. Apr. 1975;85(4):546-55. Abstract Only.

Bonn, Morphine stimulates tumour growth. Lancet Oncol. Sep. 2002;3(9):520.

Boonstra et al., Engineering novel biocatalytic routes for production of semisynthetic opiate drugs. Biomol Eng. Sep. 2001;18(2):41-7.

Bös et al., A Short and Efficient Synthesis of C-Nor-Dihydrocodeinone—The Antipode of Goto's Sinomenilone. Heterocycles. 1983;20(6):1077-81.

Bowen et al., Antagonism of the antinociceptive and discriminative stimulus effects of heroin and morphine by 3-methoxynaltrexone and naltrexone in rhesus monkeys. J Pharmacol Exp Ther. Jul. 2002;302(1):264-73.

Bowen et al., Behavioral Pharmacology of Opioid Antagonists with Limited Access Across the Blood-Brain Barrier. College on Problems of Drug Dependence 64$^{th}$ Annual Scientific Meeting. Jun. 8-13, 2002. Quebec City, Quebec, Canada. Abstracts. Drug Alcohol Depend. May 1, 2002;66 Suppl 1:S1-220, Abstract No. 65.

Breitbart et al., Control of non-pain symptoms in HIV/AIDS. J Back Musculoskelet Rehabil. 1997;8(3):243-46.

(56) References Cited

OTHER PUBLICATIONS

Brix-Christensen et al., Endogenous morphine is produced in response to cardiopulmonary bypass in neonatal pigs. Acta Anaesthesiol Scand. Nov. 2000;44(10):1204-8.
Brix-Christensen et al., Endogenous morphine levels increase following cardiac surgery as part of the nti-inflammatory response? Int J Cardiol. Dec. 19, 1997;62(3):191-7.
Brondsted et al., Hydrogels for site-specific drug delivery to the colon: in vitro and in vivo degradation. Pharm Res. Dec. 1992;9(12):1540-5. Abstract Only.
Brown et al., Opiate antagonists: central sites of action in suppressing water intake of the rat. Brain Res. Sep. 28, 1981;221(2):432-6.
Brown et al., Reversal of morphine-induced catalepsy in the rat by narcotic antagonists and their quaternary derivatives. Neuropharmacology. Mar. 1983;22(3):317-21.
Brown et al., Techniques for mechanical stimulation of cells in vitro: a review. J Biomech. Jan. 2000;33(1):3-14.
Brown et al., The use of quaternary narcotic antagonists in opiate research. Neuropharmacology. Mar. 1985;24(3):181-91.
Bruce et al., Microbial degradation of the morphine alkaloids: identification of morphine as an intermediate in the metabolism of morphine by Pseudomonas putida M10. Arch Microbiol. 1990;154(5):465-70.
Bruley-Des-Varannes et al., Cholécystokine et ses anatagonistes: effets sur la motricité digestive. Gastroenterol Clin Biol. 1991;15:744-57. French.
Bundgaard et al., (C) Means to Enhance Penetration. (1) Prodrugs as a means to improve the delivery of peptide drugs. J Drug Delivery Rev. 1992;8:1-38.
Burkhart et al., Metkephamid (Tyr-D-Ala-Gly-Phe-N(Me)Met-$NH_2$), a Potent Opioid Peptide: Receptor Binding and Analgesic Properties. Peptides. 1982;3:869-71.
Caballero-Hernandez et al, Potentiation of rat lymphocyte proliferation by novel non-peptidic synthetic opioids. Int Immunopharmacol. Jul. 2005;5(7-8):1271-8. Epub Apr. 12, 2005.
Cadet et al., Differential expression of the human mu opiate receptor from different primary vascular endothelial cells. Med Sci Monit. Oct. 2004;10(10):BR351-5. Epub Sep. 23, 2004.
Cadet et al., Molecular identification and functional expression of mu 3, a novel alternatively spliced variant of the human mu opiate receptor gene. J Immunol. May 15, 2003;170(10):5118-23.
Calcagnetti et al., Quaternary naltrexone reveals the central mediation of conditional opioid analgesia. Pharmacol Biochem Behav. Jul. 1987;27(3):529-31.
Cao et al., Cardioprotection of interleukin-2 is mediated via kappa-opioid receptors. J Pharmacol Exp Ther. May 2004;309(2):560-7. Epub Jan. 27, 2004.
Carmeliet et al., Angiogenesis in cancer and other diseases. Nature. Sep. 14, 2000;407(6801):249-57.
Carr et al., Naltrexone antagonizes the analgesic and immunosuppressive effects of morphine in mice. J Pharmacol Exp Ther. May 1994;269(2):693-8.
Chang et al., An antiabsorptive basis for precipitated withdrawal diarrhea in morphine-dependent rats. J Pharmacol Exp Ther. Feb. 1984;228(2):364-9.
Chang et al., The association between opiates and cytokines in disease. Adv Exp Med Biol. 1998;437:4-6.
Chatterjie et al., Stereospecific synthesis of the 6beta-hydroxy metabolites of naltrexone and naloxone. J Med Chem. May 1975;18(5):490-2. Abstract Only.
Chen et al., Morphine stimulates vascular endothelial growth factor-like signaling in mouse retinal endothelial cells. Curr Neurovasc Res. Aug. 2006;3(3):171-80.
Choi et al., Opioid antagonists: a review of their role in palliative care, focusing on use in opioid-related constipation. J Pain Symptom Manage. Jul. 2002;24(1):71-90. Review.
Choi et al., Inhibition of chemokine-induced chemotaxis of monkey luekocytes by mu-opioid receptor agonists. In Vivo. Sep.-Oct. 1999;13(5):389-96.

Collins et al., Peak plasma concentrations after oral morphine: a systemic review. J Pain Symptom Manage. Dec. 1998;16(6):388-402.
Cone et al., The identification and measurement of two metabolites of naltrexone in human urine. Res Commun Chem Pathol Pharmacol. Jun. 1978;20(3):413-33. Abstract Only.
Cozzolino et al., Acute effects of beta-endorphin cardiovascular function in patients with mild to moderate chronic heart failure. Am Heart J. Sep. 2004;148(3):E1-7.
Culpepper-Morgan et al., Treatment of opioid-induced constipation with oral naloxone: a pilot study. Clin Pharmacol Ther. Jul. 1992;52(1):90-5. Abstract Only.
D'Amato et al., Studies of three non-peptide cholecystokinin antagonists (devazepide, lorglumide and loxiglumide) in human isolated alimentary muscle and guinea-pig ileum. Br J Pharmacol. Feb. 1991;102(2):391-5.
Dajani et al., Effects of E prostaglandins, diphenoxylate and morphine on intestinal motility in vivo. Eur J Pharmacol. Nov. 1975;34(1):105-13. Abstract Only.
Dajani et al., The pharmacolohy of SC-27166: a novel antidiarrheal agent. J Pharmacol Exp Ther. Dec. 1977;203(3):512-26. Abstract Only.
Daniel et al., Effects of morphine and other drugs on motility of the terminal ileum. Gastroenterology. Apr. 1959;36(4):510-23.
De Ponti et al., Methylnaltrexone Progenics. Curr Opin Investig Drugs. Apr. 2002;3(4):614-20. Review.
De Schryver et al., New developments in the treatment of irritable bowel syndrome. Scand J Gastroenterol Suppl. 2000;(232):38-42. Review.
Doherty et al., Route-dependent metabolism of morphine in the vascularly perfused rat small intestine preparation. Pharm Res. Mar. 2000;17(3):291-8.
Dragonetti et al., Levallorphan methyl iodide (SR 58002), a potent narcotic antagonist with peripheral selectivity superior to that of other quaternary compounds. Life Sci. 1983;33 Suppl 1:477-80.
Egan et al., Prospective pharmacokinetic and pharmacodynamic validation of propofol's context sensitive T1/2. Anesthesiology. Sep. 1999;91(3A): Abstract A347.
Eisenberg, Effects of naltrexone on plasma corticosterone in opiate-naïve rats: a central action. Life Sci. Mar. 19, 1984;34(12):1185-91.
Eisenstein et al., Effect of opioids on oral *Salmonella* infection and immune function. Adv Exp Med Biol. 2001;493:169-76.
Epstein et al., Naltrexone attenuates acute cigarette smoking behavior. Pharmacol Biochem Behav. Jan. 2004;77(1):29-37.
Farooqui et al., µ opioid receptor stimulates a growth promoting and pro-angiogenic tumor microenvironment. Proc Amer Assoc Cancer Res. 2005;46. AACR Meeting Abstract, Abstract #4650.
Farooqui et al., Naloxone acts as an antagonist of estrogen receptor activity in MCF-7 cells. Mol Cancer Ther. Mar. 2006;5(3):611-20.
Farthing et al., New drugs in the management of the irritable bowel syndrome. Drugs. Jul. 1998;56(1):11-21.
Farup et al., The Symptomatic Effect of Cisapride in Patients with Irritable Bowel Syndrome and Constipation. Scand J Gastroenterol. 1998;33:28-31.
Faura et al., Systematic review of factors affecting the ratios of morphine and its major metabolites. Pain. Jan. 1998;74(1):43-53.
Fecho et al., Assessment of the involvement of central nervous system and peripheral opioid receptors in the immunomodulatory effect of acute morphine treatment in rats. J Pharmacol Exp Ther. Feb. 1996;276(2):626-36.
Fernandez-Tome et al., Interaction between opioid agonists or naloxone and 5-HTP on feeding behavior in food-deprived rats. Pharmacol Biochem Behav. Feb. 1988;29(2):387-92.
Fingl, Chapter 43: Laxatives and cathartics. In Pharmacological Basis of Therapeutics. 1980:1002-12.
Finn et al., Endocytosis of the mu opioid receptor reduces tolerance and a cellular hallmark of opiate withdrawal. Neuron. Dec. 6, 2001;32(5):829-39.
Flores et al., Mechanisms of morphine-induced immunosuppression: effect of acute morphine administration on lymphocyte trafficking. J Pharmacol Exp Ther. Mar. 1995;272(3):1246-51.
Foss, A review of the potential role of methylnaltrexone in opioid bowel dysfunction. Am J Surg. Nov. 2001;182(5A Suppl):19S-26S.

(56) References Cited

OTHER PUBLICATIONS

Foss et al., Alvimopan (Entereg™), a novel opioid antagonist, achieves active systemic concentrations. Amer Soc Clin Pharma Ther. 2005:74. Abstract P11-90.

Foss et al., Dose-related antagonism of the emetic effect of morphine by methylnaltrexone in dogs. J Clin Pharmacol. Aug. 1993;33(8):747-51.

Foss et al., Effects of methylnaltrexone on morphine-induced cough suppression in guinea pigs. Life Sci. 1996;59(15):PL235-8.

Foss et al., Enteric-coated methylnaltrexone prevents opioid-induced oral-cecal transit delay in humans. Anesth Analg. 2000;90. Abstract S409.

Foss et al., Methylnaltrexone does not antagonize the analgesic effect of morphine: a clinical study. 1995 Annual scientific meeting of the American Society of Anesthesiologists. Atlanta, Georgia, Oct. 21-25, 1995. Abstracts, Anesthesiology. Sep. 1995;83(3A Suppl):A361.

Foss et al., Methylnaltrexone reduces morphine-induced postoperative emesis by 30%. Anesth Analg. 1994;78:S119.

Foss et al., Prevention of apomorphine- or cisplatin-inuced emesis in the dog by a combination of methylnatrexone and morphine. Cancer Chemother Pharmacol. 1998;42(4):287-91.

Foss et al., Safety and tolerance of methylnaltrexone in healthy humans: a randomized, placebo-controlled, intravenous, ascending-dose, pharmacokinetic study. J Clin Pharmacol. Jan. 1997;37(1):25-30.

Foss et al., Subcutaneous methylnaltrexone reduces morphine-induced subjective effects in humans. Anesthesiology. 2001;95. Abstract A-817.

Foss et al., The efficacy or oral methylnaltrexone in decreasing the subjective effects of IV morphine. Anesth Analg. 1997;84. Abstract S484.

France et al., Comparison of naltrexone and quaternary naltrexone after systemic and intracerebroventricular administration in pigeons. Neuropharmacology. Jun. 1987;26(6):541-8.

France et al., Intracerebroventricular drug administration in pigeons. Pharmacol Biochem Behav. Nov. 1985;23(5):731-6.

France et al., Morphine, saline and naltrexone discrimination in morphine-treated pigeons. J Pharm and Exper Ther. 1987;242:195-202.

Fraser et al., Methods for evaluating addiction liability. (A) "Attitude" of opiate addicts toward opiate-like drugs. (B) a short-term "direct" addiction test. J Pharmacol Exp Ther. Sep. 1961;133:371-87. Abstract Only.

Frässdorf et al., Morphine induces late cardioprotection in rat hearts in vivo: the involvement of opioid receptors and nuclear transcription factor kappaB. Anesth Analg. Oct. 2005;101(4):934-41.

Frederickson et al., Metkephamid, a Systemically Active Analog of Methionine Enkephalin with Potent Opioid δ-Receptor Activity. Science. 1991;211:603-05.

French et al., Purification and characterization of morphine reductase from Pseudomonas putida M10. Biochem J. Jul. 1, 1994;301 (Pt 1):97-103.

Friedman et al., Opioid antagonists in the treatment of opioid-induced constipation and pruritus. Ann Pharmacother. Jan. 2001;35(1):85-91.

Funke et al., A proton and carbon-13 nuclear magnetic resonance study of three quaternary salts of naloxone and oxymorphone. J Chem Soc. 1986:735-8.

Galligan et al., Centrally mediated inhibition of small intestinal transit and motility by morphine in the rat. J Pharmacol Exp Ther. Aug. 1983;226(2):356-61. Abstract Only.

Gan et al., Consensus guidelines for managing postoperative nausea and vomiting. Anesth Analg. Jul. 2003;97(1):62-71. Review.

Gervitz, Targeted approach: methylnaltrexone blocks opioid-induced constipation and other peripheral side effects. Topics in Pain Management. 2005;21(1):6-8. Quiz on p. 11.

Giles et al., Quaternary opiate antagonists lower blood pressure and inhibit leucine-enkephalin responses. Eur J Pharmacol. Nov. 25, 1983;95(3-4):247-52.

Gmerek et al., Independent central and peripheral mediation of morphine-induced inhibition of gastrointestinal transit in rats. J Pharmacol Exp Ther. Jan. 1986;236(1):8-13.

Goumon et al., Ascaris suum, an intestinal parasite, produces morphine. J Immunol. Jul 1, 2000;165(1):339-43.

Green, Comparative effects of analgesics on pain threshold, respiratory frequency and gastrointestinal propulsion. Br J Pharmacol Chemother. Mar. 1959;14(1):26-34.

Grigoriev et al., Clinical gastroenterology. Ministry of Health of the Russian Federation. Russian State Medical University. 2001;491-492. Russian.

Gupta et al., Angiogenesis: a curse or a cure? Postgrad Med J. Apr. 2005;81(954):236-42.

Gupta et al., Morphine exaggerates retinopathy in transgenic sickle mice. Blood (ASH Annual Meeting Abstract) 106: Abstract 209.

Gupta et al., Morphine mimics VEGF in vascular endothelium by promoting pro-angiogenic and survival promoting signaling and angiogenesis. FASEB Journal. 2002;16(4):A207. Abstract #182.12.

Gupta et al., Morphine stimulates angiogenesis by activating proangiogenic and survival-promoting signaling and promotes breast tumor growth. Cancer Res. Aug. 1, 2002;62(15):4491-8.

Gutstein et al., Role of inositol 1,4,5-trisphosphate receptors in regulating apoptotic signaling and heart failure. Heart Vessels. 1997;Suppl 12:53-7.

Guy et al., Chapter 1. Structural models fo $Na^+$, $Ca^{2+}$, and $K^+$ channels. In: Ion Channels and Genetic Diseases. Dawson et al., eds. 1995:1-28.

Hailes et al., Biological synthesis of the analgesic hydromorphone, an intermediate in the metabolism of morphine, by Pseudomonas putida M10. Appl. Environ Microbiol. Jul. 1993;59(7):2166-70.

Hanif et al., Hypotensive effect of novel chimeric peptides of met-enkephalin and FMRFa. Regul Pept. Feb. 15, 2005;125(1-3):155-61.

He et al., Improvement of Bowel Dysfunction Caused by Opioid Analgesics: Research Advances on Methylnaltrexone. Chinese Journal of Clinical Rehabilitation. 2002;6(20):3104-05.

Hein et al., Pharmacological analysis of the discriminative stimulus characteristics of ethylketazocine in the rhesus monkey. J Pharmacol Exp Ther. Jul. 1981;218(1):7-15.

Hicks et al., Differential effects of the novel non-peptidic opioid 4-tyrosylamido-6-benzyl-1,2,3,4 tetrahydroquinoline (CGPM-9) on in vitro rat t lymphocyte and macrophage functions. Life Sci. May 4, 2001;68(24):2685-94.

Hirota et al., Loss of a gp130 cardiac muscle cell survival pathway is a critical event in the onset of heart failure during biomechanical stress. Cell. Apr. 16, 1999;97(2):189-98.

Ho et al., Beta-endorphin: peripheral opioid activity of homologues from six species. Int J Pept Protein Res. Apr. 1987;29(4):521-4.

Ho et al., Methylnaltrexone antagonizes opioid-mediated enhancement of HIV infection of human blood mononuclear phagocytes. J Pharmacol Exp Ther. Dec. 2003;307(3):1158-62. Epub Oct. 14, 2003.

Ho et al., Suppression of immunological functions in morphine addicted mice. NIDA Res Monogr. 1986;75:599-602.

Hoffmann et al., [Calcium in the prevention of stress ulcer in the rat] Langenbecks Arch Chir. 1976;Suppl:228-32. German.

Hoffmann et al., Hypocalcemia during restraint stress in rats. Indication that gastric ulcer prophylaxis by exogenous calcium interferes with calcitonin release. Res Exp Med (Berl). May 30, 1979;175(2):159-68.

Hou et al., A mu-receptor opioid agonist induces AP-1 and NF-kappa B transcription factor activity in primary cultures of rat cortical neurons. Neurosci Lett. Jul. 19, 1996;212(3):159-62.

Howd et al., Naloxone and intestinal motility. Experientia. Oct. 15, 1978;34(10):1310-1.

Hussain et al., Improvement of the oral bioavailability of naltrexone in dogs: a prodrug approach. J Pharm Sci. May 1987;76(5):356-8.

Hussain et al., Naltrexone-3-salicylate (a prodrug of naltrexone): synthesis and pharmacokinetics in dogs. Pharm Res. Feb. 1988;5(2):113-5.

Hutchinson et al., Assessment in the guinea-pig ileum and mouse vas deferens of benzomorphans which have strong antinociceptive activity but do not substitute for morphine in the dependent monkey. Br J Pharmacol. Dec. 1975;55(4):541-6.

(56) References Cited

OTHER PUBLICATIONS

Hutchinson et al., Scintigraphic measurment of ileocaecal transit in irritable bowel syndrome and chronic idipathic constipation. Gut. Apr. 1995;36(4):585-9.
Iorio et al., Diastereoisomeric Quaternary Morphinium Salts: Synthesis, Stereochemistry and Analgesic Properties. European Journal of Medicinal Chemistry. 1984;19(1):11-16.
Iorio et al., Narcotic agonist/antagonist properties of quaternary diastereoisomers derived from oxymorphone and naloxone. Eur J Med Chem. 1984;19(4):301-3.
Jalowiec et al., Suppression of juvenile social behavior requires antagonism of central opioid systems. Pharmacol Biochem Behav. Jul. 1989;33(3):697-700.
Jankovic et al., Quaternary naltrexone: its immunomodulatory activity and interaction with brain delta and kappa opioid receptors. Immunopharmacology. Sep.-Oct. 1994;28(2):105-12.
Jasinski, Assessment of the Abuse Potentiality of Morphinelike Drugs (Methods Used in Man). Drug Addiction J. 1997:197-258.
Jasinski, Tolerance and Dependence to opiates. Acta Anaesthesiol Scand. Jan. 1997;41(1 Pt 2):184-6.
Jenab et al., Ethanol and naloxone differentially upregulate delta opioid receptor gene expression in neuroblastoma hybrid (NG108-15) cells. Brain Res Mol Bran Res. Nov. 1994;27(1):95-102.
Johnson et al., Stability of tacrolimus with morphine sulfate, hydromorphone hydrochloride, and ceftazidime during simulated intravenous coadministration. Am J Health Syst Pharm. Jan. 15, 1999;56(2):164-9.
Kakeji et al., Preclinical studies of the combination of angiogenic inhibitors with cytotoxis agents. Invest New Drugs. 1997;15(1):39-48.
Kasamatsu et al., Attenuation of aortic baroreflex responses by microinjections of endomorphin-2 into the rostral ventrolateral medullary pressor area of the rat. Am J Physiol Regul Integr Comp Physiol. Jul. 2005;289(1):R59-67. Epub Feb. 17, 2005.
Kaufman et al., Role of opiate receptors in the regulation of colonic transit. Gastroenterology. Jun. 1988;94(6):1351-6.
Kehlet et al., Review of postoperative ileus. Am J Surg. Nov. 2001;182(5A Suppl):3S-10S. Review.
Keith et al., Failure of naloxone to prevent the emetic activity of apomorphine in dogs. J Vet Pharmacol Ther. Dec. 1981;4(4):315-6.
Kim et al., Assay for methylnaltrexone in rat brain regions and serum by high-performance liquid chromatography with coulometric electrochemical detection. Chromatographia. Oct. 1989;28(7-8):359-63.
King et al., Hypothalamic-pituitary-adrenocortical (HPA) axis response and biotransformation of oral naltrexone: preliminary examination of relationship to family history of alcoholism. Neuropsychopharmacology. Jun. 2002;26(6):778-88.
Kinsman et al., Effect of naloxone on feedback regulation of small bowel transit by fat. Gastroenterology. Aug. 1984;87(2):335-7.
Knowles et al., Slow transit constipation: a model of human gut dysmotility. Review of possible aetiologies. Neurogastroenterol Motil. Apr. 2000;12(2):181-96.
Koblish et al., Behavioral profile of ADL 8-2698, a novel GI-restricted μ opioid receptor antagonist. Society for Neuroscience Abstracts. 2001;27(2):2407. Abstract Only.
Kobylecki et al., N-Methylnalorphine: definition of N-allyl conformation for antagonism at the opiate receptor. J Med Chem. Nov. 1982;25(11):1278-80.
Koch et al., Inhibitory neuropeptides and intrinsic inhibitory innervation of descending human colon. Dig Dis Sci. Jun. 1991;36(6):712-8. Abstract Only.
Koczka et al., Selective Quaternization of Compounds with Morphine Skeleton. Acta Chimica Academica Scien Hung. 1967;51(4):393-402.
Kodani et al., Delta-opioid receptor-induced late preconditioning is mediated by cyclooxygenase-2 in conscious rabbits. Am J Physiol Heart Circ Physiol. Nov. 2002;283(5):H1943-57.
Koob et al., Effects of opiate antagonists and their quaternary derivatives on heroin self-administration in the rat. J Pharmacol Exp Ther. May 1984;229(2):481-6.

Kosten et al., Naltrexone and morphine alter the discrimination and plasma levels of ethanol. Behav Pharmacol. Feb. 1999;10(1):1-13.
Kostic, CAS Abstract Document No. 127: 13345, 1997.
Kotake et al., Variations in demethylation of N-methylnaltrexone in mice, rats, dogs, and humans. Xenobiotica. Nov. 1989;19(11):1247-54.
Kratzel et al., An Efficient Synthesis of 14-Halogenomethyl-Substituted C-Normorphinans. Heterocycles. 1987;26(10):2703-10.
Kratzel et al., Synthesis of 5a,11b-Propanonaphthol[1,2-e][1,2]oxazepines as Potential Opioid Analgesics. J Chem Soc Perkin 1. 1994;11:1541-43.
Kromer et al., Endogenous opioids, the enteric nervous system and gut motility. Dig Dis. 1990;8(6):361-73.
Kromer et al., The current status of opioid research on gastrointestinal motility. Life Sci. 1989;44(9):579-89.
Law et al., Agonist activation of delta-opioid receptor but not mu-opioid receptor potentiates fetal calf serum or tyrosine kinase receptor-mediated cell proliferation in a cell-line-specific manner. Mol Pharmacol. Jan. 1997;51(1):152-60.
Law et al., Properties of delta opioid receptor in neuroblastoma NS20Y: receptor activation and neuroblastoma proliferation. J Pharmacol Exp Ther. Jan. 1995;272(1):322-32.
Law et al., Regulation of opioid receptor activities. J Pharmacol Exp Ther. May 1999;289(2):607-24.
Lazar et al., Synthesis and biological activity of the phosphate and sulfate esters of naloxone and naltrexone. Eur J Med Chem. 1994;29:45-53.
Leander, A kappa opioid effect: increased urination in the rat. J Pharmacol Exp Ther. Jan. 1983;224(1):89-94.
Li et al., Methadone enhances human immunodeficiency virus infection of human immune cells. J Infect Dis. Jan. 1, 2002;185(1):118-22. Epub Dec. 14, 2001.
Lim et al., Morphine preconditions Purkinje cells against cell death under in vitro simulated ischemia-reperfusion conditions. Anesthesiology. Mar. 2004;100(3):562-8.
Linn et al., Peripherally restricted μ-opioid receptor antagonists: a review. Tech Reg Anesth Pain Manag. Jul. 2007;11(1):27-32.
Little, et al., ADL 8-2698, a GI restricted opioid antagonist, blocks the antisecretory and colorectal transit effects of morphine and loperamide. Society for Neuroscience Abstracts. 2001;27(2):2407. Abstract Only.
Livingston et al., Postoperative ileus. Dig Dis Sci. Jan. 1990;35(1):121-32.
Lopez et al., Demonstration of long-lasting blockade of experimental ileus in rats by an opioid k-agonist. Gastroenterology. 1995;108(4):Abstract A640.
Lydon et al., Intravenous methylnaltrexone attenuates intrathecal morphine induced delayed gastric emptying in rats. ESA Free Paper Prize Competition. Eur J Anaesthesiol. Apr. 2001;18 Suppl 21:92. Abstract A-327.
Lysle et al., Evidence for the involvement of the caudal region of the periaqueductal gray in a subset of morphine-induced alterations of immune status. J Pharmacol Exp Ther. Jun. 1996;277(3):1533-40.
Lysle et al., Modulation of immune status by a conditioned aversive stimulus: evidence for the involvement of endogenous opioids. Brain Behav Immun. Jun. 1992;6(2):179-88.
Machelska et al., Selectins and integrins but not platelet-endothelial cell adhesion molecule-1 regulate opioid inhibition of inflammatory pain. Br J Pharmacol. Jun. 2004;142(4):772-80. Epub May 24, 2004.
Mack, Paralytic ileus: response to naloxone. Br J Surg. Oct. 1989;76(10):1101.
Magazine et al., Morphine-induced conformational changes in human monocytes, granulocytes, and endothelial cells and in invertebrate immunocytes and microglia are mediated by nitric oxide. J Immunol. Jun. 15, 1996;156(12):4845-50.
Magnan et al., The binding spectrum of narcotic analgesic drugs with different agonist and antagonist properties. Naunyn Schmiedebergs Arch Pharmacol. Jun. 1982;319(3):197-205.
Maguire et al., Pharmacological profiles of fentanyl analogs at mu, delta and kappa opiate receptors. Eur J Pharmacol. Mar. 24, 1992;213(2):219-25. Abstract Only.
Malspeis et al., Metabolic Reduction of Naltrexon I. Synthesis, Separation and Characterization of Naloxone and Maltrexone Reduction

(56) References Cited

OTHER PUBLICATIONS

Products and Qualitative Assay of Urine and Bile Following Adminstration of Naltrexone, α-naltrexol, or β-naltrexol. Chem Pathol Pharmacol. 1975;12(1):43-65.

Manara et al., Inhibition of gastrointestinal transit by morphine in rats results primarily from direct drug action on gut opioid sites. J Pharmacol Exp Ther. Jun. 1986;237(3):945-9. Abstract Only.

Manara et al., Peripheral selectivity of quaternary narcotic antagonists: relative ability to prevent gastrointestinal transit inhibition and antinociception in morphinized rats. Adv. Endog. Exog. Opioids, Poroc. Int. Narc. Res. Conf., 12th (1981): 402-4.

Manara et al., The central and peripheral influences of opioids on gastrointestinal propulsion. Annu Rev Pharmacol Toxicol. 1985;25:249-73.

Mančev et al., The immunomodulating effects of specific opioid receptor antagonists after their intracerebroventricular application. Intl J Thymol. 1999;7(12-13):589-95.

Marmor et al., Coronary artery disease and opioid use. Am J Cardiol. May 15, 2004;93(10):1295-7.

McBride et al., delta2 opioid receptor agonist facilitates mean arterial pressure recovery after hemorrhage in conscious rats. Shock. Mar. 2005;23(3):264-8.

McCance-Katz et al., Interactions between buprenorphine and antiretrovirals. II. The protease inhibitors nelfinavir, lopinavir/ritonavir, and ritonavir. Clin Infect Dis. Dec. 15, 2006;43 Suppl 4:S235-46.

McCarthy et al., Opioids, opioid receptors, and the immune response. Drug Alcohol Depend. Apr. 1, 2001;62(2):111-23.

McCarthy et al., Preliminary studies on the use of plasma β-endorphin in horses as an indicator of stress and pain. J Equine Vet Sci. 1993;13(4):216-9.

McQuay et al., Opioid problems and morphine metabolism and excretion. http://www.medicine.ox.ac.uk/bandolier/booth/painpag/wisdom/c14.html. Last accessed Feb. 8, 2010. 24 pages.

McQuay, Opioid use in chronic pain. Acta Anaesthesiol Scand. Jan. 1997;41(1 Pt 2):175-83.

Mellon et al., Evidence for central opioid receptors in the immunomodulatory effects of morphine: review of potential mechanism(s) of action. J Neuroimmunol. Mar. 15, 1998;83(1-2):19-28.

Melzig et al., Stimulation of endothelial angiotensin-converting enzyme by morphine via non-opioid receptor mediated processes. Pharmazie. Sep. 1998;53(9):634-7.

Mickley et al., Quaternary naltrexone reverses morphine-induced behaviors. Physiol Behav. Aug. 1985;35(2):249-53.

Miedema et al., Methods for decreasing postoperative gut dysmotility. Lancet Oncol. Jun. 2003;4(6):365-72.

Misra et al., Intravenous kinetics and metabolism of [15,16-3H]naltrexonium methiodide in the rat. J Pharm Pharmacol. Mar. 1987;39(3):225-7.

Miyagi et al., Morphine induces gene expression of CCR5 in human CEMx174 lymphocytes. J Biol Chem. Oct. 6, 2000;275(40):31305-10.

Moerman et al., Evaluation of methylnaltrexone for the reduction of postoperative vomiting and nausea incidences. Acta Anaesthesiol Belg. 1995;46(3-4):127-32.

Moss, et al., Selective postoperative inhibition of gastrointestinal opioid receptors. N. Engl. J. Med. 2002;346(6):455.

Moss et al., Methylnaltrexone prevents morphine-induced CCR5 receptor expression. Anesthesiology. 2003;99. Abstract A-961.

Moss et al., Opioid-induced changes in pulmonary barrier integrity may explain heroid-induced pulmonary edema. American Society of Anesthesiologists presentation, Oct. 17, 2007 in San Francisco, CA. Abstract A1980.

Moss et al., Pain relief without side effects: peripheral opiate antagonists. 33rd ASA Refresher Courses in Anesthesiology, Philadelphia, Lippincott Williams * Wilkins, Schwartz, A.J. editor. 2006;33:175-86.

Mucha, Is the motivational effect of opiate withdrawal reflected by common somatic indices of precipitated withdrawal? A place conditioning study in the rat. Brain Res. Aug. 25, 1987;418(2):214-20.

Mucha, Tatse aversion involving central opioid antagonism is potentiated in morphine-dependent rats. Life Sci. 1989;45(8):671-8.

Murphy et al., Pharmaconkinetic of epidural administered methylnaltrexone a novel peripheral opioid antagonist. American Society of Anesthesiologists, 1999 annual meeting. Dallas, Texas, USA. Oct. 9-13, 1999. Anesthesiology. Sep. 1999;91(3A Suppl):A349.

Murphy et al., Opioid antagonist modulation of ischaemia-induced ventricular arrhythmias: a peripheral mechanism. J Cardiovasc Pharmacol. Jan. 1999;33(1):122-5.

Murphy et al., Opioid-induced delay in gastric emptying: a peripheral mechanism in humans. Anesthesiology. Oct. 1997;87(4):765-70.

Murphy et al., Pharmacokinetic profile of epidurally administered methylnaltrexone, a novel peripheral opioid antagonist in a rabbit model. Br J Anaesth. Jan. 2001;86(1):120-2.

Nair et al., Morphine Modulates the Expression of Chemokines and their Receptors by Peripheral Blood Mononuclear Cells (PBMC) from Normal Donors. J Allergy Clin Immunol. 1998:101(1):S57. Abstract 244.

Naranjo et al., Evidence for a central but not adrenal, opioid mediation in hypertension induced by brief isolation in the rat. Life Sci. May 26, 1986;38(21):1923-30.

Nelson, Morphine modulation of the contact hypersensitivity response: A pharmacological and immunological characterization. University of North Carolina at Chapel Hill. Dissertation Abstracts International. 2001;62/03-B:1635. 94 pages. Abstract Only.

Nelson et al., Involvement of central mu- but not delta- or kappa-opioid receptors in immunomodulation. Brain Behav Immun. Sep. 2000;14(3):170-84.

Nemeth-Lefkowitz et al., Hematological and Immunological Effects of Methadone Administration in Mice. Research Communication in Substances of Abuse. 1980;1(2):177-83.

Neumann et al., Plasma morphine concentrations during chronic oral administration in patients with cancer pain. Pain. Jul. 1982;13(3):247-52.

Nielsen et al., Glycolamide Esters as Biolabile Prodrugs of Carboxylic Acid Agents: Synthesis, Stability, Biocenversion, and Physicochemical Properties. J Pharma Sci. 1988;77:285-98.

Niemegeers et al., Difenoxine (R 15403), the active metabolite of diphenoxylate (R 1132). 2. Difneozine, a potent, orally active and safe antidiarrheal agent in rats. Arzneimittelforschung. Mar. 1972;22(3):516-8.

Novick et al., Natural killer cell activity and lymphocyte subsets in parenteral heorin abusers and long-term methadone maintenance patients. J Pharmacol Exp Ther. Aug. 1989;250(2):606-10.

Odio et al., Central but not peripheral opiate receptor blockade prolonged pituitary-adrenal responses to stress. Pharmacol Biochem Behav. Apr. 1990;35(4):963-9.

O'Keefe et al., Bowel Disorders Impair Functional Status and Quality of Life in the Elderly: A Population-Based Study. J Gerontol. 1995;50:184-89.

Osinski et al., Determination of methylnaltrexone in clinical samples by solid-phase extraction and high-performance liquid chromatography for a pharmacokinetics study. J Chromatogr B Analyt Technol Biomed Life Sci. Nov. 25, 2002;780(2):251-9.

Papapetropoulos et al., Nitric oxide synthase inhibitors attenuate transforming-growth-factor-beta 1-stimulated capillary organization in vitro. Am J Pathol. May 1997;150(5):1835-44.

Pappagallo, Incidence, prevalence, and management of opioid bowel dysfunction. Am J Surg. Nov. 2001;182(5A Suppl):11S-18S.

Pasi et al., Angiogenesis: modulation with opioids. Gen Pharmacol. 1991;22(6):1077-9.

Pastel et al., COX-2 and iNOS in opioid-induced delayed cardioprotection in the intact rat. Life Sci. May 28, 2004;75(2):129-40.

Paulson et al., Alvimopan: an oral, peripherally acting, mu-opioid receptor antagonist for the treatment of opioid-induced bowel dysfunction—a 21-day treatment-randomized clinical trial. J Pain. Mar. 2005;6(3):184-92.

Peart et al., Opioid-induced preconditioning: recent advances and future perspectives. Vascul Pharmacol. Apr.-May 2005;42(5-6):211-8. Epub Mar. 17, 2005.

(56) References Cited

OTHER PUBLICATIONS

Peeters et al., The motilin antagonist ANQ-11125 blocks motilide-induced contractions in vitro in the rabbit. Biochem Biophys Res Commun. Jan. 28, 1994;198(2):411-6. Abstract Only.

Peterson et al., Morphine promotes the growth of HIV-1 in human peripheral blood mononuclear cell cocultures. AIDS. Sep. 1990;4(9):869-73.

Pham et al., Drugs of Abuse: Chemistry, Pharmacology, Immunology and AIDS; National Institute of Drug Research 96: Monograph Series. U.S. Department of Health and Human Services; 1990. 243 pages.

Polak et al., Enkephalin-like immunoreactivity in the human gastrointestinal tract. Lancet. May 7, 1977;1(8019):972-4.

Polakiewicz et al., mu-Opioid receptor activities signaling pathways implicated in cell survival and translational control. J Biol Chem. Sep. 4, 1998;273(36):23534-41.

Poonawala et al., Opioids heal ischemic wounds in the rat. Wound Repair Regen. Mar.-Apr. 2005;13(2):165-74.

Powell et al., Paradoxical effects of the opioid antagonist naltrexone on morphine analgesia, tolerance, and reward in rats. J Pharmacol Exp Ther. Feb. 2002;300(2):588-96.

Pugsley et al., Cardiovascular actions of the kappa-agonist, U-50,488H, in the absence and presence of opioid receptor blockade. Br J Pharmacol. Mar. 1992;105(3):521-6.

Quang-Contagrel et al., Long-term methadone treatment: effect on CD4+ lymphocyte counts and HIV-1 plasma RNA level in patients with HIV infection. Eur J Pain. 2001;5(4):415-20.

Quock, et al, Microwave facilitation of methylnaltrexone antagonism of morphine-induced analgesia in mice. J Bioelect. 1986;5(1):35-46.

Quock et al., Narcotic antagonist-induced hypotension in the spontaneously hypertensive rat. Life Sci. Sep. 2, 1985;37(9):819-26.

Quock et al., Narcotic antagonist potentiation of apomorphine drug effect: a stereospecific, centrally mediated drug action. Prog Neuropsychopharmacol Biol Psychiatry. 1985;9(3):239-43.

Radulović et al., Opioid receptor-mediated suppression of humoral immune response in vivo and in vitro: involvement of kappa opioid receptors. J Neuroimmunol. Mar. 1995;57(1-2):55-62.

Ramabadran, Effects of N-methylnaloxone and N-methylnaltrexone on nociception and precipitated abstinence in mice. Life Sci. Sep. 20-27, 1982;31(12-13):1253-6.

Read et al., Interpretation of the breath hydrogen profile obtained after ingesting a solid meal containing unabsorbable carbohydrate. Gut. Aug. 1985;26(8):834-42.

Reisine et al., Opioid Analgesics and Antagonists. In: Goodman & Goodman's The Pharmacological Basis of Therapeutics. 9th Ed. 1996:521-55.

Resnick et al., Delayed gastric emptying and postoperative ileus after nongastric abdominal surgery: part 1. Am J Gastroenterol. May 1997;92(5):751-62.

Resnick et al., Delayed gastric emptying and postoperative ileus after nongastric abdominal surgery: part II. Am J Gastroenterol. Jun. 1997;92(6):934-40.

Risdahl et al., Opiates and infection. J Neuroimmunol. Mar. 15, 1998;83(1-2):4-18.

Riviére et al., Fedotozine reverses ileus induced by surgery or peritonitis: action at peripheral kappa-opioid receptors. Gastroenterology. Mar. 1993;104(3):724-31.

Robinson et al., Oral naloxone in opioid-associated constipation. Lancet. Aug. 31, 1991;338(8766):581-2.

Roger et al., Colonic motor responses in the pony: relevance of colonic stimulation by opiate anatgonists. Am J Vet Res. Jan. 1985;46(1):31-5.

Roy et al., Morphine modulates NF kappa B activation in macrophages. Biochem Biophys Res Commun. Apr. 17, 1998;245(2):392-6.

Russell et al., Antagonism of gut, but not central effects of morphine with quaternary narcotic antagonists. Eur J Pharmacol. Mar. 12, 1982;78(3):255-61.

Sachs et al., Peripheral analgesic blockade by hypernociception: activation of aginine/NO/cGMP/protein kinase G/ATP-sensitive K+ channel pathway. Proc Natl Acad Sci U S A. Mar. 9, 2004;101(10):3680-5. Epub Feb. 27, 2004.

Saffran et al., A new approach to the oral administration of insulin and other peptide drugs. Science. Sep. 5, 1986;233(4768):1081-4. Abstract Only.

Sakurada et al., Differential antagonism of endomorphin-1 and endomorphin-2 supraspinal antinociception by naloxonazine and 3-methylnaltrexone. Peptides. May 2002;23(5):895-901.

Sandner-Keisling et al., Pharmacology of opioid inhibition to noxious uterine cervical distension. Anesthesiology. Oct. 2002;97(4):966-71.

Sawhney et al., Bioerodible Hydrogels Based on Photopolymerized Poly(ethylene glycol)-co-poly(α-hydroxy acid) Diacrylate Macromers. Macromolecules. 1993;26:581-87.

Schaefer et al., Effects of opioid antagonists and their quaternary derivatives on locomotor activity and fixed ratio responding for brain self-stimulation in rats. Pharmacol Biochem Behav. Nov. 1985;23(5):797-802.

Schang et al., Beneficial effects of naloxone in a patient with intestinal pseudoobstruction. Am J Gastroenterol. Jun. 1985;80(6):407-11.

Schang et al., How does morphine work on colonic motility? An electromyographic study in the human left and sigmoid colon. Life Sci. Feb. 24, 1986;38(8):671-6.

Schiller et al., Studies of the mechanism of the antidiarrheal effect of codeine. J Clin Invest. Nov. 1982;70(5):999-1008.

Schmidhammer, et al., Synthesis and biological evaluation of 14-alkoxymorphinans. Part 9. 14-O-ethyl-5-methylnaltrexone, an opioid antagonist with unusual selectivity. Helv Chim Acta. 1993;(1):476-80.

Schmidhammer, et al., Synthesis and biological evaluation of 14-alkoxymorphinans. Part 10. 14-O-methyl derivatives of 5-methylnaltrexone and 5-methylnaloxone. Helv Chim Acta. 1994;77(6):1585-9.

Schmidt et al., Alvimopan® (ADL 8-2698) is a novel peripheral opioid antagonist. Am J Surg. Nov. 2001;182(5A Suppl):27S-38S.

Scholz, Managing constipation that's opioid-induced. 2000; 63(6):103.

Schreier et al., Central regulation of intestinal function: morphine withdrawal diarrhea. Proc West Pharmacol Soc. 1982;25:151-4.

Schubert-Zsilavecz et al., [Das reizdarmsyndrom] The irritable bowel syndrom. Deutsche apotheker zeitung. Aug. 22, 2002; 142(34): 40-9. German.

Schug et al., A long-term survey of morphine in cancer pain patients. J Pain Symptom Manage. Jul. 1992;7(5):259-66. Abstract Only.

Schuller et al., M6G, but not morphine, inhibits GI transit in mu opioid receptor deficient mice. Society of Neuroscience Abstract. 1998;24:524. Abstract 210.7.

Sezen et al., Renal excretorty responses produced by the delta opioid agonist, BW373U86, in conscious rats. J Pharmacol Exp Ther. Oct. 1998;287(1):238-45.

Shahbazian et al., Involvement if mu- and kappa-, but not delta-, opioid receptors in the peristaltic motor depression caused by endogenous and exogenous opioids in the guinea-pig intestine. Br J Pharmacol. Feb. 2002;135(3):741-50.

Shavit et al., Effects of a single administration of morphine or footshock stress on natural killer cell cytotoxicity. Brain Behav Immun. Dec. 1987;1(4):318-28.

Shi et al., Cardioprotective effects of morphine on rat heart suffering from ischemia and reperfusion. Chin Med J (Engl). Jul. 2003;116(7):1059-62.

Simonin et al., kappa-Opioid receptor in humas: cDNA and genomic cloning, chromosomal assignment, functional expression, pharmacology, and expression pattern in the central nervous system.. Proc Natl Acad Sci U S A. Jul. 18, 1995;92(15):7006-10.

Simonin et al., The human delta-opioid receptor: genomic organization, cDNA cloning, functional expression, and distribution in human brain. Mol Pharmacol. Dec. 1994;46(6):1015-21. Abstract Only.

Soldani et al., Central and peripheral involvement of mu receptors in gastric secretory effects of opioids in the dog. Eur J Pharmacol. Nov. 19, 1985;117(3):295-301.

(56) References Cited

OTHER PUBLICATIONS

Solvason et al., Naltrexone blocks the expression of the conditioned elevation of natural killer cell activity in BALB/c mice. Brain Behav Immun. Sep. 1989;3(3):247-62.

Stankski et al., Kinetics of intravenous and intramascular morphine. Clin Pharmacol Ther. Jul. 1978;24(1):52-9.

Steele et al., HIV-1 Infection and Opioid Administration Modulate the Expression of Chemokine Receptors. Drug and Alcohol Dependence. 2000:60(Supp 1):S212. Abstract 599.

Stefano et al., Delta2 opioid receptor subtype on human vascular endothelium uncouples morphine stimulated nitric oxide release. Int J Cardiol. Apr. 30, 1998;64 Suppl 1:S43-51.

Stefano et al., Long-term exposure of human blood vessels to HIV gp120, morphine, and anandamide increased endothelial adhesion of monocytes: uncoupling of nitric oxide release. J Cardiovasc Pharmacol. Jun. 1998;31(6):862-8.

Stefano et al., Morphine enhances nitric oxide release in the mammalian gastrointestinal tract via the micro(3) opiate receptor subtype: a hormonal role for endogenous morphine. J Physiol Pharmacol. Mar. 2004;55(1 Pt 2):279-88.

Stefano et al., Presence of the mu3 opiate receptor in endothelial cells. Coupling to nitric oxide production and vasodilation. J Biol Chem. Dec. 22, 1995;270(51):30290-3.

Steinbrook et al., An opioid antagonist for postoperative ileus. N Engl J Med. Sep. 27, 2001;345(13):988-9.

Stephenson et al., Methylnaltrexone reverses opioid-induced constipation. Lancet Oncol. Apr. 2002;3(4):202.

Sternini et al., The opioid system in the gastrointestinal tract. Neurogastroenterol Motil. Oct. 2004;16 Suppl 2:3-16.

Stewart et al., Central and peripheral actions of morphine on intestinal transit. J Pharmacol Exp Ther. Jun. 1978;205(3):547-55.

Stiene-Martin et al., Regional, developmental, and cell cycle-dependent differences in mu, delta, and kappa-opioid receptor expression among cultured mouse astrocytes. Glia. Mar. 1998;22(3):249-59.

Suzuki et al., Morphine suppresses lymphocyte apoptosis by blocking p53-mediated death signaling. Biochem Biophys Res Commun. Sep. 5, 2003;308(4):802-8.

Swan, et al., NIDA plays key role in studying links between AIDS and drug abuse. AIDS Research, NIDA Notes. 1995; 10(3):1-4.

Sykes, Oral naloxone in opioid-associated constipation. Lancet. Jun. 15, 1991;337(8755):1475.

Sykes, Chapter 9. Using oral naloxone in management of opioid bowel dysfunction. Handbook of Opioid Bowel Syndrome, New York, Haworth Medical Press, Yuan, C-S, editor. 2005:175-95.

Szabo et al., Interactions of opioid receptors, chemokines, and chemokine receptors. Adv Exp Med Biol. 2001;493:69-74.

Taguchi et al., Selective postoperative inhibition of gastrointestinal opioid receptors. N Engl J Med. Sep. 27, 2001;345(13):935-40.

Talley et al., Pharmacologic therapy for the irritable bowel syndrome. Am J Gastroenterol. Apr. 2003;98(4):750-8.

Tavani et al., Morphine is most effective on gastrointestinal propulsion in rats by intraperitoneal route: evidence for local action. Life Sci. Dec. 8, 1980;27(23):2211-7.

Tegeder et al., Opioids as modulators of cell death and survival—unraveling mechnisms and revealing new indications. Pharmacol Rev. Sep. 2004;56(3):351-69.

Thomas et al., A phase III double-blind placebo-conrtolled trial of methylnaltrexone (MNTX) for opioid-induced constipation (OIC) in advanced medical illness (AMI). Abstract No. LBA8003 from the 2005 ASCO Annual Meeting. 3 pages.

Thomas et al., Amelioration of peripheral side effects of opioids: clinical experience with methylnaltrexone (MNTX). Proc World Congr Anesth. 2004:107. Abstract Only.

Thompson, Laxatives: clinical pharmacology and rational use. Drugs. Jan. 1980;19(1):49-58.

Thompson et al., Opioid stimulation in the ventral tegmental area facilitates the onset of maternal behavior in rats. Brain Res. Dec. 16, 1996;743(1-2):184-201.

Tomiyasu et al., Analysis of intercostal nerve damage associated with chronic post-thoracotomy pain. Anesthesiology. 2001;95. Abstract A-964.

Tryoen-Toth et al., Regulation of kappa-opioid receptor mRNA level by cyclic AMP and growth factors in cultured rat glial cells. Brain Res Mol Brain Res. Mar. 30, 1998;55(1):141-50.

Ukai et al., Suppression of deprivation-induced water intake in the rat by opioid antagonists: central sites of action. Psychopharmacology (Berl). 1987;91(3):279-84.

Uwai et al., Syntheses and receptor-binding studies of derivatives of the opioid antagonist naltrexone. Bioorg Med Chem. Jan. 15, 2004;12(2):417-21.

Valentino et al., Quaternary naltrexone: evidence for the central mediation of discriminative stimulus effects of narcotic agonists and antagonists. J Pharmacol Exp Ther. Jun. 1981;217(3):652-9.

Valentino et al., Receptor binding, antagonist, and withdrawal precipitating properties of opiate antagonists. Life Sci. Jun. 20, 1983;32(25):2887-96.

Vellejo et al., Opioid therapy and immunosuppression: a review. Am J Ther. Sep.-Oct. 2004;11(5):354-65.

Vaughan et al., Huamn antibodies by design. Nat Biotechnol. Jun. 1998;16(6):535-9.

Vermiere et al., Stability and compatibility of morphine. International Journal of Pharmaceutics. 1999;187:17-51.

Waldhoer et al., Opioid receptors. Annu Rev Biochem. 2004;73:953-90.

Walker, et al., Role of central versus peripheral opioid receptors in analgesia induced by repeated administration of opioid antagonists. Psychopharmacology. 1991;104(2):164-6.

Walsh et al., The symptoms of advanced cancer: relationship to age, gender, and performance status in 1,000 patients. Support Care Cancer. May 2000;8(3):175-9. Abstract Only.

Wang et al., A non-peptide substance P antagonist (CP-96,345) inhibits morphine-induced NF-kappa B promoter activation in human NT2-N neurons. J Neurosci Res. Feb. 15, 2004;75(4):544-53.

Wang et al., Determination of tungsten in bulk drug substance and intermediates by ICP-AES and ICP-MS. J Pharm Biomed Anal. May 1999;19(6):937-43. Abstract Only.

Wang et al., Human mu opiate receptor. cDNA and genomic clones, pharmacologic characterization and chromosomal assignment. FEBS Lett. Jan. 31, 1994;338(2):217-22. Abstract Only.

Wang et al., Mobilization of calcium from intracellular stores as one of the mechanisms underlying the antiopioid effect of cholecystokinin octapeptide. Peptides. Sep.-Oct. 1992;13(5):947-51.

Wang et al., Morphine negatively regulates interferon-gamma promoter activity in activated murine T cells through two distinct cyclic AMP-dependent pathways. J Biol Chem. Sep. 26, 2003;278(39):37622-31. Epub Jul. 3, 2003.

Wang et al., The immunosuppressive effects of chronic morphine treatment are partially dependent on corticosterone and mediated by the mu-opioid receptor. J Leukoc Biol. May 2002;71(5):782-90.

Warren et al., Effects of quaternary naltrexone and chlordiazepoxide in squirrel monkeys with enhanced sensitivity to the behavioral effects of naltrexone. J Pharmacol Exp Ther. Nov. 1985;235(2):412-7.

Wei et al., Effects of Subcutaneous Methylnaltrexone on Morphine-Induces Gut Motility Changes: A Clinical Trial. Abstracts of the 2002 Annual Meeting of the American Society for Clinical Pharmacology and Therapeutics. Atlanta, Georgia, USA. Mar. 24-27, 2002. Clin Pharmacol Ther. Feb. 2002;71(2):P11. Abstract MPI-26.

Wei et al., Opioid-induced immunosuppression: is it centrally mediated or peripherally mediated? Biochem Pharmacol. Jun. 1, 2003;65(11):1761-6.

Wei et al., Pharmacokinetics of subcutaneous methylnaltrexone: different route administration comparison. 2001. ASA Annual Meeting Abstracts. Oct. 14-18, 2001. Chicago, IL. Abstract A-962.

Wentland et al., Synthesis and opioid receptor binding properties of a highly potent 4-hydroxy analogue of naltrexone. Bioorg Med Chem Lett. Apr. 15, 2005;15(8):2107-10.

Whistler et al., Functional dissociation of mu opioid receptor signaling and endocytosis: implications for the biology of opiate tolerance and addiction. Neuron. Aug. 1999;23(4):737-46.

(56) References Cited

OTHER PUBLICATIONS

Willett et al., Direct evidence that the VEGF-specific antibody bevacizumab has antivascular effects in human rectal cancer. Nat Med. Feb. 2004;10(2):145-7. Epub Jan. 25, 2004.

Willette, et al., Evidence for anticholinergic effects of naltrexone methylbromide. Res Comm Subst Abuse. 1983;4(4):325-37.

Wilmore, Can we minimize the effects of opioids on the bowel and still achieve adequate pain control? Am J Surg. Nov. 2001;182(5A Suppl):1S-2S.

Wingo et al., Cancer statistics, 1995. CA Cancer J Clin. Jan.-Feb. 1995;45(1):8-30.

Witkin et al., Pharmacology of 2-amino-indane hydrochloride (Su-8629): a potent non-narcotic analgesic. J Pharmacol Exp Ther. Sep. 1961;133:400-8. Abstract Only.

Wittert et al., Tissue distribution of opioid receptor gene expression in the rat. Biochem Biophys Res Commun. Jan. 26, 1996;218(3):877-81.

Wolff et al., Alvimopan, a novel, peripherally acting mu opioid antagonist: results of a multicenter, randomized, double-blind, placebo-controlled, phase III trial of major abdominal surgery and post-operative ileus. Ann Surg. Oct. 2004;240(4):728-34; discussion 734-5.

Wybran et al., Suggestive evidence for receptors for morphine and methionine-enkephalin on normal human blood T lymphocytes. J Immunol. Sep. 1979;123(3):1068-70.

Yamamoto et al., Inhibition of stress-stimulated colonic propulsion by alpha 2-adrenoceptor antagonists in rats. Neurogastroenterol Motil. Dec. 1998;10(6):523-32. Abstract Only.

Yeh et al., Stability of morphine in aqueous solution. Am J Hosp Pharmacy. 1960;17(2):101-103.

Yoshida et al., Effect of surgical stress on endogenous morphine and cytokine levels in the plasma after laparoscopoic or open cholecystectomy. Surg Endosc. Feb. 2000;14(2):137-40.

Yuan et al., Antagonism of chronic opioid-induce gut effects. Anesth Analg. 2000;90:S1-523. Abstract S479.

Yuan et al., Antagonism of gastrointestinal opioid effects. Reg Anesth Pain Med. Nov.-Dec. 2000;25(6):639-42.

Yuan et al., Clinical status of methylnaltrexone, a new agent to prevent and manage opioid-induced side effects. J Support Oncol. Mar.-Apr. 2004;2(2):111-7; discussion 119-22.

Yuan et al., Dose-related effects of oral acetaminophen on cold-induced pain: a double-blind, randomized, placebo-controlled trial. Clin Pharmacol Ther. Mar. 1998;63(3):379-83.

Yuan et al., Effects of enteric-coated methylnaltrexone in preventing opioid-induced delay in oral-cecal transit time. Clin Pharmacol Ther. Apr. 2000;67(4):398-404.

Yuan et al., Effects of intravenous methylnaltrexone on opioid-induced gut motility and transit time changes in subjects receiving chronic methadone therapy: a pilot study. Pain. Dec. 1999;83(3):631-5.

Yuan et al., Effects of low-dose morphine on gastric emptying in healthy volunteers. J Clin Pharmacol. Nov. 1998;38(11):1017-20.

Yuan et al., Effects of methylnaltrexone on chronic opioid induced gut motility and transit time changes. Br J Anaesth. 1998;81(1):94. Abstract Only.

Yuan et al., Effects of methylnaltrexone on chronic opioid-induced gut motility and transit time changes. University of Leicester—Abstracts from the Eighth International Symposium on Pain, Anaesthesia and Endocrinology. Sep. 18-19, 1997.

Yuan et al., Effects of methylnaltrexone on morphine-induced inhibition of contractions in isolated guinea-pig and human intestine. Anesthesiology. Sep. 1995; 83(3A). Abstract A358.

Yuan et al., Effects of methylnaltrexone on morphine-induced inhibition of contraction in isolated guinea-pig ileum and human intestine. Eur J Pharmacol. Mar. 24, 1995;276(1-2):107-11.

Yuan et al., Effects of subcutaneous methylnaltrexone on Morphine-induced peripherally mediated side effects: a double-blind randomized placebo-controlled trial. J Pharmacol Exp Ther. Jan. 2002;300(1):118-23.

Yuan et al., Efficacy of orally administered methylnaltrexone in decreasing subjective effects after intravenous morphine. Drug Alcohol Depend. Oct. 1, 1998;52(2):161-5.

Yuan et al., Gastric effects of methylnaltrexone on mu, kappa, and delta opioid agonists induced brainstem unitary responses. Neuropharmacology. Mar. 1999;38(3):425-32.

Yuan et al., Gastric effects of mu-, delta- and kappa-opioid receptor agonists on brainstem unitary responses in the neonatal rat. Eur J Pharmacol. Oct. 24, 1996;314(1-2):27-32.

Yuan et al., Gut and brain effects of American ginseng root on brainstem neuronal activities in rats. Amer J Clin Med. 1998; 26: 47-55.

Yuan et al., Gut motility and transit changes in patients receiving long-term methadone maintenance. J Clin Pharmacol. Oct. 1998;38(10):931-5.

Yuan et al., Methylnaltrexone, a novel peripheral opioid receptor antagonist for the treatment of opioid side effects. Expert Opin Investig Drugs. May 2006;15(5):541-52.

Yuan et al., Methylnaltrexone (MNTX) for chronic opioid-induced constipation. 2002 ASCO Annual Meeting. Proc Am Soc Clin Oncol. 2002;21:376a. Abstract 1501.

Yuan et al., Methylnaltrexone (MNTX) reverses chronic opioid constipation: a double-blind, randomized, placebo-controlled trial. Anesthesiology. Sep. 1999;91 (3A). Abstract A973.

Yuan et al., Methylnaltrexone changes gut motility and transit time in chronic methadone-maintained subjects. Anesth Analg. 1999;88:S1-424. Abstract S404.

Yuan et al., Methylnaltrexone effects on morphine-induced inhibition in isolated guinea-pig and human intestine. Clin Pharm & Therapeut. Feb. 1995;57:138. Abstract P1-11.

Yuan et al., Methylnaltrexone for reversal of constipation due to chronic methadone use: a randomized controlled trial. JAMA. Jan. 19, 2000;283(3):367-72.

Yuan et al., Methylnaltrexone prevents morphine-induced delay in oral-cecal transit time without affecting analgesia: a double-blind randomized placebo-controlled trial. Clin Pharmacol Ther. Apr. 1996;59(4):469-75.

Yuan et al., Methylnaltrexone prevents morphine-induced kaolin intake in the rat. Anesthesiology. 2003;99. Abstract A-922.

Yuan et al., Methylnaltrexone reduces oral-cecal transit time in humans. Dig Dis Week Abstr. 2003:A-578. Abstract T1840.

Yuan et al., Methylnaltrexone reverses morphine-induced changes in gastrointestinal motility: a clinical study. Anesthesiology Sep. 1995; 83(3A): Abstract A360.

Yuan et al., Methylnaltrexone: Investigation of clinical applications. Drug Develop Res. 2000;50(2):133-41.

Yuan et al., Opioid analgesia without gut side effects: effects of methylnaltrexone as a novel peripheral opioid antagonist. Assoc Univ Anesth Abst. 2003: PD2.

Yuan et al., Oral methylnaltrexone for opioid-induced constipation. JAMA. Sep. 20, 2000;284(11):1383-4.

Yuan et al., Oral methylnaltrexone reverses chronic opioid-induced constipation. Anesthesiology. Sep. 2000;93(3A). Abstract A-872.

Yuan et al., Oral methylnaltrexone reverses morphine-induced changes in gastrointestiinal motility. Anesthesiology. Sep. 1995;85(3A). Abstract A335.

Yuan et al., Pain control without side effects: clinical studies on methylnaltrexone as a novel peripheral opioid antagonist. $7^{th}$ America-Japan Anesth Congr. Yamanashi, Japan. 2002:41.

Yuan et al., Pharmacokinetics of intravenous vs. oral methylnaltrexone: evidence for direct gut effects. Anesth Analg. 2001;92: S1-363. Abstract S274.

Yuan et al., Safety and tolerance of oral methylnaltrexone in healthy volunteers. Anesth Analg. 1997;84:S1-599. Abstract S574.

Yuan et al., Subcutaneous methylnaltrexone prevents morphine-induced delay in gut transit time: a clinical trial. Anesthesiology. 2001;95. Abstract A-963.

Yuan et al., The safety and efficacy of oral methylnaltrexone in preventing morphine-induced delay in oral-cecal transit time. Clin Pharmacol Ther. Apr. 1997;61(4):467-75.

(56) References Cited

OTHER PUBLICATIONS

Yuan et al., Tolerability, gut effects, and pharmacokinetics of methylnaltrexone following repeated intravenous administration in humans. J Clin Pharmacol. May 2005;45(5):538-46.

Zagon et al., Opioids and differentiation in human cancer cells. Neuropeptides. Oct. 2005;39(5):495-505. Epub Sep. 15, 2005.

Zagon et al., Opioids and the apoptotic pathway in human cancer cells. Neuropeptides. Apr. 2003;37(2):79-88.

Zagon et al., Opioid antagonists inhibit the growth of metastatic murine neuroblastoma. Cancer Lett. Nov. 1983;21(1):89-94.

Zagon et al., Opioid growth factor regulates the cell cycle of human neoplasias. Int J Oncol. Nov. 2000;17(5):1053-61.

Zhang et al., Dynorphin A as a potential endogenous ligand for four members of the opioid receptor gene family. J Pharmacol Exp Ther. Jul. 1998;286(1):136-41.

Zhang et al., Effect of the endogenous kappa opioid agonist dynorphin A(1-17) on cocaine-evoked increases in striatal dopamine levels and cocaine-induced place preference in C57BL/6J mice. Psychopharmacolohy (Berl). Apr. 2004;172(4):422-9. Epub Jan. 8, 2004.

Zimmerman et al., Discovery of a potent, peripherally selective trans-3,4-dimethyl-4-(3-hydroxyphenyl) piperidine opioid antagonist for the treatment of gastrointestinal motility disorders. J Med Chem. Jul. 22, 1994, 37(15):2262-5.

\* cited by examiner

CRYSTAL FORMS OF (R)-N-METHYLNALTREXONE BROMIDE AND USES THEREOF

RELATED APPLICATIONS

The present application is a continuation of U.S. patent application Ser. No. 12/593,615, filed Aug. 12, 2010, which is a 35 U.S.C. §371 national stage filing of International Application No. PCT/US2008/004116, filed on Mar. 28, 2008, which claims priority to U.S. Provisional Patent Application No. 60/921,111, filed Mar. 29, 2007, the entirety of each of which applications are hereby incorporated herein by reference.

BACKGROUND OF THE INVENTION

Opioids are widely used in patients with advanced cancers and other terminal diseases to lessen suffering. Opioids are narcotic medications that activate opioid receptors located in the central nervous system to relieve pain. Opioids, however, also react with receptors outside of the central nervous system, resulting in side effects including constipation, nausea, vomiting, urinary retention, and severe itching. Most notable are the effects in the gastrointestinal tract (GI) where opioids inhibit gastric emptying and propulsive motor activity of the intestine, thereby decreasing the rate of intestinal transit and producing constipation. The effectiveness of opioids for pain is often limited due to resultant side effects, which can be debilitating and often cause patients to cease use of opioid analgesics.

In addition to analgesic opioid induced side effects, studies have suggested that endogenous opioid compounds and receptors may also affect activity of the gastrointestinal (GI) tract and may be involved in normal regulation of intestinal motility and mucosal transport of fluids in both animals and man, (Koch, T. R, et al, Digestive Diseases and Sciences 1991, 36, 712-728; Schuller, A. G. P., et al., Society of Neuroscience Abstracts 1998, 24, 524, Reisine, T., and Pasternak, G., Goodman & Gilman's The Pharmacological Basis of Therapeutics Ninth Edition 1996, 521-555 and Bagnol, D., et al., Regul. Pept. 1993, 47, 259-273). Thus, an abnormal physiological level of endogenous compounds and/or receptor activity may lead to bowel dysfunction.

For example, patients who have undergone surgical procedures, especially surgery of the abdomen, often suffer from a particular bowel dysfunction, called post-operative (or post-surgical) ileus, that may be caused by fluctuations in natural opioid levels. Similarly, women who have recently given birth commonly suffer from post-partum ileus, which is thought to be caused by similar natural opioid fluctuations as a result of birthing stress. Gastrointestinal dysfunction associated with post-operative or post partum ileus can typically last for 3 to 5 days, with some severe cases lasting more than a week. Administration of opioid analgesics to a patient after surgery, which is now an almost universal practice, may exacerbate bowel dysfunction, thereby delaying recovery of normal bowel function, prolonging hospital stays, and increasing medical care costs.

Opioid receptor antagonists such as naloxone, naltrexone, and nalmefene, have been studied as a means of antagonizing undesirable peripheral effects of opioids. However, these agents act not only on peripheral opioid receptors, but also on central nervous system sites, so that they sometimes reverse the beneficial analgesic effects of opioids, or cause symptoms of opioid withdrawal. Preferable approaches for use in controlling opioid-induced side effects include administration of peripheral opioid receptor antagonist compounds that do not readily cross the blood-brain barrier. For example, the peripheral μ opioid receptor antagonist compound methylnaltrexone and related compounds have been disclosed for use in curbing opioid-induced side effects in patients (e.g., constipation, pruritus, nausea, and/or vomiting). See, e.g., U.S. Pat. Nos. 5,972,954, 5,102,887, 4,861,781, and 4,719,215; and Yuan, C.-S. et al. Drug and Alcohol Dependence 1998, 52, 161. Similarly, peripherally selective piperidine-N-alkylcarboxylate and 3,4-dimethyl-4-aryl-piperidine opioid receptor antagonists have been described as being useful for treatment of opioid-induced side effects constipation, nausea or vomiting, as well as irritable bowel syndrome and idiopathic constipation. See, e.g., U.S. Pat. Nos. 5,250,542, 5,434,171, 5,159,081, and 5,270,328.

It would be desirable to provide peripheral μ opioid receptor antagonist compounds in a form suitable for administration to a patient in need of treatment for any of the above-mentioned disorders.

SUMMARY

The present invention provides solid forms of Compound 1, a peripheral μ opioid receptor antagonist:

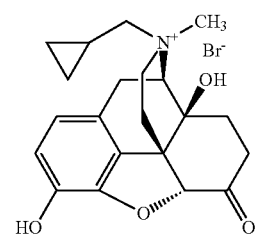

1 where the compound is in the (R) configuration with respect to the nitrogen. The present invention also provides pharmaceutical compositions and formulations comprising such solid forms. Compound 1, and inventive solid forms thereof, is useful for the treatment, prevention, amelioration, delay or reduction of severity and/or incidence of side effects associated with opioid administration, such as, for example, gastrointestinal dysfunction (e.g., inhibition of intestinal motility, constipation, GI sphincter constriction, nausea, emesis (vomiting), biliary spasm, opioid bowel dysfunction, colic), dysphoria, pruritus, urinary retention, depression of respiration, papillary constriction, cardiovascular effects, chest wall rigidity and cough suppression, depression of stress response, and immune suppression associated with administration of narcotic analgesia, etc, or combinations thereof. Other uses of Compound 1, and inventive solid forms thereof as described herein, are set forth infra.

DETAILED DESCRIPTION OF CERTAIN EMBODIMENTS OF THE INVENTION

Figure 1A:
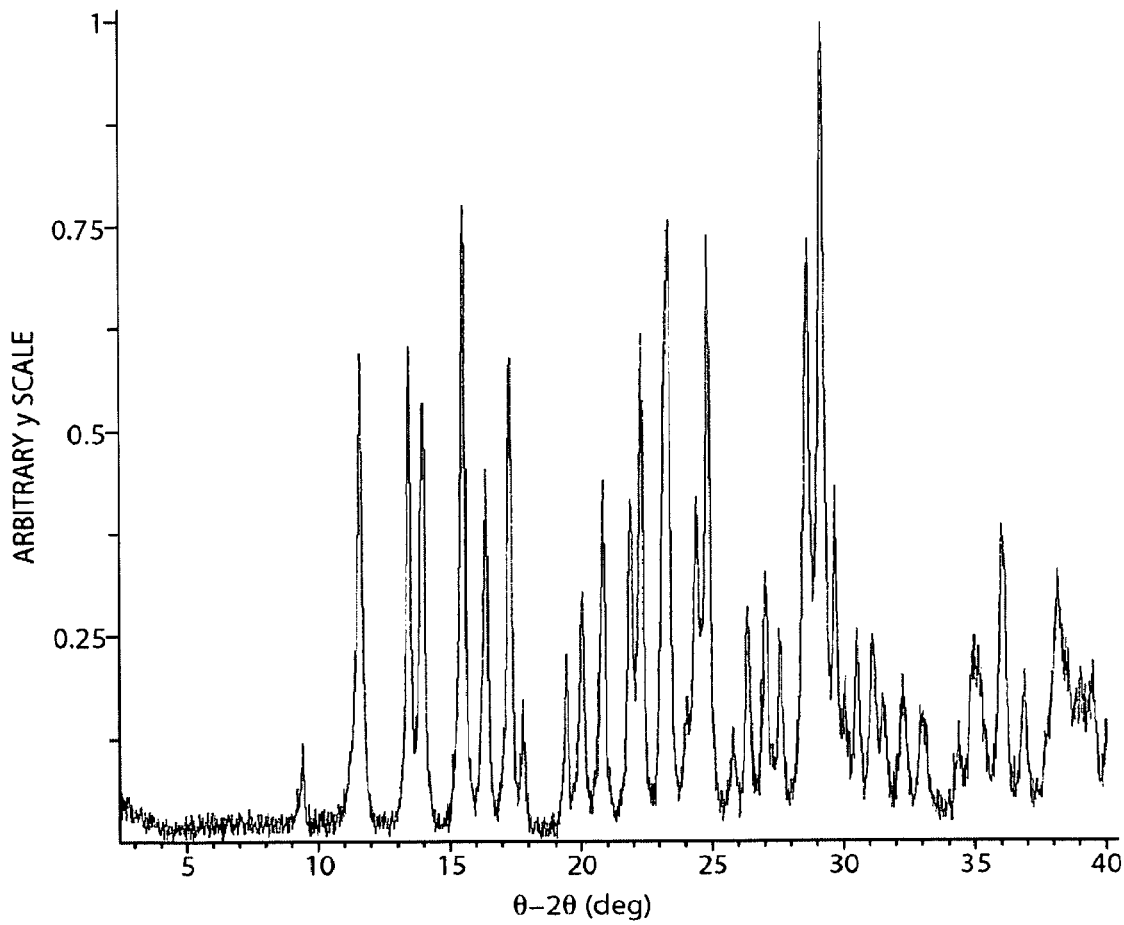
FIG. 1A depicts the X-Ray Powder Diffraction pattern for Form A.

General Description of Certain Aspects of the Invention

International patent application publication number WO2006/127899 describes Compound 1, (R)—N-methylnaltrexone bromide, which has the following structure;

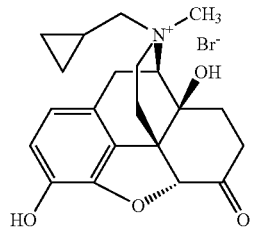

where the compound is in the (R) configuration with respect to the nitrogen. In certain embodiments of the present invention, at least about 99.6%, 99.7%, 99.8%, 99.85%, 99.9%, or 99.95% of Compound 1 is in the (R) configuration with respect to nitrogen. Methods for determining the amount of (R)—N-methylnaltrexone bromide, present in a sample as compared to the amount of (S)—N-methylnaltrexone bromide present in that same sample, are described in detail in WO2006/127899, the entirety of which is hereby incorporated herein by reference. In other embodiments, Compound 1 contains 0.45% or less (S)—N-methylnaltrexone bromide. In still other embodiments, Compound 1 contains 0.30% or 0.05% or less (S)—N-methylnaltrexone bromide.

Compound 1, also known as "(R)-MNTX," exhibits peripheral μ opioid receptor antagonist activity in therapeutic models. Accordingly, Compound 1 is useful for antagonizing undesirable side effects of opioid activity, including those associated with opioid analgesic therapy (e.g., gastrointestinal effects (e.g., delayed gastric emptying, altered GI tract motility), etc.). In certain embodiments of the present invention, Compound 1 is useful for the treatment, prevention, amelioration, delay or reduction of severity and/or incidence of side effects associated with opioid administration, such as, for example, gastrointestinal dysfunction (e.g., inhibition of intestinal motility, constipation, GI sphincter constriction, nausea, emesis (vomiting), biliary spasm, opioid bowel dysfunction, colic), dysphoria, pruritus, urinary retention, depression of respiration, papillary constriction, cardiovascular effects, chest wall rigidity and cough suppression, depression of stress response, and immune suppression associated with administration of narcotic analgesia, etc, or combinations thereof. Other uses of Compound 1, and forms thereof as described herein, are set forth infra.

Solid Forms of Compound 1:

It has been found that Compound 1 can exist in a variety of solid forms. Such forms include neat crystal forms, known as polymorphs. Such solid forms also include solvates, hydrates, and amorphous. All such solid forms of Compound 1 are contemplated by the present invention. In certain embodiments, the present invention provides Compound 1 as a mixture of one or more solid forms selected from polymorphs, solvates, hydrates, and amorphous Compound 1.

As used herein, the term "polymorph" refers to different crystal structures achieved by a particular chemical entity. Specifically, polymorphs occur when a particular chemical compound can crystallize with more than one structural arrangement. As used herein, the term "solvate" refers to a crystal form where a stoichiometric or non-stoichiometric amount of solvent, or mixture of solvents, is incorporated into the crystal structure. Similarly, the term "hydrate" refers to a crystal form where a stoichiometric or non-stoichiometric amount of water is incorporated into the crystal structure.

In certain embodiments of the present invention, Compound 1 is provided as a crystalline solid, in some embodiments, the crystalline solid is substantially free of amorphous Compound 1. As used herein, the term "substantially free of amorphous Compound 1" means that the solid contains no significant amount of amorphous Compound 1. In certain embodiments of the present invention, the term "substantially free of amorphous Compound 1" means that at least about 95% by weight of Compound 1 in the solid is in crystalline form. In still other embodiments of the invention, the term "substantially free of amorphous Compound 1" means that at least about 99% by weight of Compound 1 in the solid is in crystalline form.

In certain embodiments of the present invention, Compound 1 is provided as a neat crystal form and thus does not have any water or solvent incorporated into the crystal structure. It has been found that Compound 1 can exist in at least one neat crystal form, or polymorph, referred to herein as Form A.

In certain embodiments, the present invention provides Form A of Compound 1. In other embodiments, the present invention provides Form A of Compound 1 characterized in that it has a peak in its X-ray powder diffraction ("XRPD") pattern at about 20.06 degrees 2-theta. As used herein, the term "about", when used in reference to any degree 2-theta value recited herein, refers to the stated value±0.2 degree 2-theta.

In certain embodiments, degree 2-theta values, as described herein, are reported with two decimal places. In other embodiments, degree 2-theta values, as described herein, are reported with one decimal place. In still other embodiments, degree 2-theta values, as described herein, are reported with no decimal places. It will be understood that where the term "about" is used in reference to any degree 2-theta value recited herein, this term refers to the stated value±0.2 degree 2-theta in accordance with the value's reported decimal place.

According to another embodiment, Form A of Compound 1 is characterized in that it has one or more peaks in its calculated XRPD pattern, for single crystal data collected at a temperature of 150±1° K, selected from those at about 116, 13.9, 16.85, 17.35, 23, 23.85, 24.7, 26.75, and 34.75 degrees 2-theta. In other embodiments, Form A of Compound 1 is characterized in that it has two or more, or three or more, peaks in its calculated XRPD pattern, for single crystal data collected at a temperature of 1.50±1° K selected from those at about 13.6, 13.9, 16.85, 17.35, 23, 23.85, 24.7, 26.75, and 34.75 degrees 2-theta. In still other embodiments, Form A of Compound 1 is characterized in that it has substantially all of the peaks in its calculated XRPD pattern, for single crystal data collected at a temperature of 150±1° K, selected from those at about 13.6, 13.9, 16.85, 17.35, 23, 23.85, 24.7, 26.75, and 34.75 degrees 2-theta.

In other embodiments, Form A of Compound 1 is characterized in that is has substantially all of the peaks in its XRPD pattern listed in Table 1A, below.

TABLE 1A

| XRPD Peaks for Form A Form A (°2θ) |
| --- |
| 11.56 |
| 13.44 |
| 13.98 |
| 15.52 |
| 16.4 |
| 17.3 |
| 19.42 |
| 20.06 |
| 20.82 |
| 21.9 |
| 22.3 |
| 23.34 |
| 24.42 |
| 24.84 |
| 26.38 |
| 27 |
| 27.64 |
| 28.62 |
| 29.16 |
| 29.7 |

In still other embodiments, Form A of Compound 1 is characterized in that it has substantially all of the peaks in its XRPD pattern listed in Table 1B, below.

TABLE 1B

| XRPD Peaks for Form A | |
| --- | --- |
| Peak No. | °2θ |
| 1 | 9.42 |
| 2 | 11.56 |
| 3 | 13.44 |
| 4 | 13.98 |
| 5 | 15.52 |
| 6 | 16.4 |
| 7 | 17.3 |
| 8 | 17.78 |
| 9 | 19.42 |
| 10 | 20.06 |
| 11 | 20.82 |
| 12 | 21.9 |
| 13 | 22.3 |
| 14 | 23.34 |
| 15 | 24.42 |
| 16 | 24.84 |
| 17 | 25.82 |
| 18 | 26.38 |
| 19 | 27 |
| 20 | 27.64 |
| 21 | 28.62 |
| 22 | 29.16 |
| 23 | 29.7 |
| 24 | 30.04 |
| 25 | 30.5 |
| 26 | 31.1 |
| 27 | 31.5 |
| 28 | 32.28 |
| 29 | 32.96 |
| 30 | 34.34 |
| 31 | 35.1 |
| 32 | 36 |
| 33 | 36.88 |

TABLE 1B-continued

| XRPD Peaks for Form A | |
| --- | --- |
| Peak No. | °2θ |
| 34 | 38.16 |
| 35 | 39.04 |
| 36 | 39.48 |

In certain embodiments of the present invention, Form A of Compound 1 is characterized in that it has substantially all of the peaks in its XRPD pattern, calculated from single crystal data collected at a temperature of 150±1° K, listed in Table 1C, below.

TABLE 1C

| Calculated XRPD Peaks for a Single Crystal of Form A at 150 ± 1° K | |
| --- | --- |
| Peak No. | °2θ |
| 1 | 9.5 |
| 2 | 11.35 |
| 3 | 11.75 |
| 4 | 13.3 |
| 5 | 13.6 |
| 6 | 13.9 |
| 7 | 15.3 |
| 8 | 16.85 |
| 9 | 17.35 |
| 10 | 17.95 |
| 11 | 19.5 |
| 12 | 20.3 |
| 13 | 20.65 |
| 14 | 21.15 |
| 15 | 21.8 |
| 16 | 22.75 |
| 17 | 23 |
| 18 | 23.3 |
| 19 | 23.65 |
| 20 | 23.85 |
| 21 | 24.7 |
| 22 | 24.95 |
| 23 | 26.05 |
| 24 | 26.35 |
| 25 | 26.75 |
| 26 | 27.2 |
| 27 | 28.35 |
| 28 | 29.25 |
| 29 | 29.65 |
| 30 | 30.1 |
| 31 | 31.1 |
| 32 | 31.25 |
| 33 | 31.8 |
| 34 | 32.05 |
| 35 | 32.55 |
| 36 | 33.4 |
| 37 | 34.3 |
| 38 | 34.75 |

Figure 1B:
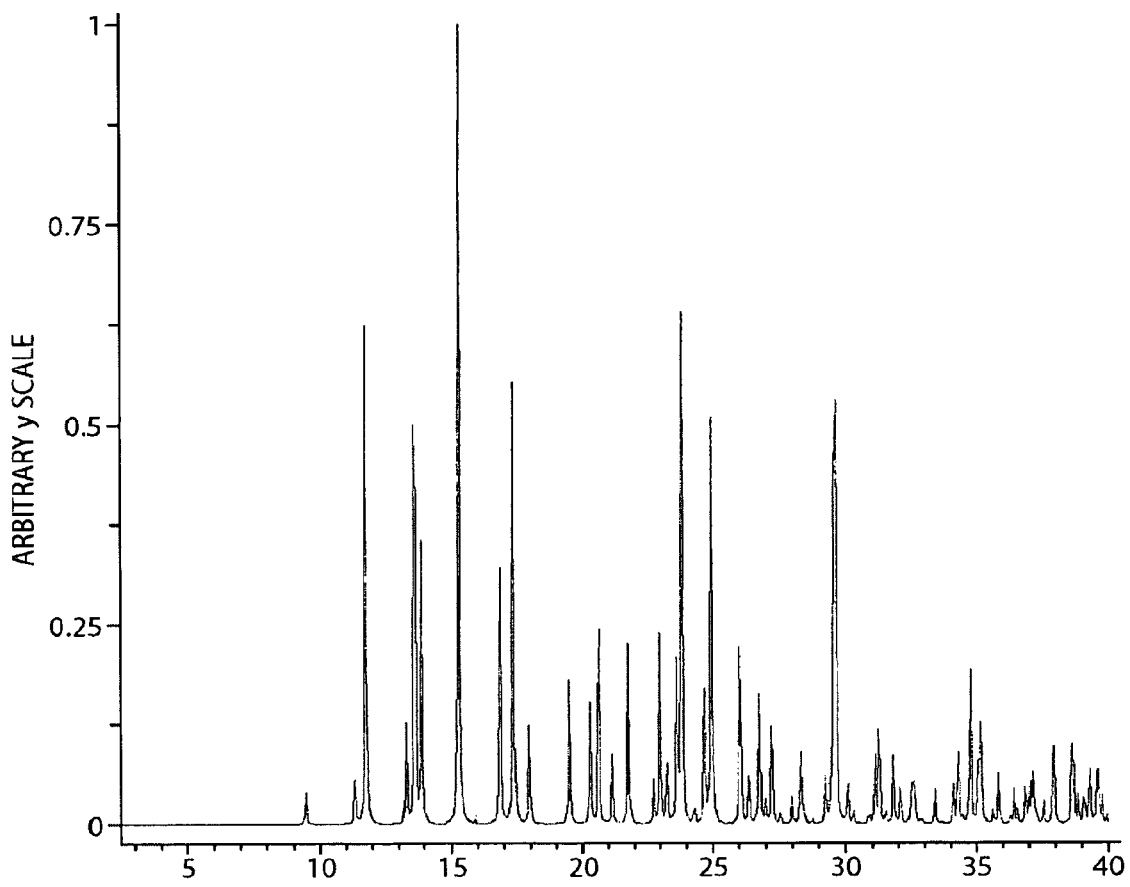
FIG. 1B depicts the X-Ray Powder Diffraction pattern for Form A, calculated for single crystal data collected at a temperature of 150±1 degrees K.
Figure 2:
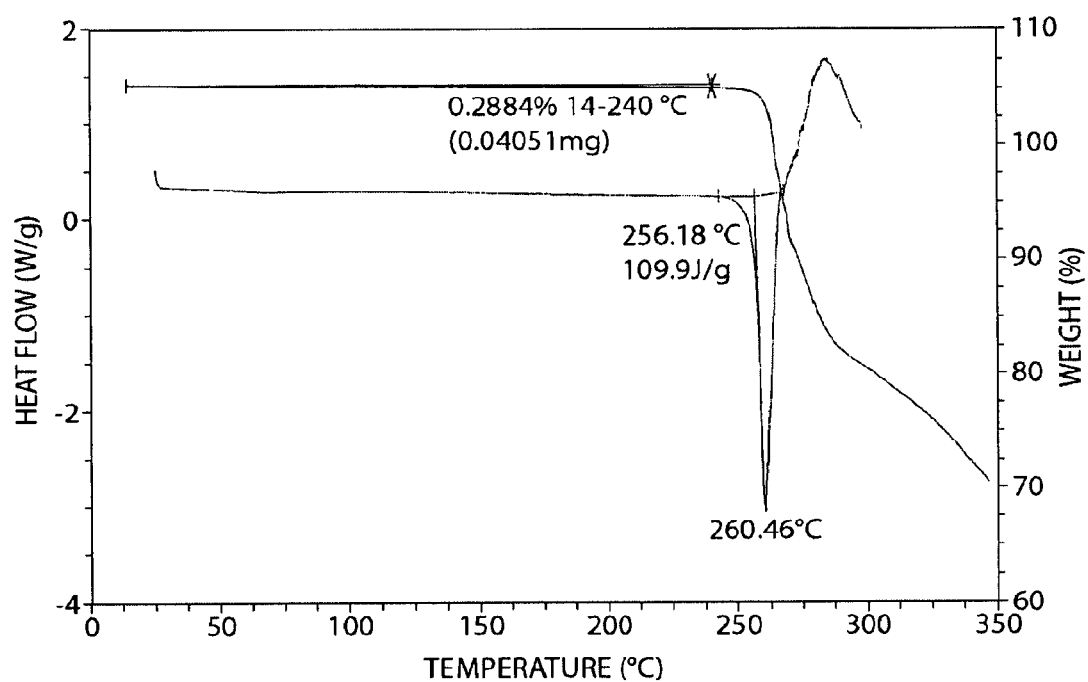
FIG. 2 depicts the DSC and TG overlay for Form A.

According to one aspect, Form A of Compound 1 has an XRPD pattern substantially similar to that depicted in FIG. 1A. As used herein, the phrase "substantially all of the peaks" means that the compound exhibits, in its XRPD, at least about 80% of the peaks listed. In other embodiments, the phrase "substantially all of the peaks" means that the compound exhibits, in its XRPD, at least about 85, 90, 95, 97, 98, or 99% of the peaks listed. According to other embodiments, Form A of Compound 1, has an XRPD pattern, calculated from single crystal data collected at a temperature of 150±1° K, substantially similar to that depicted in FIG. 1B. In other embodiments, Form A is characterized in that it has a DSC pattern substantially similar to that depicted in FIG. 2.

In certain embodiments of the invention, Form A is characterized by representative peaks in X-ray powder diffraction, which peaks are determined by comparison of X-ray diffraction pattern results for standard preparations of Form B, Form C, and Form D. In some embodiments, Form A is characterized by representative peaks in X-ray powder diffraction, which peaks are within the range of about 1 to about 30 degrees 2-theta, determined by comparison of X-ray diffraction pattern results for standard preparations of Form B, Form C, and Form D. Methods for preparing Form A of Compound 1 are described in the Examples section, infra.

Figure 3:
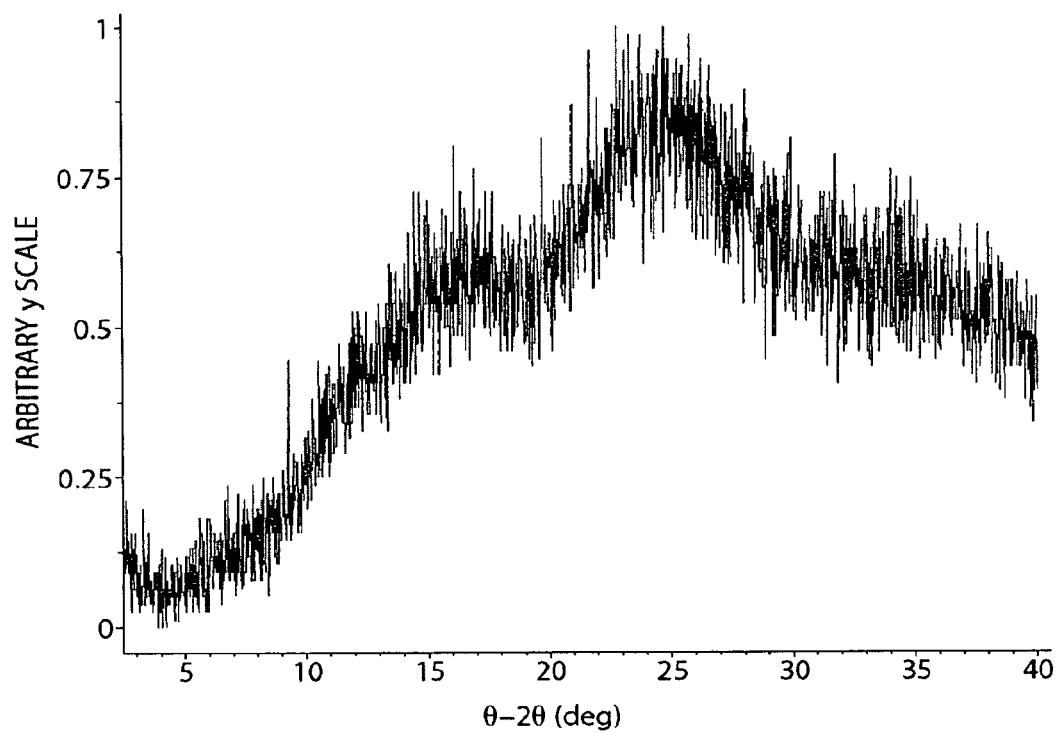
FIG. 3 depicts the X-Ray Powder Diffraction pattern for amorphous Compound 1.

According to another embodiment, the present invention provides Compound 1 as an amorphous solid. The X-ray powder diffraction pattern of amorphous Compound 1 is depicted in FIG. 3. Amorphous solids are well known to one of ordinary skill in the art and are typically prepared by such methods as lyophilization, melting, and precipitation from supercritical fluid, among others. Methods of preparing amorphous Compound 1 are described in the Examples section, infra.

In certain embodiments, the present invention provides amorphous Compound 1 substantially free of crystalline Compound 1. As used herein, the term "substantially free of crystalline. Compound 1" means that the compound contains no significant amount of crystalline Compound 1. Crystalline Compound 1 includes neat crystal forms, solvates and hydrates as described herein or other crystalline forms of Compound 1 that may result from the preparation of, and/or isolation of, amorphous Compound 1. In certain embodiments of the present invention, at least about 95% by weight of Compound 1 present is amorphous Compound 1. In still other embodiments of the invention, at least about 99% by weight of Compound 1 present is amorphous Compound 1.

In other embodiments, the present invention provides a composition comprising amorphous Compound 1 and at least one crystalline form of Compound 1. Such crystalline forms of Compound 1 include neat crystal forms, solvates and hydrates as described herein or other crystalline forms of Compound 1 that may result from the preparation of and/or isolation of, amorphous Compound 1. In certain embodiments, the present invention provides a composition comprising amorphous Compound 1 and at least one crystalline form of Compound 1 as described herein. In other embodiments, the present invention provides a composition comprising amorphous Compound 1 and at least one crystalline form of Compound 1 selected from Form A, Form B, Form C, or Form D.

It has been found that Compound 1 can exist in at least two hydrate forms or mixed hydrate-solvate forms. Two such forms are referred to herein as Form B and Form D.

In certain embodiments, the present invention provides Form B of Compound 1. In certain embodiments, the present invention provides Form B of Compound 1, substantially free of other forms of Compound 1. In other embodiments, Form B is a mixed hydrate-methanolate of Compound 1. According to one embodiment, Form B is characterized in that it has one or more peaks in its XRPD pattern selected from those at about 7.9, 8.18, 20.3, 21.44, 24.11, and 25.12 degrees 2-theta. In certain embodiments, Form B is characterized in that it has two or more, or three or more, peaks in its XRPD pattern selected from those at about 7.9, 8.18, 20.3, 21.44, 24.11, and 25.12 degrees 2-theta. In other embodiments, Form B is characterized in that it has substantially all of the peaks in its XRPD pattern selected from those at about 7.9, 8.18, 20.3, 21.44, 24.11, and 25.12 degrees 2-theta.

In certain embodiments, Form B of Compound 1 is characterized in that is has substantially all of the peaks in its XRPD pattern listed in Table 2A, below.

TABLE 2A

| XRPD Peaks for Form B Form B (°2θ) |
|---|
| 7.9 |
| 8.18 |
| 10.64 |
| 11.57 |
| 12.68 |
| 13.44 |
| 13.89 |
| 14.38 |
| 15.42 |
| 16.01 |
| 16.39 |
| 17.18 |
| 19.89 |
| 20.79 |
| 21.44 |
| 21.9 |
| 23.35 |
| 24.49 |
| 24.87 |
| 25.53 |
| 29.17 |

In still other embodiments, Form B of Compound 1 is characterized in that is has substantially all of the peaks in its XRPD pattern listed in Table 2B, below.

TABLE 2B

| XRPD Peaks for Form B | |
|---|---|
| Peak No. | °2θ |
| 1 | 7.9 |
| 2 | 8.18 |
| 3 | 10.64 |
| 4 | 11.57 |
| 5 | 12.68 |
| 6 | 13.44 |
| 7 | 13.89 |
| 8 | 14.38 |
| 9 | 15.42 |
| 10 | 16.01 |
| 11 | 16.39 |
| 12 | 17.18 |
| 13 | 17.74 |
| 14 | 18.12 |
| 15 | 18.47 |
| 16 | 19.37 |
| 17 | 19.89 |
| 18 | 20.3 |
| 19 | 20.79 |
| 20 | 21.44 |
| 21 | 21.9 |
| 22 | 22.31 |
| 23 | 23.35 |
| 24 | 24.11 |
| 25 | 24.49 |
| 26 | 24.87 |
| 27 | 25.12 |
| 28 | 25.53 |
| 29 | 26.33 |
| 30 | 26.78 |
| 31 | 27.51 |
| 32 | 28.1 |
| 33 | 29.17 |
| 34 | 29.69 |
| 35 | 30.07 |
| 36 | 30.76 |
| 37 | 31.04 |
| 38 | 32.18 |
| 39 | 32.88 |
| 40 | 34.33 |

Figure 4:
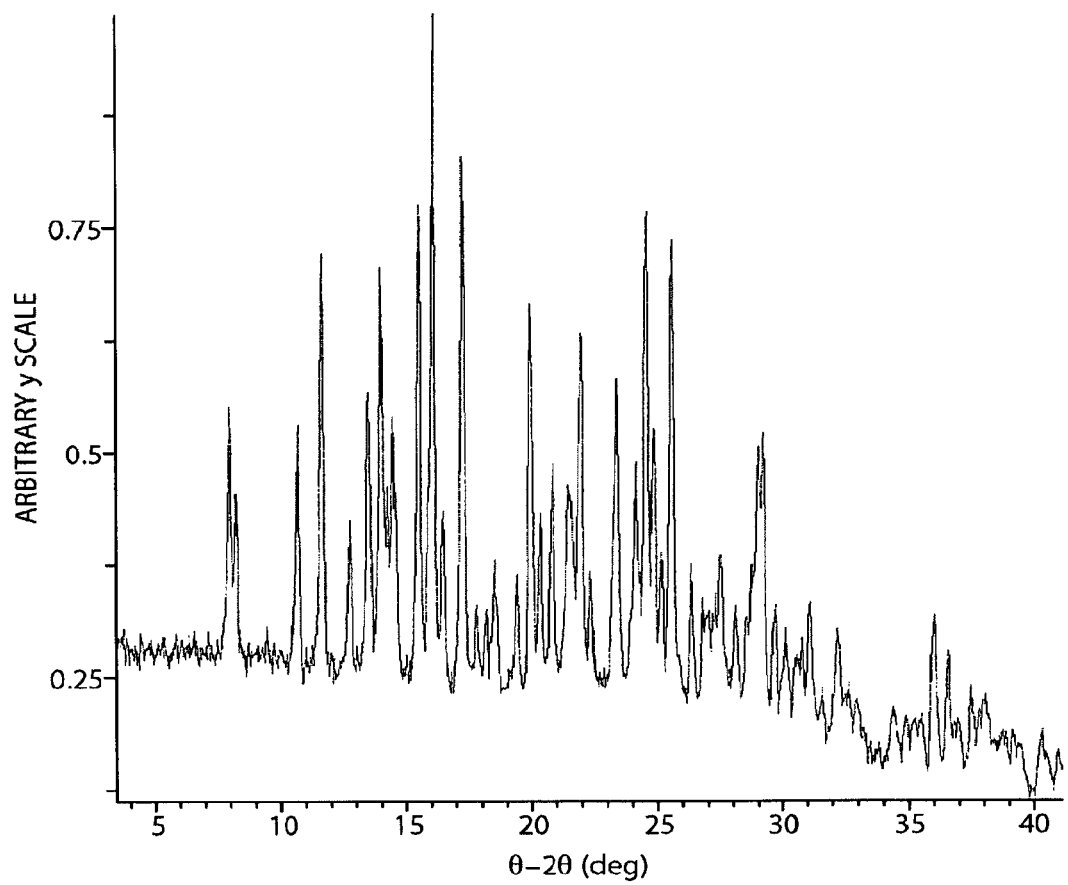
FIG. 4 depicts the X-Ray Powder Diffraction pattern for Form B.

According to one aspect, Form B of Compound has an XRPD pattern substantially similar to that depicted in FIG. 4.

Figure 5:
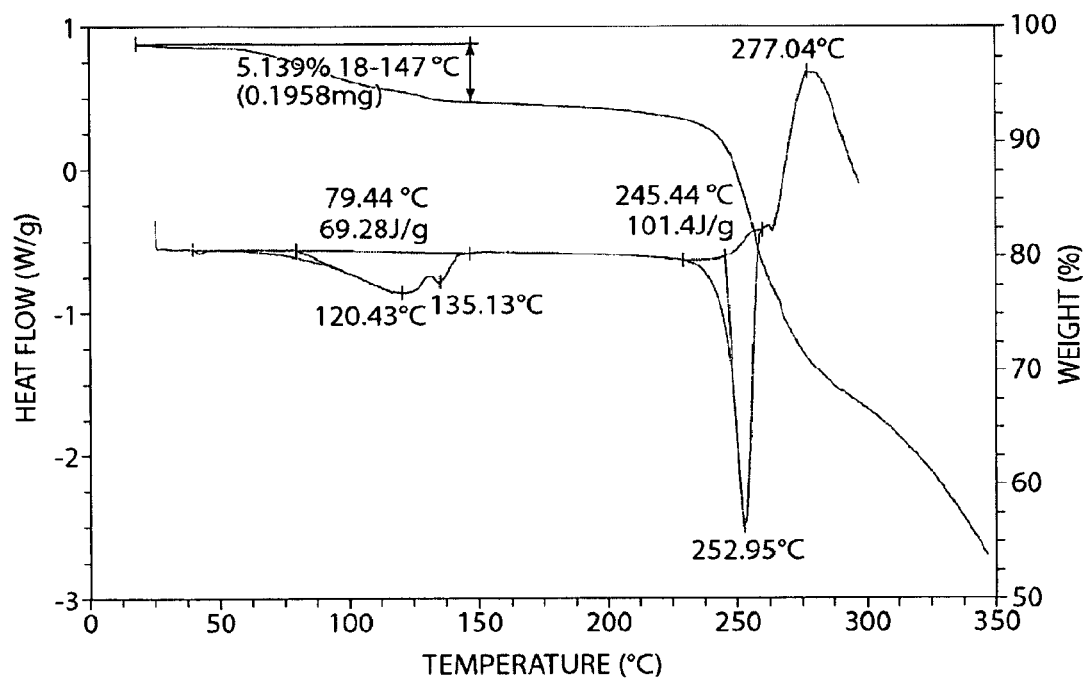
FIG. 5 depicts the DSC and TG overlay for Form B.

In other embodiments, the present invention provides Form B of Compound 1 having a DSC pattern substantially similar to that depicted in FIG. 5.

In certain embodiments of the invention, Form B is characterized by representative peaks in X-ray powder diffraction, which peaks are determined by comparison of X-ray diffraction pattern results for standard preparations of Form A, Form C, and Form D. In some embodiments, Form B is characterized by representative peaks in X-ray powder diffraction, which peaks are within the range of about 1 to about 30 degrees 2-theta, determined by comparison of X-ray diffraction pattern results for standard preparations of Form A, Form C, and Form D. Methods for preparing Form B of Compound 1 are described in the Examples section, infra.

In certain embodiments, the present invention provides Form D of Compound 1. In other embodiments, the present invention provides Form D of Compound 1, substantially free of other forms of Compound 1. According to one embodiment, Form D is characterized in that it has one or more peaks in its XRPD pattern selected from those at about 7.66, 8.42, 14.79, and 21.06 degrees 2-theta. In certain embodiments, Form D is characterized in that it has two or more, or three or more, peaks in its XRPD pattern selected from those at about 7.66, 8.42, 14.79, and 21.06 degrees 2-theta. In other embodiments, Form B is characterized in that it has substantially all of the peaks in its XRPD pattern selected from those at about 7.66, 8.42, 14.79, and 21.06 degrees 2-theta.

In certain embodiments, Form B of Compound 1 is characterized in that is has substantially all of the peaks in its XRPD pattern listed in Table 3A, below.

TABLE 3A

| XRPD Peaks for Form D Form D (°2θ) |
| --- |
| 7.66 |
| 8.42 |
| 12.85 |
| 13.48 |
| 16.11 |
| 17.53 |
| 18.67 |
| 19.61 |
| 21.06 |
| 21.79 |
| 22.07 |
| 23.25 |
| 24.53 |
| 26.23 |

In still other embodiments, Form D of Compound 1 is characterized in that is has substantially all of the peaks in its XRPD pattern listed in Table 3B, below.

TABLE 3B

| XRPD Peaks for Form D | |
| --- | --- |
| Peak No. | °2θ |
| 1 | 7.66 |
| 2 | 8.42 |
| 3 | 9.43 |
| 4 | 10.6 |
| 5 | 11.57 |
| 6 | 12.85 |
| 7 | 13.48 |
| 8 | 13.89 |
| 9 | 14.17 |
| 10 | 14.38 |
| 11 | 14.79 |
| 12 | 15.38 |
| 13 | 16.11 |
| 14 | 17.22 |
| 15 | 17.53 |
| 16 | 18.67 |
| 17 | 19.61 |
| 18 | 20.79 |
| 19 | 21.06 |
| 20 | 21.79 |
| 21 | 22.07 |
| 22 | 23.25 |
| 23 | 24.53 |
| 24 | 25.43 |
| 25 | 25.91 |
| 26 | 26.23 |
| 27 | 27.2 |
| 28 | 27.71 |
| 29 | 28.06 |
| 30 | 28.55 |
| 31 | 29.03 |
| 32 | 29.86 |
| 33 | 30.56 |
| 34 | 31.11 |
| 35 | 32.22 |
| 36 | 32.7 |
| 37 | 34.12 |
| 38 | 34.89 |
| 39 | 35.82 |
| 40 | 37 |
| 41 | 37.86 |
| 42 | 38.11 |
| 43 | 38.63 |
| 44 | 39.46 |

Figure 6:
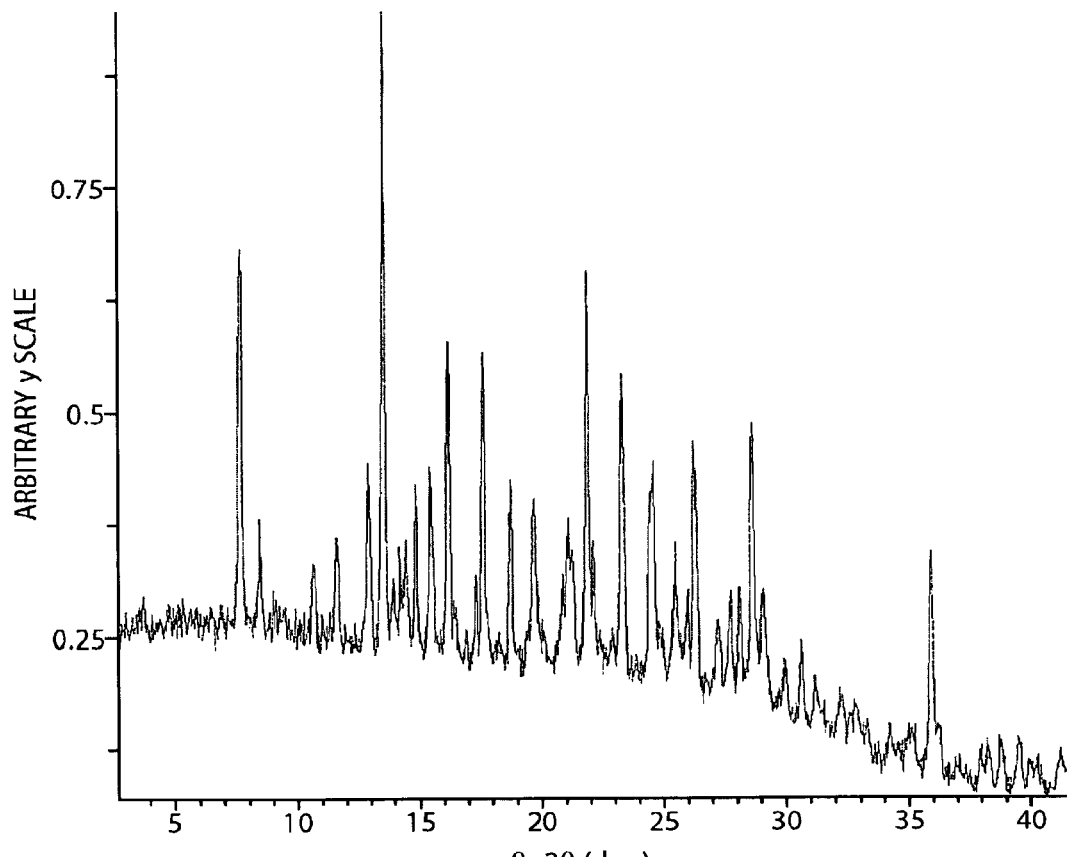
FIG. 6 depicts the X-Ray Powder Diffraction pattern for Form D.
Figure 7:
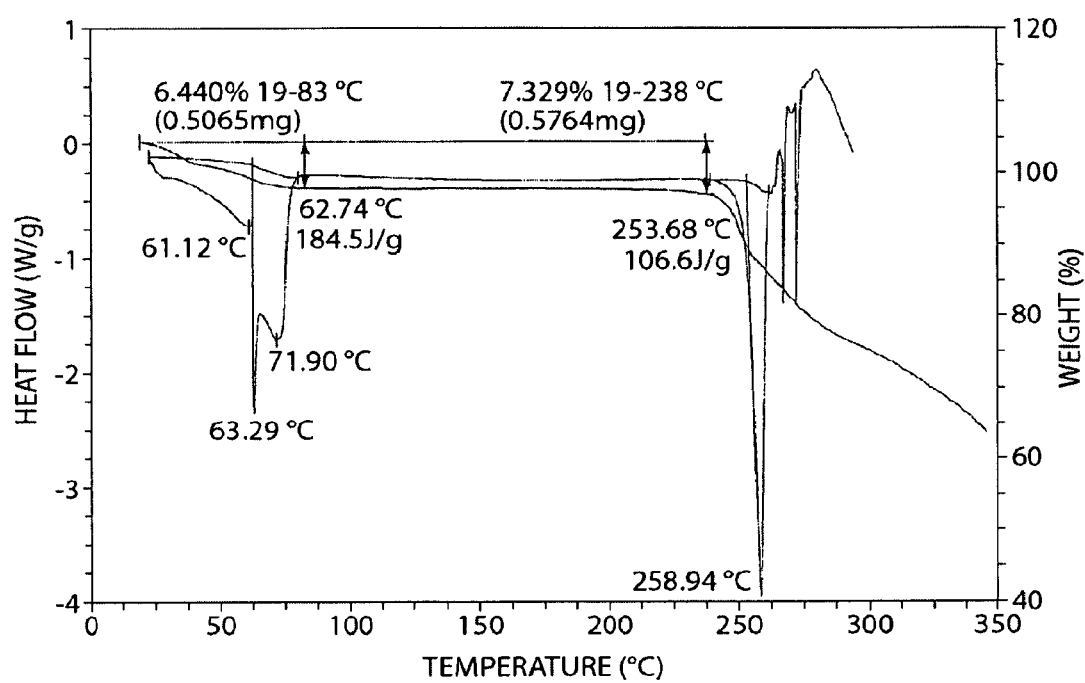
FIG. 7 depicts the DSC and TG overlay for Form D.

According to one aspect, Form D of Compound 1 has an XRPD pattern substantially similar to that depicted in FIG. 6. In other embodiments, the present invention provides Form D of Compound 1 having a DSC pattern substantially similar to that depicted in FIG. 7.

In certain embodiments of the invention, Form D is characterized by representative peaks in X-ray powder diffraction, which peaks are determined by comparison of X-ray diffraction pattern results for standard preparations of Form A, Form B, and Form C. In some embodiments, Form D is characterized by representative peaks in X-ray powder diffraction, which peaks are within the range of about 1 to about 30 degrees 2-theta, determined by comparison of X-ray diffraction pattern results for standard preparations of Form A, Form B, and Form C. Methods for preparing Form D of Compound 1 are described in the Examples section, infra.

It has been found that Compound 1 can exist in solvated crystalline forms. In certain embodiments, the present invention provides a crystalline n-propanolate of Compound 1, referred to herein as Form C. In certain embodiments, the present invention provides Form C of Compound 1, substantially free of other forms of Compound 1. According to another embodiment, Form C of Compound 1 is characterized in that it has one or more peaks in its calculated MUD pattern, for single crystal data collected at a temperature of 150±1° K, selected from those at about 10.8, 12.8, 14.8, 15.9, 16.25, 18.5, 19.15, 22, 23.6, 24.25, 25.7, 27.5, 28.1, 28.9, 31.5, and 31.75 degrees 2-theta. In certain embodiments, Form C of Compound 1 is characterized in that it has two or more, or three or more, peaks in its calculated XRPD pattern, for single crystal data collected at a temperature of 150±1° K, selected from those at about 10.8, 12.8, 14.8, 15.9, 16.25, 18.5, 19.15, 22, 23.6, 24.25, 25.7, 27.5, 28.1, 28.9, 31.5, and 31.75 degrees 2-theta. In other embodiments, Form C of Compound 1 is characterized in that it has substantially all of the peaks in its calculated XRPD pattern, for single crystal data collected at a temperature of 150±1° K, selected from those at about 10.8, 12.8, 14.8, 15.9, 16.25, 18.5, 19.15, 22, 23.6, 24.25, 25.7, 27.5, 28.1, 28.9, 31.5, and 31.75 degrees 2-theta.

In certain embodiments of the present invention, Form C of Compound 1 is characterized in that it has substantially all of the peaks in its XRPD pattern, calculated from single crystal data collected at a temperature of 150±1° K, listed in Table 4A, below.

TABLE 4A

XRPD Peaks Calculated for a Single Crystal of Form C at 150 ± 1° K

| Peak No. | °2θ |
| --- | --- |
| 1 | 9.1 |
| 2 | 10.8 |
| 3 | 11.4 |
| 4 | 11.6 |
| 5 | 12.8 |
| 6 | 14.35 |
| 7 | 14.8 |
| 8 | 15.5 |
| 9 | 15.9 |
| 10 | 16.25 |
| 11 | 18.25 |
| 12 | 18.5 |
| 13 | 18.85 |
| 14 | 19.15 |
| 15 | 19.7 |
| 16 | 20.85 |
| 17 | 21.2 |
| 18 | 21.65 |
| 19 | 21.85 |
| 20 | 22 |
| 21 | 22.65 |
| 22 | 22.95 |
| 23 | 23.3 |
| 24 | 23.6 |
| 25 | 24.25 |
| 26 | 25.05 |
| 27 | 25.3 |
| 28 | 25.7 |
| 29 | 26 |
| 30 | 27.05 |
| 31 | 27.5 |
| 32 | 28.1 |
| 33 | 28.9 |
| 34 | 29.5 |
| 35 | 29.9 |
| 36 | 30.45 |
| 37 | 30.75 |
| 38 | 31.5 |
| 39 | 31.75 |
| 40 | 32.15 |

In other embodiments, the present invention provides a composition comprising a mixture of Forms A and C of Compound 1. According to another embodiment, the XRPD pattern of the mixture of Forms A and C (preferred orientation) of Compound 1 has one or both peaks at about 10.58 and 22.74 degrees 2-theta. One of ordinary skill in the art will recognize that the designation of "preferred orientation" refers to a phenomenon that occurs when crystals have a tendency to align during the process of collecting XRPD data. This phenomenon often results in the formation of larger peaks in the XRPD pattern, as would be recognized by a skilled practitioner. In certain embodiments of the present invention, the XRPD pattern of the mixture of Forms A and C (preferred orientation) of Compound 1 has substantially all of the peaks at about 10.58, 11.56, 13.88, 15.42, 20.82, 21.86, 22.74, 23.2, 24.74, and 26.96 degrees 2-theta.

In other embodiments, the XRPD pattern of the mixture of Forms A and C (preferred orientation) of Compound 1 has substantially all of the peaks in its XRPD pattern listed in Table 4B, below.

TABLE 4B

XRPD Peaks for Forms A and C (preferred orientation)

| Peak No. | °2θ |
| --- | --- |
| 1 | 10.58 |
| 2 | 11.56 |
| 3 | 13.44 |
| 4 | 13.88 |
| 5 | 15.42 |
| 6 | 16.4 |
| 7 | 18.88 |
| 8 | 19.34 |
| 9 | 19.9 |
| 10 | 20.82 |
| 11 | 21.86 |
| 12 | 22.22 |
| 13 | 22.74 |
| 14 | 23.2 |
| 15 | 23.84 |
| 16 | 24.74 |
| 17 | 25.7 |
| 18 | 26.96 |
| 19 | 28.7 |
| 20 | 29.14 |
| 21 | 29.64 |
| 22 | 34.02 |
| 23 | 34.66 |
| 24 | 35.08 |
| 25 | 35.98 |
| 26 | 37.14 |
| 27 | 38.32 |
| 28 | 39.24 |

Figure 8:
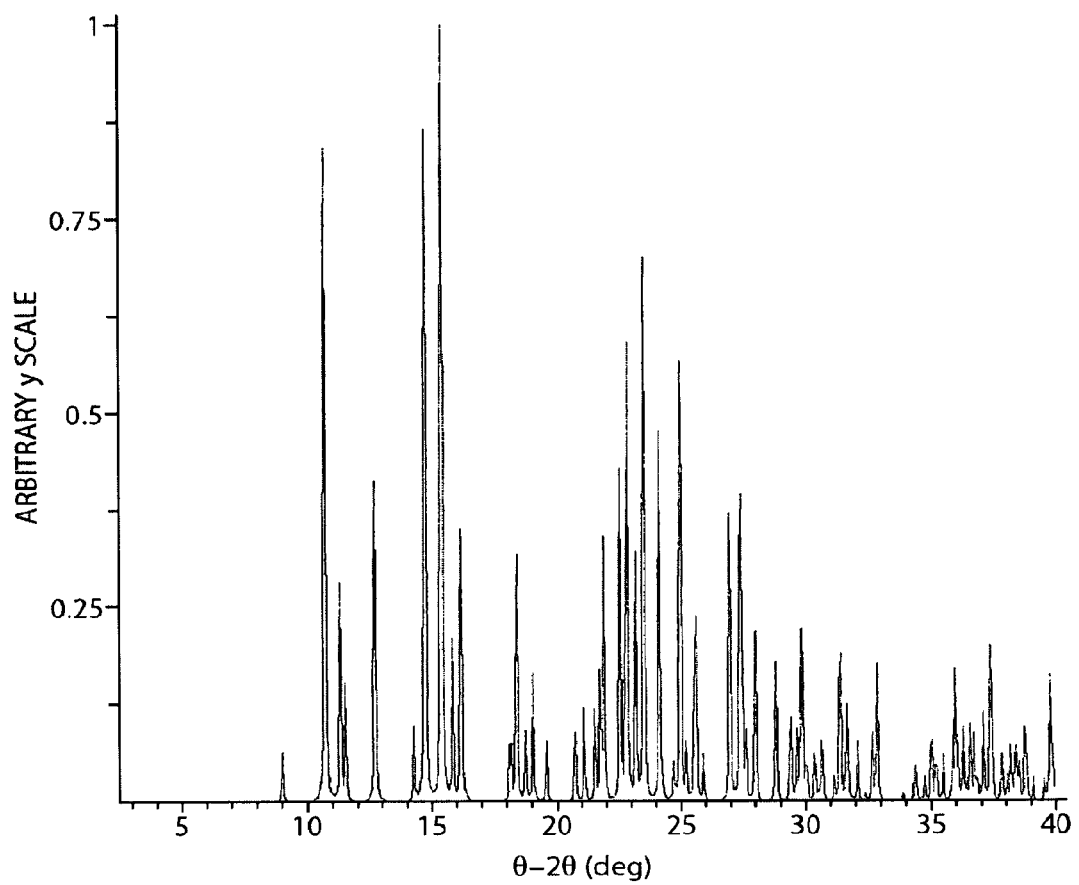
FIG. 8 depicts the X-Ray Powder Diffraction pattern for Form C, calculated for single crystal data collected at a temperature of 150±1 degrees K.
Figure 9:
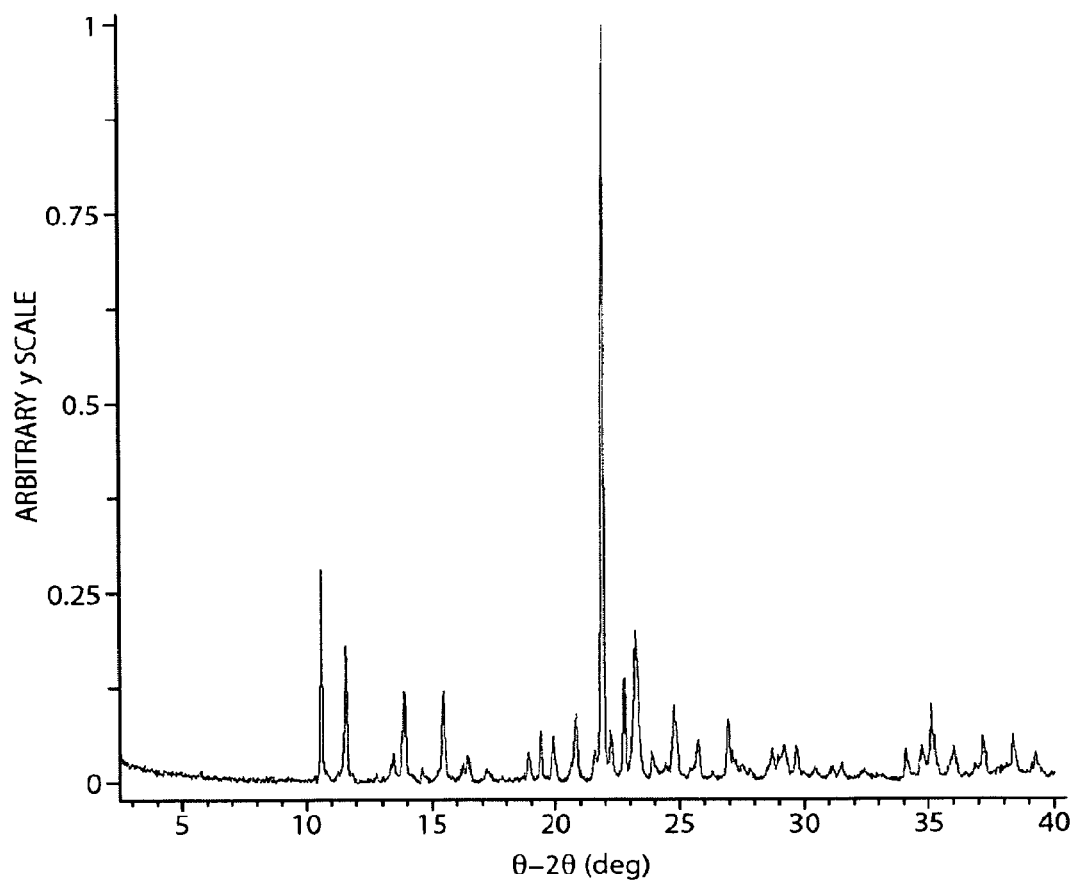
FIG. 9 depicts the X-Ray Powder Diffraction pattern for a mixture of Form A+Form C (preferred orientation).

According to one aspect, Form C of Compound 1 has an XRPD pattern, calculated from single crystal data collected at a temperature of 150±1° K, substantially similar to that depicted in FIG. 8. According to another aspect, a mixture of Forms A and C (preferred orientation) of Compound 1 has an XRPD pattern substantially similar to that depicted in FIG. 9.

In certain embodiments of the invention, Form C is characterized by representative peaks in X-ray powder diffraction, which peaks are determined by comparison of X-ray diffraction pattern results for standard preparations of Form A, Form B, and Form D. In some embodiments, Form C is characterized by representative peaks in X-ray powder diffraction, which peaks are within the range of about 1 to about 30 degrees 2-theta, determined by comparison of X-ray diffraction pattern results for standard preparations of Form A, Form B, and Form D. Methods for preparing Form C of Compound 1 are described in the Examples section, infra.

In certain embodiments, the present invention provides Form A of Compound 1 comprising one or more additional solid forms of Compound 1. In other embodiments, the present invention provides Form A of Compound 1 comprising one or more of a hydrate of Compound 1, a solvate of Compound 1, or amorphous compound 2. In still other embodiments, the present invention provides Form A of Compound 1 comprising one or more of Form C, Form D, or amorphous, and optionally Form B. Thus, another aspect of the present invention provides a Compound 1 Composition.

As used herein, the term "Compound 1 Composition" refers to a composition comprising at least two of Form A, Form C, Form D, and amorphous Compound 1, and optionally Form B. In other embodiments, the Compound 1 Composition comprises at least two of Form B, Form C, Form F), and amorphous Compound 1. In certain embodiments of the invention, the Compound 1. Composition comprises Form A of Compound 1 and Form D. In still other embodiments, the Compound 1 Composition comprises Form A and amorphous Compound 1.

Pharmaceutically Acceptable Compositions

As discussed above, the present invention provides new forms of Compound 1, which is useful as a peripheral mu opioid receptor antagonist and shows utility in clinically relevant models for treating opioid-induced side effects. According to another aspect of the present invention, pharmaceutically acceptable compositions are provided, comprising an inventive form of Compound 1, or a Compound 1 Composition, as described herein, and optionally comprising a pharmaceutically acceptable carrier, adjuvant, or vehicle. In certain embodiments of the present invention, such pharmaceutically acceptable compositions optionally further comprise one or more additional therapeutic agents.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with an inventive form of Compound 1, or Compound 1 Composition, of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

DEFINITIONS

As used herein, an "effective amount" of a compound or pharmaceutically acceptable composition can achieve a desired therapeutic and/or prophylactic effect. An "effective amount" is at least a minimal amount of a compound, or composition containing a compound, which is sufficient for preventing, ameliorating, reducing, delaying, or diminishing severity of one or more symptoms of a disorder associated with modulation of peripheral μ opioid receptors, and/or for preventing, ameliorating, delaying or diminishing severity of side effects associated with opioid analgesic therapy (e.g., gastrointestinal dysfunction (e.g., dysmotility constipation, etc.), nausea, emesis, (e.g., nausea), etc.). An "effective amount" of a compound, or composition containing a compound, is sufficient for prevention, amelioration, reduction, delay or a decrease in the symptoms associated with, a disease associated with aberrant endogenous peripheral opioid or μ opioid receptor activity (e.g., idiopathic constipation, ileus, etc.).

The term "formulation" refers to a preparation that includes an inventive form of Compound 1, or Compound 1 Composition, in combination with one or more excipients for administration to a subject. In general, particular pharmaceutical additives are selected with the aim of enabling an optimal release, distribution and development of activity of an inventive form of Compound 1, or Compound 1 Composition, for the respective applications.

The term "subject", as used herein, means a mammal and includes human and animal subjects, such as domestic animals (e.g., horses, dogs, cats, etc.).

The expression "dosage unit form" as used herein refers to a physically discrete unit of agent appropriate for the patient to be treated.

An inventive form of Compound 1, or Compound 1 Composition, according to the present invention, may be administered using any amount and any route of administration effective for treating or lessening the severity of a disorder associated with modulation of peripheral μ opioid receptors. The exact amount required will vary from subject to subject, depending on the species, age, and general condition of the subject, the severity of the infection, the particular agent, its mode of administration, and the like. It will be understood, however, that the total daily usage of an inventive form of Compound 1, or Compound 1 Composition, will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, nasally, rectally, parenterally, intracisternally, intravaginally, intraperitoneally, topically (as by powders, ointments, or drops), bucally, or the like, depending on the severity of the infection being treated. In certain embodiments, an inventive form of Compound 1, or Compound 1 Composition, may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral or nasal administration include, but are not limited to, pharmaceutically acceptable emulsions, microemulsions, solutions, suspensions, aerosols, gels, syrups, and elixirs. In addition to an inventive form of Compound 1, or Compound 1 Composition, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a pharmaceutically acceptable propellant. The aerosol dosage forms can also take the form of a pump-atomiser.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Advantageously, amorphous Compound 1, as described herein, has enhanced water solubility. Accordingly, amorphous Compound 1 is useful for intravascular and intramuscular delivery. In certain embodiments, the present invention also relates to an injectable formulation for intravascular or intramuscular delivery.

In order to prolong the effect of an inventive form of Compound 1, or Compound 1 Composition, of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Typical parenteral compositions consist of a solution or suspension of the compound in a sterile aqueous carrier or non-aqueous or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for rectal or vaginal administration are conveniently in the form of suppositories, pessaries, vaginal tabs, foams, or enemas. Compositions for rectal or vaginal administration are preferably suppositories which can be prepared by mixing an inventive form of Compound 1, or Compound 1 Composition, with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, an inventive form of Compound 1, or Compound 1 Composition, is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium salts, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Compositions suitable for buccal or sublingual administration include tablets, lozenges and pastilles, wherein the active ingredient is formulated with a carrier such as sugar and acacia, tragacanth, or gelatin and glycerin.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

An inventive form of Compound 1, or Compound 1 Composition, can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms an inventive form of Compound 1, or Compound 1 Composition, may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the ease of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Compositions for oral administration may be designed to protect the active ingredient against degradation as it passes through the alimentary tract, for example by an outer coating of the formulation on a tablet or capsule.

In another embodiment, an inventive form of Compound 1, or Compound 1 Composition, is be provided in an extended (or "delayed" or "sustained") release composition. This delayed release composition comprises an inventive form of Compound 1, or Compound 1 Composition, in combination with a delayed release component. This composition allows targeted release of an inventive form of Compound 1, or Compound 1 Composition, into the lower gastrointestinal tract; for example into the small intestine, the large intestine, the colon and/or the rectum. In certain embodiments, the delayed release composition comprising an inventive form of Compound 1, or Compound 1 Composition, further comprises an enteric or pH dependent coating such as cellulose acetate phthalates and other phthalates (e.g. polyvinyl acetate phthalate, methacrylates (Eudragits)). Alternatively, the delayed release composition provides controlled release to the small intestine and/or colon by the provision of pH sensitive methacrylate coatings, pH sensitive polymeric microspheres, or polymers which undergo degradation by hydrolysis. The delayed release composition can be formulated with hydrophobic or gelling excipients or coatings. Colonic delivery can further be provided by coatings which are digested by bacterial enzymes such as amylose or pectin, by pH dependent polymers, by hydrogel plugs swelling with time (Pulsincap), by time dependent hydrogel coatings and/or by acrylic acid linked to azoaromatic bonds coatings.

In certain embodiments, the delayed release compositions of the present invention comprise hypromellose, microcrystalline cellulose, and a lubricant. The mixture of an inventive form of Compound 1, or Compound 1 Composition, hypromellose and microcrystalline cellulose may be formulated into a tablet or capsule for oral administration, in certain embodiments, the mixture is granulated and pressed into tablets.

In other embodiments, the delayed release compositions of the present invention are provided in a multiparticulate formulation. A mixture of an inventive form of Compound 1, or Compound 1 Composition, and a suitable polymer is granulated to form pellets which are coated. In certain embodiments, the pellets are seal coated with a non-functional coating. In other embodiments, the pellets are first seal coated with a non-functional coating and then coated with a functional coating.

As used herein the term "non-functional coating" is a coating that does not effect the release rate of the drug. Examples of a non-functional coat include hydroxypropyl cellulose, hypromellose or polyvinyl alcohol. In certain embodiments, the non-functional coating is Opadry® Clear, which contains, hydroxypropyl methylcellulose and polyethylene glycol.

As used herein, the term "functional coating" is a coating that affects the release rate of the drug from the dosage form. Examples of a functional coating include ethylcellulose and polymethacrylate derivatives (Eudragits).

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any deeded preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions may contain from 0.1% to 99% (w/w) preferably from 0.1-60% (w/w), more preferably 0.2-20% by weight and most preferably 0.25 to 12% (w/w) of an inventive form of Compound 1, or Compound 1 Composition, depending on the method of administration.

Combination Products and Combined Administration

In certain embodiments, an inventive form of Compound 1, or Compound 1 Composition, may be administered alone to treat one or more disorders as described herein, or alternatively may be administered in combination with (whether simultaneously or sequentially) one or more other active agents useful to treat one or more disorders as described herein. Thus, an inventive composition, or formulation thereof, can be administered concurrently with, prior to, or subsequent to, one or inure active agents.

In certain embodiments, inventive compositions include one or more other active agents in addition to an inventive form of Compound 1, or Compound/Composition, that is not an inventive form of Compound 1, or Compound 1 Composition. In certain embodiments, the present invention provides a formulation that delivers an inventive form of Compound 1, or Compound 1 Composition, and at least one additional active agent.

In some embodiments, inventive formulations comprise both an opioid and an inventive form of Compound 1, or Compound 1. Composition. Such combination products, containing both an opioid and an inventive form of Compound 1, or Compound 1 Composition, would allow simultaneous relief of pain and minimization of opioid-associated side effects (e.g., gastrointestinal effects (e.g., delayed gastric emptying, altered GI tract motility), etc.).

Opioids useful in treatment of analgesia are known in the art. For example, opioid compounds include, but are not limited to, alfentanil, anileridine, asimadoline, bremazocine, buprenorphine, butorphanol, codeine, dezocine, diacetylmorphine (heroin), dihydrocodeine, diphenoxylate, ethylmorphine, fedotozine, fentanyl, funaltrexamine, hydrocodone, hydromorphone, levallorphan, levomethadyl acetate, levorphanol, loperamide, meperidine (pethidine), methadone, morphine, morphine-6-glucoronide, nalbuphine, nalorphine, nicomorphine, opium, oxycodone, oxymorphone, papaveretum, pentazocine, propiram, propoxyphene, remifentanyl, sufentanil, tilidine, trimebutine, and tramadol. In some embodiments the opioid is at least one opioid selected from alfentanil, buprenorphine, butorphanol, codeine, dezocine, dihydrocodeine, fentanyl, hydrocodone, hydromorphone, levorphanol, meperidine (pethidine), methadone, morphine, nalbuphine, nicomorphine, oxycodone, oxymorphone, papaveretum, pentazocine, propiram, propoxyphene, sufentanil and/or tramadol. In certain embodiments of the present invention, the opioid is selected from morphine, codeine, oxycodone, hydrocodone, dihydrocodeine, propoxyphene, fentanyl, tramadol, and mixtures thereof. In a particular embodiment, the opioid is loperamide. In other embodiments, the opioid is a mixed agonist such as butorphanol. In some embodiments, the subjects are administered inure than one opioid, for example, morphine and heroin or methadone and heroin.

The amount of additional active agents) present in combination compositions of this invention will typically be no more than the amount that would normally be administered in a composition comprising that active agent as the only therapeutic agent. In certain embodiments of the present invention, the amount of additional active agent will range from about 50% to 100% of the amount normally present in a composition comprising that compound as the only therapeutic agent.

In certain embodiments, inventive formulations may also be used in conjunction with and/or in combination with conventional therapies for gastrointestinal dysfunction to aid in the amelioration of constipation and bowel dysfunction. For example, conventional therapies include, but may not be limited to functional stimulation of the intestinal tract, stool softening agents, laxatives (e.g., diphelymethane laxatives, cathartic laxatives, osmotic laxatives, saline laxatives, etc), bulk forming agents and laxatives, lubricants, intravenous hydration, and nasogastric decompression.

Uses and Kits of Inventive Formulations

As discussed above, the present invention provides inventive forms of Compound 1, or Compound 1 Compositions, and pharmaceutically acceptable compositions and formulations thereof, useful in antagonizing undesirable side effects of opioid analgesic therapy (e.g., gastrointestinal effects (e.g., delayed gastric emptying, altered GI tract motility), etc.). Furthermore, inventive forms of Compound 1, or a Compound 1 Composition, and pharmaceutically acceptable compositions and formulations thereof, may be used as to treat subjects having disease states that are ameliorated by binding μ opioid receptors, or in any treatment wherein temporary suppression of the μ opioid receptor system is desired (e.g., ileus, etc.). In certain embodiments of the present invention, methods of use of formulations are in human subjects.

Accordingly, administration of an inventive form of Compound 1, or a Compound 1 Composition, or a pharmaceutically acceptable composition or formulation thereof, may be advantageous for treatment, prevention, amelioration, delay or reduction of side effects of opioid use, such as, for example, gastrointestinal dysfunction (e.g., inhibition of intestinal motility, constipation, GI sphincter constriction, nausea, emesis (vomiting), biliary spasm, opioid bowel dysfunction, colic, dysphoria, pruritus, urinary retention, depression of respiration, papillary constriction, cardiovascular effects, chest wall rigidity and cough suppression, depression of stress response, and immune suppression associated with use of narcotic analgesia, etc, or combinations thereof. Use of an inventive form of Compound 1, or a Compound 1 Composition, or a pharmaceutically acceptable composition or formulation thereof, may thus be beneficial from a quality of life standpoint for subjects receiving opioids, as well as to reduce complications arising from chronic constipation, such as hemorrhoids, appetite suppression, mucosal breakdown, sepsis, colon cancer risk, and myocardial infarction.

In some embodiments, inventive forms of Compound 1, or Compound 1 Compositions, and pharmaceutically acceptable compositions and formulations thereof, are useful for administration to a subject receiving acute opioid administration, in some embodiments, provided formulations are useful for administration to patients suffering from post-operative gastrointestinal dysfunction.

In other embodiments, inventive forms of Compound 1, or Compound 1 Compositions, and pharmaceutically acceptable compositions and formulations thereof, are also useful for administration to subjects receiving chronic opioid administration (e.g., terminally ill patients receiving opioid therapy such as an AIDS patient, a cancer patient, a cardiovascular patient; subjects receiving chronic opioid therapy for pain management; subjects receiving opioid therapy for maintenance of opioid withdrawal). In some embodiments, the subject is a subject using opioid for chronic pain management. In some embodiments, the subject is a terminally ill patient. In other embodiments the subject is a person receiving opioid withdrawal maintenance therapy.

Alternative or additional uses for inventive forms of Compound 1, or Compound 1 Compositions, and pharmaceutically acceptable compositions and formulations thereof, described herein may be to treat, reduce, inhibit, or prevent effects of opioid use including, e.g., aberrant migration or proliferation of endothelial cells (e.g., vascular endothelial cells), increased angiogenesis, and increase in lethal factor production from opportunistic infectious agents (e.g., *Pseudomonas aeruginosa*). Additional advantageous uses of inventive forms of Compound 1, or Compound 1 Compositions, and pharmaceutically acceptable compositions and formulations thereof, include treatment of opioid-induced immune suppression, inhibition of angiogenesis, inhibition of vascular proliferation, treatment of pain, treatment of inflammatory conditions such as inflammatory bowel syndrome, treatment of infectious diseases and diseases of the musculoskeletal system such as osteoporosis, arthritis, osteitis, periostitis, myopathies, and treatment of autoimmune diseases.

In certain embodiments, inventive forms of Compound 1, or Compound 1 Compositions, and pharmaceutically acceptable compositions and formulations thereof, of the invention may be used in methods for preventing, inhibiting, reducing, delaying, diminishing or treating gastrointestinal dysfunction, including, but not limited to, irritable bowel syndrome, opioid-induced bowel dysfunction, colitis, post-operative or postpartum ileus, nausea and/or vomiting, decreased gastric motility and emptying, inhibition of the stomach, and small and/or large intestinal propulsion, increased amplitude of non-propulsive segmental contractions, constriction of sphincter of Oddi, increased anal sphincter tone, impaired reflex relaxation with rectal distention, diminished gastric, biliary, pancreatic or intestinal secretions, increased absorption of water from bowel contents, gastro-esophageal reflux, gastroparesis, cramping, bloating, abdominal or epigastric pain and discomfort, constipation, idiopathic constipation, post-operative gastrointestinal dysfunction following abdominal surgery (e.g., colectomy (e.g., right hemicolectomy, left hemicolectomy, transverse hemicolectomy, colectomy takedown, low anterior resection)), and delayed absorption of orally administered medications or nutritive substances.

Provided forms of Compound 1, or Compound 1 Compositions, and pharmaceutically acceptable compositions and formulations thereof, are also useful in treatment of conditions including cancers involving angiogenesis, immune suppression, sickle cell anemia, vascular wounds, and retinopathy, treatment of inflammation associated disorders (e.g., irritable bowel syndrome), immune suppression, chronic inflammation.

In still further embodiments, veterinary applications (e.g., treatment of domestic animals, e.g. horse, dogs, cats, etc.) of use of inventive forms of Compound 1, or Compound 1 Compositions, and pharmaceutically acceptable compositions and formulations thereof, are provided. Thus, use of provided formulations in veterinary applications analogous to those discussed above for human subjects is contemplated. For example, inhibition of equine gastrointestinal motility, such as colic and constipation, may be fatal to a horse. Resulting pain suffered by the horse with colic can result in a death-inducing shock, while a long-term case of constipation may also cause a horse's death. Treatment of equines with peripheral opioid receptor antagonists has been described, e.g., in U.S. Patent Publication No. 20050124657 published Jan. 20, 2005.

It will also be appreciated that inventive forms of Compound 1, or Compound 1 Compositions, and pharmaceutically acceptable compositions and formulations thereof, can be employed in combination therapies, that is, inventive forms of Compound 1, or Compound 1 Compositions, and pharmaceutically acceptable compositions and formulations thereof, can be administered concurrently with, prior to, or subsequent to, one or more other desired therapeutics or medical procedures. Particular combination therapies (therapeutics or procedures) to employ in a combination regimen will take into account compatibility of the desired therapeutics and/or procedures and the desired therapeutic effect to be achieved. It will also be appreciated that therapies employed may achieve a desired effect for the same disorder (for example, a formulation may be administered concurrently with another compound used to treat the same disorder), or they may achieve different effects (e.g., control of any adverse effects). As used herein, additional therapeutic compounds which are normally administered to treat or prevent a particular disease, or condition, are known as "appropriate for the disease, or condition, being treated".

In other embodiments, inventive forms of Compound 1, or Compound 1 Compositions, and pharmaceutically acceptable compositions and formulations thereof, and unit dose forms are useful in preparation of medicaments, including, but not limited to medicaments useful in the treatment of side effects of opioid use (e.g., gastrointestinal side effects (e.g., inhibition of intestinal motility, GI sphincter constriction, constipation) nausea, emesis, (vomiting), dysphoria, pruritus, etc.) or a combination thereof inventive forms of Compound 1, or Compound 1 Compositions, and pharmaceutically acceptable compositions and formulations thereof, are useful for preparations of medicaments, useful in treatment of patients receiving acute opioid therapy (e.g., patients suffering from post-operative gastrointestinal dysfunction receiving acute opioid administration) or subjects using opioids chronically (e.g., terminally ill patients receiving opioid therapy such as an AIDS patient, a cancer patient, a cardiovascular patient; subjects receiving chronic opioid therapy for pain management; or subjects receiving opioid therapy for maintenance of opioid withdrawal). Still further, preparation of medicaments useful in the treatment of pain, treatment of inflammatory conditions such as inflammatory bowel syndrome, treatment of infectious diseases, treatment of diseases of the musculoskeletal system such as osteoporosis, arthritis, osteitis, periostitis, myopathies, treatment of autoimmune diseases and immune suppression, therapy of post-operative gastrointestinal dysfunction following abdominal surgery (e.g., colectomy (e.g., right hemicolectomy, left hemicolectomy, transverse hemicolectomy, colectomy takedown, low anterior resection), idiopathic constipation, and ileus (e.g., post-operative ileus, post-partum ileus), and treatment of disorders such as cancers involving angiogenesis, chronic inflammation and/or chronic pain, sickle cell anemia, vascular wounds, and retinopathy.

Still further encompassed by the invention are pharmaceutical packs and/or kits comprising an inventive form of Compound 1, or Compound 1 Composition, or a pharmaceutically acceptable composition or formulation thereof, and a container (e.g., a foil or plastic package, or other suitable container). Optionally instructions for use are additionally provided in such kits.

In order that the invention described herein may be more fully understood, the following examples are set forth. It should be understood that these examples are for illustrative purposes only and are not to be construed as limiting this invention in any manner.

All features of each of the aspects of the invention apply to all other aspects mutatis mutandis.

EXEMPLIFICATION

General Procedures

Compound 1 is prepared according to the methods described in detail in International Patent Application publication number WO2006/127899, the entirety of which is hereby incorporated herein by reference.

X-Ray Powder Diffraction (XRPD): X-ray powder diffraction (XRPD) analyses were performed using a Shimadzu XRD-6000 X-ray powder diffractometer using Cu Kα radiation. The instrument is equipped with a long fine focus X-ray tube. The tube voltage and amperage were set to 40 kV and 40 mA, respectively. The divergence and scattering slits were set at 1° and the receiving slit was set at 0.15 mm. Diffracted radiation was detected by a NaI scintillation detector. A θ-2θ continuous scan at 3°/min (0.4 sec/0.02° step) from 2.5 to 40° 2θ was used. A silicon standard was analyzed to check the instrument alignment. Data were collected and analyzed using XRD-6100/7000 v. 5.0. Samples were prepared for analysis by placing them in an aluminum holder with silicon insert.

XRPD Pattern Analyses: X-ray powder diffraction (XRPD) analyses were performed using an Inel XRG-3000 diffractometer equipped with a CPS (Curved Position Sensitive) detector with a 2θ range of 120°. Real time data were collected using Cu-Kα radiation at a resolution of 0.03° 2θ. The tube voltage and amperage were set to 40 kV and 30 mA, respectively. The monochromator slit was set at 5 mm by 160 µm or at 2 mm by 160 µm. The pattern is displayed from 2.5-40° 2θ. Samples were prepared for analysis by packing them into thin-walled glass capillaries. Each capillary was mounted onto a goniometer head that is motorized to permit spinning of the capillary during data acquisition. The samples were analyzed for 5 min or 10 min. Instrument calibration was performed using a silicon reference standard.

XRPD Pattern Collection: XRPD patterns were collected with a Bruker D-8 Discover diffractometer and Bruker's General Area Diffraction Detection System (GADDS, v. 4.1.20). An incident beam of Cu Kα radiation was produced using a fine-focus tube (40 kV, 40 mA), a Göbel mirror, and a 0.5 mm double-pinhole collimator. A specimen of the sample was packed in a capillary and secured to a translation stage. A video camera and laser were used to position the area of interest to intersect the incident beam in transmission geometry. The incident beam was scanned to optimize orientation statistics. A beam-stop was used to minimize air scatter from the incident beam at low angles. Diffraction patterns were collected using a Hi-Star area detector located 15 cm from the sample and processed using GADDS. The intensity in the GADDS image of the diffraction pattern was integrated using a step size of 0.04° 2θ. The integrated patterns display diffraction intensity as a function of 2θ. Prior to the analysis a silicon standard was analyzed to verify the Si 111 peak position. XRPD peak listings were generated using Pattern Match software, version 2.1.1.

Differential Scanning Calorimetry ("DSC"): Differential scanning calorimetry was performed using a TA Instruments differential scanning calorimeter 2920. The sample was placed into an aluminum DSC pan, and the weight accurately recorded. The pan was covered with a lid and left uncrimped. The sample cell was heated under a nitrogen purge at a rate of 10° C./min, up to a final temperature of 250 or 300° C. Indium metal was used as the calibration standard. Reported temperatures are at the transition maxima.

Thermogravimetry ("TG"): Thermogravimetric analyses were performed using a TA Instruments 2950 thermogravimetric analyzer. Each sample was placed in an aluminum sample pan and inserted into the TG furnace. The furnace was heated under nitrogen at a rate of 10° C./min, up to a final temperature of 350° C. Nickel and AlumelÔ were used as the calibration standards.

Solution 1D $^1$H NMR Spectroscopy: The solution $^1$H NMR spectra were acquired at ambient temperature with a Varian $^{UNITY}$INOVA-400 spectrometer at a Larmor frequency of 399.796 MHz. The sample was dissolved in DMSO-$d_6$. The spectrum was acquired with a $^1$H pulse width of 8.2 µs, a 2.50 second acquisition time, a 5 second delay between scans, a spectral width of 6400 Hz with 32000 data points, and 40 co-added scans. The free induction decay (FID) was processed using Varian VNMR 6.1C software with 131072 points and an exponential line broadening factor of 0.2 Hz to improve the signal-to-noise ratio. The residual peak from incompletely deuterated DMSO is at approximately 2.50 ppm. The relatively broad peak at approximately 3.3 ppm is due to water. The spectrum was referenced to internal tetramethylsilane (TMS) at 0.0 ppm.

Example 1

Preparation of Form A

Compound 1 (54.7 mg) was dissolved in 2,2,2-trifluoroethanol (2 mL), and the solution was filtered through a 0.2 µm nylon filter into a 20-mL vial. The 20-mL vial was placed inside a 100-mL glass jar containing 5 mL of ethyl acetate. The 20-mL vial was left uncapped and the jar was capped to allow vapor diffusion to occur. After four days, single crystals were observed in solution.

The monoclinic cell parameters and calculated volume at 150° K are: a=7.9337(3) Å, b=12.7337(9) Å, c=9.4247(7) Å, α=90.00°, β=98.868(4)°, γ=90.00°, V=936.91(10) Å$^3$, wherein each value is ±1.5. For Compound 1, Form A, the formula weight is 435.35 g/mol with Z=2 resulting in a calculated density is 1.543 g cm$^{-3}$. The space group was determined to be P21 (no. 4), this is a chiral space group. A single crystal of Form A of Compound 1 was indexed at room temperature and the unit cell parameters are summarized in Table 5, below.

TABLE 5

Unit Cell Data for Form A

|  | Form A 150° K Data | Form A RT Data |
| --- | --- | --- |
| space group | P2$_1$ (No. 4) | P2$_1$ (No. 4) |
| a, Å | 7.9013(3) | 7.752(2) |
| b, Å | 12.7337(9) | 13.038(12) |
| c, Å | 9.4247(7) | 9.493(3) |
| α, deg | 90 | 90 |
| β, deg | 98.868(4) | 97.98(2) |
| γ, deg | 90 | 90 |
| V, Å$^3$ | 936.19(10) | 945.7 |
| Z | 2 | 2 |
| temp K | 150 | 298 |

Example 2

Preparation of Form B

Compound 1 (52.8 mg) was dissolved in methanol (35 mL) with sonication to obtain a clear solution. The solution was filtered through a 0.2 µm nylon filter (Whatman) and evaporated using a rotary evaporator (ambient temperature bath used). The sample was left on the rotary evaporator for approximately 1 hour after the sample was visually dry. White solid containing birefringent spherulites of needles and blades resulted. XRPD pattern of Form A+peaks was observed when the evaporation was carried out at approx. 45° C.

Example 3

Preparation of Form C

Compound 1 (321.5 mg) was dissolved in TFE (4.28 mL) with sonication. A clear solution resulted. The solution was filtered through a 0.2 µM nylon filter (Whatman) into a clean 20-mL vial. A 500 µL aliquot of the filtered solution was dispensed into a 1-dram vial. Into this vial, aliquots (500 µL) of 1-propanol were dispensed with stirring until a total of 3 mL had been added. A clear solution resulted. The solution was allowed to stand at ambient conditions for approximately 1 hour. The sample was found to contain a very small amount of white precipitate suspended in solution. It was then placed in a refrigerator. A, clear solution containing colorless specks of solid resulted after 5 days. The solution was drawn off with a pipette and discarded, and the solid was allowed to air dry at ambient conditions overnight. The sample containing birefringent pentagonal plates was submitted for single crystal X-ray analysis.

The monoclinic cell parameters and calculated volume are: a=7.7724(6) Å, b=15.2539(6) Å, c=9.7329(6) Å, α=90.00°, β=91.899(3)°, γ=90.00°, V=1153.29(12) Å$^3$, wherein each value is ±1.5. For Compound 1 the formula weight is 496.45 g/mol with Z=2 the resulting calculated density of the crystal structure is 1.430 g cm$^{-3}$. The space group was determined to be P21 (no. 4), this is a chiral space group. The unit cell parameters for Form C are summarized in Table 6, below.

TABLE 6

Unit Cell Data for Form C

|  | Form C<br>150° K Data |
|---|---|
| space group | P2$_1$ (No. 4) |
| a, Å | 7.7724(6) |
| b, Å | 15.2539(6) |
| c, Å | 9.7329(6) |
| b, deg | 91.899(3) |
| V, Å$^3$ | 1153.29(12) |
| Z | 2 |
| crystal dimensions, mm | 0.50 × 0.48 × 0.25 |
| temp K | 150 |

Example 4

Preparation of Form D

Amorphous Compound 1 was dissolved in methanol (concentration approximately 5 mg/mL) with sonication. A clear solution resulted. The solution was filtered through a 0.2 μm nylon filter (Whatman). Fast addition of ethyl acetate to a ratio of 4:1 ethyl acetate:methanol caused Form D to precipitate. The resulting white solid appeared to be non-birefringent and of unknown morphology. Experiments in which ethyl acetate was added more slowly to the same solvent ratio resulted in a clear solution. Slow evaporation of the solution resulted in white solid containing birefringent spherulites of thin needles. A fast evaporation experiment in which toluene replaced ethyl acetate also resulted in white solid containing large birefringent needles.

Example 5

Preparation of Amorphous Compound 1

Amorphous Compound 1 was prepared by lyophilization from an aqueous solution. A cycling DSC experiment was carried out on the amorphous Compound 1 and the glass transition temperature was determined to be approximately 23° C.

Example 6

Polymorph Screening of Compound 1

The forms of Compound 1, as described herein, were identified by a polymorph screen. In this screen, Compound 1 was subjected to a variety of solvents and conditions to effect crystallization or precipitation. The results of this screen are summarized in Tables 7 though 13, below. These Tables indicate the solvent and conditions utilized, the form obtained (as determined by XRPD), and a description of the crystal habit. In these Tables, the conditions are designated as slurry, FE, SC, FD, CP, RE, or SE. Each of these terms is defined in detail below.

As used herein, the term "Crash Precipitation" ("CP") refers to a method where saturated solutions of Compound 1 were prepared in various solvents and filtered through a 0.2-μm nylon filter into an open vial. Aliquots of various antisolvents were dispensed with stirring until precipitation occurred. In some cases, samples were placed in the refrigerator or freezer to facilitate precipitation. Solids were collected by drawing solvent off with a pipette and allowing the solids to air dry at ambient conditions prior to analysis.

As used herein, the term "Freeze Drying" ("FD") refers to a method where a saturated solution of Compound 1 was prepared in water and the solution was filtered through a 0.2-μm nylon filter into an open vial. The solution was frozen in a thin layer on the walls of the vial by rotating in a bath of liquid nitrogen or dry ice and washing isopropanol. The vial containing the frozen sample was placed into a lyophilizing container which was then attached to a Flexi-Dry lyophilizer for one to three days. The temperature was maintained at −50 to −60° C. for the duration of the experiment.

The term "Fast Evaporation" ("FE") refers to a method where solutions of Compound 1 were prepared in various solvents in which samples were sonicated between aliquot additions. Once a mixture reached complete dissolution, as judged by visual observation, the solution was filtered through a 0.2-μm nylon filter. The filtered solution was allowed to evaporate at ambient conditions in an open vial. The solids were isolated and analyzed.

The term "Rotary Evaporation" ("RE") refers to a method where concentrated solutions of Compound 1 or amorphous Compound 1 were prepared in various organic solvents and filtered through a 0.2-μm nylon filter into an open vial or flask. In some cases, 4-5 mL, aliquots of the filtered solution were dispensed into a clean vial. The vial was attached to a rotary evaporator and the solvent was evaporated to dryness. The water bath was at ambient temperature usually, but in some eases, the water bath was heated to approximately 50° C. to facilitate evaporation. If the sample was not completely dry after rotary evaporation, the vial was placed in a vacuum oven at 25° C. for 18 hours. The solids were isolated and analyzed.

As used herein, the term "Slow Cool" ("SC") refers to a method where saturated solutions of Compound 1 were prepared in various solvents at an elevated temperature and filtered warm through a 0.2-μm nylon filter into a warm vial. The vial was capped and left on the hot plate, and the hot plate was turned off to allow the sample to slow cool to ambient temperature.

The term "Slow Evaporation" ("SE") refers to a method where solutions of Compound 1 were prepared in various solvents in which samples were sonicated between aliquot additions. Once a mixture reached complete dissolution, as judged by visual observation, the solution was filtered through a 0.2-μm nylon filter. In some cases, aliquots of antisolvent were then added to the filtered solution with stirring. The solution was allowed to evaporate at ambient conditions in a vial covered with aluminum foil perforated with pinholes. The solids were isolated and analyzed.

The term "Slurry Experiments" refers to a method where suspensions of Compound 1 were prepared by adding enough solids to a given solvent at ambient conditions or elevated temperature so that undissolved solids were present. The mixture was then loaded onto an orbit shaker in a sealed vial at either ambient or elevated temperature for 7 days. The solids were isolated by vacuum filtration or by drawing the liquid phase off with a pipette and allowing the solids to air dry at ambient conditions prior to analysis.

As used herein, the term "Vapor Diffusion Experiments" refers to a method where concentrated solutions of Compound 1 were prepared in various solvents and filtered through a 0.2-μm nylon filter. The filtered solution was dispensed into a 1-dram vial, which was then placed inside a 20-mL vial containing approximately 2 mL of antisolvent. The 1-dram vial was left uncapped and the 20-mL vial was capped to allow vapor diffusion to occur. Solids were collected by vacuum filtration and analyzed.

The terra "Capillary Crystallization Techniques" refers to a method where a capillary polymorph screen was carried out on Compound 1. Various crystallization techniques were employed. These techniques are described below. X-ray powder diffraction quality capillaries were used. Once solids were observed from the crystallization attempts, they were examined under a microscope for birefringence and morphology. Any crystalline shape was noted, but sometimes the solid exhibited unknown morphology, in some cases due to the packing in the capillary or to small particle size. When sufficient, solid samples were then analyzed by XRPD, and the crystalline patterns were compared to each other to identify new crystalline forms.

The term "CentriVap Crystallizations" ("CentriVap") refers to a method where a solution of Compound 1 in a given solvent or solvent mixture was prepared and filtered through a 0.2-μm nylon filter. A capillary was filled with 45 μL of solution via syringe. The capillary was centrifuged. The solvent was evaporated in a Labconco CentriVap® centrifugal evaporator under reduced pressure using a mechanical vacuum pump. The evaporator temperature was maintained at ambient temperature.

The term "Evaporation in Capillary" ("EC") refers to a method where a solution of Compound 1 in a given solvent or solvent mixture was prepared and filtered through a 0.2-μm nylon filter. A capillary was filled with 45 μL of solution via syringe. The capillary was centrifuged. Evaporations were performed in open capillaries at ambient and elevated temperature.

The term "Solvent/Antisolvent Crystallizations in Capillary" refers to a method where a solution of Compound 1 in a given solvent was prepared and filtered through a 0.2-μm nylon filter. A capillary was filled with 15 μL of solution and centrifuged. Then 30 μL of an antisolvent was added. The capillary was centrifuged. If a clear solution resulted, the capillary was left at ambient conditions to allow the solvents to evaporate, or evaporation was performed in a Labconco CentriVap centrifugal evaporator under reduced pressure using a mechanical pump at ambient conditions.

The term "Vapor Diffusion in Solid or Vapor Stress" ("VS") refers to a method where capillaries were packed with approximately 1 cm of Compound 1. The solids were exposed to solvent vapors by placing the capillaries in tall vials containing about 5 mL of various solvents. The capillaries were removed after approximately 14 days.

TABLE 7

Polymorph Screen of Compound 1

| Solvent | Conditions | Habit/Description | XRPD Result |
|---|---|---|---|
| acetone | slurry, 7 days air-dried, 1 day | tiny white plates, birefringent | A |
| acetonitrile | slurry, 7 days air-dried, 1 day | white, morphology unknown, birefringent | A |
| 2-butanone | slurry, 7 days air-dried, 1 day | white, morphology unknown, birefringent | A |
| t-butyl methyl ether | slurry, 7 days air-dried, 3 days | white blades, birefringent | A |
| methylene chloride | slurry, 7 days air-dried, 1 day | white, morphology unknown, birefringent | A |
| diisopropyl ether | slurry, 7 days air-dried, 1 day | white, morphology unknown, birefringent | A |
| 1,4-dioxane | slurry, 7 days air-dried, 3 days | white plates, birefringent | A |
| ethanol | slurry, 4 days | clear solution | — |
|  | FE, air-dried, 3 days | orange glassy film, not birefringent; morphology unknown, birefringent | amorphous |
|  | SC | clear yellow solution | — |
|  | SE | clear yellow solution | — |
|  | RE | yellow glassy film, not birefringent; yellow, morphology unknown, birefringent | amorphous |
| ethyl acetate | slurry, 7 days air-dried, 3 days | white plates and blades, birefringent | A |
| heptane | slurry, 7 days air-dried, 3 days | white, morphology unknown, birefringent | A |
| hexafluoro-isopropanol | FE | clear glassy film, not birefringent | — |
|  | SE | clear glassy film, not birefringent | — |
|  | CP w/ acetonitrile | white, morphology unknown, birefringent | A |
|  | CP w/ 2-butanone | white, morphology unknown, birefringent | A |
|  | CP w/ isopropyl ether | white spherulites of needles and morphology unknown, birefringent | A |
|  | CP w/ 1,4-dioxane | orange plates and morphology unknown, birefringent; morphology unknown, not birefringent | A minus one peak |

TABLE 7-continued

Polymorph Screen of Compound 1

| Solvent | Conditions | Habit/Description | XRPD Result |
|---|---|---|---|
| | CP w/ ethyl acetate | tiny white spherulites of blades, birefringent | A |
| | CP w/ isopropanol | white, morphology unknown, birefringent | amorphous |
| | CP w/ n-propanol | white blades, birefringent | A |
| | RE | white, bubbly solid | amorphous |
| isopropanol | slurry, 7 days | white plates and blades, birefringent | A |
| methanol | FE | tiny white blades, birefringent | A |
| | SE | amber-colored oily film, not birefringent; plates and morphology unknown, birefringent | A |
| | SC | clear solution | — |
| | RE | white spherulites of needles, birefringent | B |
| | RE (scale up) | white spherulites of needles and blades, birefringent | B |
| | | white, morphology unknown, partially birefringent; fibers, birefringent | B |
| | RE at 45° C. to ambient | white, morphology unknown, partially birefringent | A + peaks |
| nitromethane | slurry, 7 days air-dried, 3 days | white, morphology unknown, birefringent | A |
| | FE (liquid phase from slurry 2454-01-12) | amber-colored, large pentagonal plates, birefringent | A |
| nitromethane: hexafluoro-isopropanol 10:1 | SE | white cracked glass, birefringent | A |
| nitromethane: 2,2,2-trifluoroethanol 6:1 | SE | white plates and dendridic needles, birefringent | A |
| 1-propanol | slurry, 7 days air-dried, 3 days | white, morphology unknown, birefringent | A |
| tetrahydrofuran | slurry, 7 days air-dried, 3 days | white plates and blades, birefringent | A |
| toluene | slurry, 7 days air-dried, 3 days | white plates and blades | A |
| toluene: hexafluoro-isopropanol 10:1 | SE | textured glassy film, not birefringent; off-white, morphology unknown, not birefringent; off-white needles, birefringent | A |
| toluene: 2,2,2-trifluoroethanol 6:1 | SE | yellow translucent glassy film, not birefringent | — |
| 2,2,2-trifluoroethanol | FE | clear glassy film, not birefringent | — |
| | SE | clear textured glassy film, not birefringent | — |
| | CP w/ acetonitrile | white plates, birefringent | A |
| | CP w/ 2-butanone | white blades, birefringent | A |
| | CP w/ 1,4-dioxane | white, morphology unknown, birefringent | A |
| | CP w/ ethyl acetate | white, morphology unknown, not birefringent | A |
| | CP w/ isopropanol | white needles and blades, birefringent | A |

TABLE 7-continued

Polymorph Screen of Compound 1

| Solvent | Conditions | Habit/Description | XRPD Result |
|---|---|---|---|
| | CP w/ n-propanol | white, pentagonal plates, birefringent | A + C |
| | RE | white, bubbly solid; dendridic needles, birefringent | amorphous |
| water | FE | yellow glassy film, not birefringent | — |
| | SE | light yellow glassy film, not birefringent | — |
| acetone:water 50:50 | FE | clear glassy film, not birefringent | — |
| | SE | clear glassy film, not birefringent | — |
| acetone:water 99:1 | slurry, 7 days | white plates and blades, birefringent | A |
| acetonitrile:water 80:20 | FE | clear glassy film, not birefringent; colorless, morphology unknown, birefringent | amorphous |
| | SE | clear glassy film, not birefringent; colorless, morphology unknown, birefringent | amorphous |
| acetonitrile:water 99:1 | slurry, 7 days | white plates and blades, birefringent | A |
| isopropanol:water 50:50 | FE | clear glassy film, not birefringent | — |
| | SE | off-white, morphology unknown, birefringent | A |
| isopropanol:water 99:1 | slurry, 7 days | tiny white plates, birefringent | A |
| acetone | slurry, 7 days | white, morphology unknown, birefringent | A |
| acetonitrile | slurry, 7 days | white, morphology unknown, birefringent | A |
| | FE (liquid phase from slurry 2454-20-02) | colorless textured glassy film, not birefringent | — |
| tetrahydrofuran | slurry, 7 days | white, morphology unknown, birefringent | A |

TABLE 8

Vapor Diffusion Experiments

| Solvent | Antisolvent | Time | Habit/Description | XRPD Result |
|---|---|---|---|---|
| hexafluoro-isopropanol | acetone | 6 days | white, morphology unknown, birefringent | A |
| | dichloro-methane | 14 days | clear solution | — |
| 2,2,2-trifluoro-ethanol | acetone | 10 days | translucent, morphology unknown, not birefringent; white plates, birefringent | A |
| | dichloro-methane | 14 days | clear solution | — |

TABLE 9

Capillary Polymorph Screen of Compound 1

| Solvent | Method | Habit/Description | XRPD Result |
|---|---|---|---|
| hexafluoro-isopropanol | EC, ambient | clear solution | — |
| | EC, 40° C. | clear glassy solid, not birefringent | — |
| 2,2,2-trifluoro-ethanol | CentriVap | off-white solid, glassy, not birefringent and viscous liquid | — |
| | EC, ambient | off-white dendridic formations, birefringent | IS |
| | EC, 40° C. | clear yellow glassy solid, not birefringent | — |
| | CentriVap | off-white, morphology unknown, birefringent | A |
| water | EC, ambient | clear yellowish solution | — |
| | EC, 40° C. | clear yellow viscous liquid | — |
| | CentriVap | clear glassy, not birefringent | — |
| acetone:water 50:50 | EC, ambient | clear yellowish solution | — |
| | EC, 40° C. | clear yellowish sticky substance | — |
| | CentriVap | off-white, morphology unknown, birefringent | A (small amount of material |

TABLE 9-continued

Capillary Polymorph Screen of Compound 1

| Solvent | Method | Habit/Description | XRPD Result |
|---|---|---|---|
| acetonitrile: water 50:50 | EC, ambient | yellowish viscous liquid | — |
| | EC, 40° C. | clear yellow glassy solid, not birefringent | — |
| | CentriVap | off-white, morphology unknown, birefringent | A (small amount of material) |
| isopropanol: water 50:50 | EC, ambient | clear yellowish solution | — |
| | EC, 40° C. | Clear orange glassy solid, not birefringent | — |
| | CentriVap | off-white, morphology unknown, birefringent | A |

TABLE 10

Capillary Polymorph Screen of Compound 1 by Solvent/Antisolvent Crystallization

| Solvent | Antisolvent | Method | Habit/Description | XRPD Result |
|---|---|---|---|---|
| HFIPA | acetonitrile | EC | Off-white plate, blades, and rods, birefringent | IS |
| | acetonitrile | CentriVap | clear and yellow glassy solid, not birefringent | — |
| | 2-butanone | precipitation | clear glassy solid, not birefringent | — |
| | ethyl acetate | precipitation | white, morphology unknown, not birefringent | A |
| | isopropyl ether | precipitation | white, morphology unknown, not birefringent | A |
| | isopropanol | EC | Clear glassy solid, not birefringent | — |
| | isopropanol | CentriVap | clear glassy solid, not birefringent | — |
| | n-propanol | EC | clear viscous liquid | — |
| | n-propanol | CentriVap | clear and off-white glassy solid, not birefringent | — |
| | toluene | EC | clear yellowish viscous liquid | — |
| | toluene | CentriVap | clear and yellow glassy solid, not birefringent | — |
| | nitromethane | EC | off-white, unknown morphology, not birefringent and needles, birefringent | A |
| | nitromethane | CentriVap | clear and yellow glassy solid, not birefringent | — |
| TFE | acetonitrile | EC | clear sticky substance | — |
| | acetonitrile | CentriVap | off-white, dendridic formations, birefringent | A |
| | 2-butanone | EC | clear viscous liquid | — |
| | 2-butanone | CentriVap | white, dendridic formations, birefringent | A |
| | ethyl acetate | precipitation | white, morphology unknown, partially birefringent | A |
| | isopropyl ether | precipitation | white, morphology unknown, partially birefringent | A |
| | isopropanol | EC | yellowish viscous liquid | — |
| | isopropanol | CentriVap | off-white, dendridic formations, birefringent | A (big crystals present) |
| | n-propanol | EC | clear solution | — |
| | n-propanol | CentriVap | white, dendridic formations, birefringent | A |
| | toluene | EC | off-white, dendridic formations, birefringent | IS |
| | toluene | CentriVap | off-white, dendridic formations, birefringent | A |
| | nitromethane | EC | off-white, morphology unknown, not birefringent | IS |
| | nitromethane | CentriVap | clear glassy solid, not birefringent | — |

TABLE 11

Capillary Polymorph Screen of Compound 1 by Vapor Stress

| Solvent | Habit/Description | XRPD Result |
|---|---|---|
| acetone | white, morphology unknown, not birefringent | A |
| acetonitrile | white, morphology unknown, not birefringent | A |
| 2-butanone (MEK) | white, morphology unknown, not birefringent | A |
| t-butyl methyl ether (MTBE) | white, morphology unknown, not birefringent | A |
| ethanol | white, morphology unknown, not birefringent | A |
| ethyl acetate | white, morphology unknown, not birefringent | A |
| isopropanol | white, morphology unknown, not birefringent | A |
| methanol | off-white, morphology unknown, not birefringent | B |
| toluene | white, morphology unknown, not birefringent | A |
| 95% RH | white, morphology unknown, not birefringent | A |

TABLE 12

Abbreviated Polymorph Screen of Amorphous Compound 1

| Solvent | Conditions | Habit/Description | XRPD Result |
|---|---|---|---|
| acetone | slurry, 7 days | white, morphology unknown, birefringent | A |

TABLE 12-continued

Abbreviated Polymorph Screen of Amorphous Compound 1

| Solvent | Conditions | Habit/Description | XRPD Result |
|---|---|---|---|
| acetonitrile | slurry, 7 days | white, morphology unknown, birefringent | A, minus one peak |
| acetonitrile:hexafluoro-isopropanol 9:1 | FE | clear glassy film, not birefringent; clear, morphology unknown, birefringent | A, l.c. |
| acetonitrile:methanol 4:1 | SE | clear solution | — |
| | FE | yellow glassy film, not birefringent | — |
| 2-butanone | slurry, 7 days | white, tiny plates, birefringent | A |
| 2-butanone:hexafluoro-isopropanol 9:1 | FE | clear glassy film, not birefringent; clear plates and morphology unknown, birefringent | IS |
| 2-butanone:methanol 4:1 | SE | clear light yellow solution | — |
| | FE | clear oily film, not birefringent; colorless needles and blades, birefringent | IS |
| ethanol | FE | clear glassy film, not birefringent; colorless, morphology unknown, birefringent | amorphous |
| | RE | white, morphology unknown, not birefringent | amorphous |
| ethyl acetate | slurry, 7 days | white, morphology unknown, birefringent | A, minus one peak |
| ethyl acetate:methanol 4:1 | SE | white spherulites of thin needles, birefringent | D |
| | SE, scale-up | yellow needles, birefringent | D + B |
| | | long needles, single crystal quality | B |
| | | a few needles + colorless thin solid film | — |
| | 2410-52-01 + solvent mixture | long needles | — |
| | SE, scale-up | clear solution | — |
| | SE, scale-up | clear solution | — |
| | SE, scale-up | white, long needles | — |
| | Portion of 2482-09-03 | white, long needles, birefringent | B |
| | SE, scale-up | needles | — |
| hexafluoro-isopropanol | FE | clear glassy film, not birefringent | — |
| | CP w/ acetonitrile | clear solution with small amount of translucent solid | — |
| | CP w/ 2-butanone | clear solution with small amount of translucent solid | — |
| | CP w/ ethyl acetate | white blades, birefringent | A |
| | CP w/ isopropanol | clear solution, very small amount of translucent solid | — |
| isopropanol | slurry, 7 days | white plates and blades, birefringent; morphology unknown, not birefringent | A |
| isopropanol:hexafluoro-isopropanol 9:1 | SE | clear glassy film, not birefringent; colorless, morphology unknown, birefringent | IS |
| isopropanol:methanol 4:1 | SE | clear light yellow solution | — |
| | FE | orange glassy film, not birefringent; colorless, morphology unknown, birefringent | A, l.c. |
| isopropyl ether | slurry, 7 days | white, morphology unknown, not birefringent | A |
| methanol | FE | clear glassy film, not birefringent; colorless, morphology unknown, birefringent | amorphous |
| | RE | white, cracked glassy film, not birefringent | amorphous |
| | CP w/ isopropyl ether | white, morphology unknown, not birefringent | B + A |
| | CP w/ ethyl acetate | white, morphology unknown, not birefringent | D |
| | | white precipitate | D |
| | | white, morphology unknown, not birefringent | B |
| | | white, thin needles, partially birefringent | B minus peaks |
| | | white, morphology unknown, partially birefringent | B minus peaks |
| | | white, morphology unknown, partially birefringent | B minus peaks |
| | | white solid | D + B minus peaks |
| | | white solid | D + B minus peaks |
| nitromethane | FE | clear glassy film, not birefringent; white blades, birefringent | A |
| tetrahydrofuran | slurry, 7 days | off-white, morphology unknown, birefringent | A |
| toluene | slurry, 7 days | white, morphology unknown, not birefringent | A |
| toluene:hexafluoro-isopropanol 9:1 | SE | clear solution | — |
| | FE | translucent glassy film, not birefringent; orange, morphology unknown, not birefringent | amorphous |
| toluene:methanol 4:1 | SE | clear solution, small amount of white needles and yellow oil | — |
| | FE | yellow glassy film, not birefringent; white, large needles, birefringent | D |
| 2,2,2-trifluoroethanol | FE | translucent glassy film, not birefringent | — |
| water | FE | light yellow cracked glassy film, not birefringent; light yellow fibers, birefringent | IS |
| acetone:water 99:1 | slurry, 7 days | white, morphology unknown, not birefringent | A |
| acetonitrile:water 99:1 | slurry, 7 days | white needles and morphology unknown, birefringent; morphology unknown, partially birefringent | A |
| isopropanol:water 99:1 | slurry, 7 days | white, morphology unknown, partially birefringent | A |

TABLE 13

Vapor Diffusion Experiments on Amorphous Compound 1

| Solvent | Antisolvent | Time | Habit/Description | XRPD Result |
|---|---|---|---|---|
| hexafluoro-isopropanol | acetone | 11 days | white, morphology unknown, partially birefringent | IS |
| | tetrahydrofuran | 7 days | white, morphology unknown, not birefringent | — |
| 2,2,2-trifluoro-ethanol | acetone | 11 days | white, morphology unknown, birefringent | IS |
| | tetrahydrofuran | 7 days | white, morphology unknown, not birefringent | A |

Example 7

Equilibrium solubilities of Form A in various solvents at room temperature are listed in Table 14, below. In each case, the equilibrium solubility of Form A at room temperature was measured by placing the compound in excess into different solvents and stirring overnight at ambient room temperature, protected from light. Solubility in the following solvents and aqueous buffers was evaluated at room temperature: methanol, ethanol, benzyl alcohol, dimethyl sulfoxide, water for injection, bacteriostatic water (containing 0.9% benzyl alcohol), 5% dextrose, normal saline (0.9% NaCl), pH 1.1 (glycine HCl), pH 4.2 (glycine HCl), pH 7.1 (phosphate buffer), and pH 9.1 (glycine). Solubilities are reported to the nearest mg/mL unless otherwise stated.

An additional set of solubility samples, were prepared under conditions that simulate the human GI tract (pH 1, 0.1 N HCl, pH 4.5 acetate buffer, 7.1 phosphate buffer, pH 9.0 borate buffer). All solutions were stored overnight in a 37° C. oven, and then filtered through a Whatman 0.45 μm nylon syringe filter to remove insoluble material. The filtrate was analyzed by HPLC for strength and the results summarized in Table 14.

TABLE 14

Approximate Solubilities of Form A, at Ambient Temperature

| Solvent | Solubility at R.T. (mg/mL) | Solubility at 37° C. (mg/mL) |
|---|---|---|
| Methanol | 2.5 | N/T |
| Ethanol | 6.1 | N/T |
| Benzyl alcohol | 85.5 | N/T |
| Dimethylsulfoxide | >170 | N/T |
| Water for injection | 73.5 | N/T |
| Bacteriostatic water (0.9% benzyl alcohol) | 86.5 | N/T |
| 5% Dextrose | 61.3 | N/T |
| Normal saline (0.9% NaCl) | 59.7 | N/T |
| 0.1N HCl | 76.6 | 100.8 |
| pH 1.1 (glycine HCl buffer) | 70.1 | N/T |
| pH 4.2 (glycine HCl buffer) | 73.8 | N/T |
| pH 4.5 (acetate buffer) | N/T | 99.97 |
| pH 7.1 (phosphate buffer) | 74.9 | N/T |
| pH 9.1 (glycine buffer) | 71.1 | N/T |
| pH 9.0 (borate buffer) | N/T | 100.6 |
| pH 6.8 (phosphate buffer) | N/T | 100.7 |

N/T = "not tested"

We claim:

1. Form D of Compound 1:

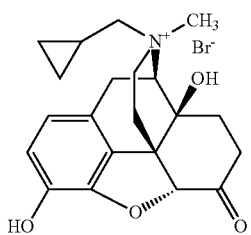

where the compound is in the (R) configuration with respect to the nitrogen, and wherein the compound has an X-ray powder diffraction pattern comprising all of the peaks at about 7.66, 8.42, 14.79, and 21.06 degrees 2-theta.

2. Form D of Compound 1 according to claim 1, wherein the X-ray powder diffraction pattern further comprises peaks at about 12.85, 13.48, 16.11, 17.53, 18.67, 19.61, 21.79, 22.07, 23.25, 24.53, and 26.23 degrees 2-theta.

3. Form D of Compound 1 according to claim 1, characterized in that the compound has an X-ray powder diffraction pattern substantially similar to that depicted in FIG. 6.

4. Form C of Compound 1:

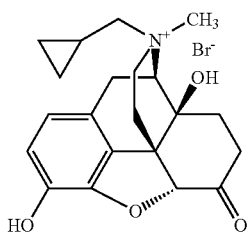

where the compound is in the (R) configuration with respect to the nitrogen, and wherein the compound has an X-ray powder diffraction pattern, calculated from single crystal data collected at a temperature of 150±1° K, comprising all of the peaks at about 10.8, 12.8, 14.8, 15.9, 16.25, 18.5, 19.15, 22, 23.6, 24.25, 25.7, 27.5, 28.1, 28.9, 31.5 and 31.75 degrees 2-theta.

5. Form C of Compound 1 according to claim 4, characterized in that the compound has an X-ray powder diffraction pattern, calculated from single crystal data collected at a temperature of 150±1° K, substantially similar to that depicted in FIG. 8.

6. Form C of Compound 1 according to claim 4, wherein the compound has monoclinic cell parameters of: a=7.7724(6) Å, b=15.2539(6) Å, c=9.7329(6) Å, α=90.00°, β=91.899(3)°, γ=90.00°, wherein each value is ±1.5 Å.

7. A composition comprising a mixture of Form A of Compound 1 and Form C of Compound 1:

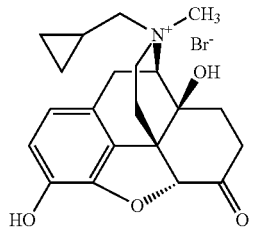

where the compound is in the (R) configuration with respect to the nitrogen, and wherein the composition has an X-ray powder diffraction pattern comprising all of the peaks at about 10.58, 11.56, 13.88, 15.42, 20.82, 21.86, 22.74, 23.2, 24.74, and 26.96 degrees 2-theta.

8. The composition according to claim 7, characterized in that the composition has a X-ray powder diffraction pattern substantially similar to that depicted in FIG. 9.

9. A composition comprising Form D of Compound 1 of claim 1.

10. A composition comprising Form C of Compound 1 of claim 4.

11. A pharmaceutical composition comprising the composition of any one of claims 7, 9 or 10, and a pharmaceutically acceptable carrier, adjuvant, or vehicle.

12. An oral formulation comprising the pharmaceutical composition according to claim 11.

13. A method of reducing a side effect of opioid therapy in a subject receiving opioid treatment comprising administering to the subject the pharmaceutical composition according to claim 11.

14. A method for reducing an effect of endogenous opioid activity in a subject comprising administering to the subject the pharmaceutical composition according to claim 11.

* * * * *